United States Patent
Anderson et al.

(10) Patent No.: US 6,803,203 B1
(45) Date of Patent: Oct. 12, 2004

(54) DNA-PK ASSAY

(75) Inventors: Carl W. Anderson, Stony Brook, NY (US); Margery A. Connelly, Medford, NY (US)

(73) Assignee: Brookhaven Science Associates, Upton, NY (US)

(*) Notice: Subject to any disclaimer, the term of this patent is extended or adjusted under 35 U.S.C. 154(b) by 328 days.

(21) Appl. No.: 09/695,437

(22) Filed: Oct. 24, 2000

Related U.S. Application Data

(63) Continuation-in-part of application No. 08/398,139, filed on Mar. 3, 1995, now abandoned, which is a continuation-in-part of application No. 08/132,284, filed on Oct. 6, 1993, now abandoned.

(51) Int. Cl.[7] .............................. C12Q 1/48; C07K 7/08
(52) U.S. Cl. ......................... 435/15; 435/194; 530/300; 530/324; 530/326; 530/327
(58) Field of Search ................... 435/15, 194; 530/300, 530/324, 326, 327

(56) References Cited

U.S. PATENT DOCUMENTS 5,606,044 A    2/1997    Burrell et al. ............ 536/24.31

OTHER PUBLICATIONS

B. Vojresek et al. "An Immunochemical Analysis of the Human Nuclear Phosphoprotein p53. New Monoclonal Antibodies and Epitope Mapping Using Recombinant p53." J. Immunol. Methods 151(1–2): 237–244. (Jul. 1992).*
K.T. Lam et al. "Hsp70 Binds Specifically to a Peptide Derived From the Highly Conserved Domain (I) Region of p53. ", Biochem. Biophys. Res. Commun. 184(1): 167–174. (Apr. 1992).*
Anderson, et al., "The Human DNA–Activated Protein Kinase, DNA–PK: Substrate Specificity", *Methods in Protein Structure Analysis*, Plenum Press, NY, 1995 pp. 395–406.
Kemp, et al., "Design and Use of Peptide Substrates for Protein Kinases", *Methods in Enzymology*, 200: 121–134 (1991).
Pearson, et al., "Protein Kinase Phosphorylation Site Sequences and Consensus Specificity Motifs: Tabulations", *Methods in Enzymology*, 200: 62–81 (1991).
Glass, et al., "Isolation of Phosphorylated Peptides and Proteins on Ion Exchange Papers", *Analytical Biochemistry*, 87: 566–575 (1978).
Lees–Miller, et al., "Human Cells Contain A DNA–Activated Protein Kinase That Phosphorylates Simian Virus 40 T Antigen, Mouse p53, and the Human Ku Autoantigen", *Molecular and Cellular Biology*, 10: 6472–6481 (1990).
Chen, et al., "The Human DNA–Activated Protein Kinase Phosphorylates Simian Virus 40 T Antigen at Amino– and Carboxy–Terminal Sites", *Journal of Virology*, 65: 5131–5140 (1991).

Jackson, et al., "Preparation and Use of Nuclease–Treated Rabbit Reticulocyte Lysates for the Translation of Euraryotic Messenger RNA", *Methods in Enzymology*, 96: 52–74 (1983).
Ballinger, et al., "Studies of the Kinetics and Ionic Requirements for the Phosphorylation of Ribosomal Protein S6 after Fertilization of *Arbacia punctulata* Eggs", *Developmental Biology*, 101: 192–200 (1984).
Lees–Miller, et al., "Human DNA–Activated Protein Kinase Phosphorylates Serines 15 and 37 in the Amino–Terminal Transactivation Domain of Human p53", *Molecular and Cellular Biology*, 12: 5041–5049 (1992).
Lees–Miller, et al., "Two Human 90–kDa Heat Shock Proteins Are Phosphorylated In Vivo at Conserved Serines That Are Phosphorylated In Vitro by Casein Kinase II", *The Journal of Biological Chemistry*, 264: 2431–2437 (1989).
Stenger, et al., "Formation of Stable p53 Homotetramers and Multiples of Tetramers", *Molecular Carcinogenesis*, 5: 102–106 (1992).
Agostinis, et al., "A Synthetic Peptide Substrate Specific for Casein Kinase–1", *FEB Letters*, 259: 75–78 (1989).
Casnellie, "Assay of Protein Kinases Using Peptides With Basic Residues for Phosphocellulose Binding", *Methods in Enzymology*, 200: 115–120 (1991).

(List continued on next page.)

*Primary Examiner*—Rebecca Prouty
(74) *Attorney, Agent, or Firm*—Margaret C. Bogosian

(57) ABSTRACT

The present invention provides a method for detecting DNA-activated protein kinase (DNA-PK) activity in a biological sample. The method includes contacting a biological sample with a detectably-labeled phosphate donor and a synthetic peptide substrate defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and, (5) a tag moiety, which may be an amino acid sequence or another chemical entity that permits separating the synthetic peptide from the phosphate donor. A compostion and a kit for the detection of DNA-PK activity are also provided. Methods for detecting DNA, protein phosphatases and substances that alter the activity of DNA-PK are also provided. The present invention also provides a method of monitoring protein kinase and DNA-PK activity in living cells. -A composition and a kit for monitoring protein kinase activity in vitro and a composition and a kit for monitoring DNA-PK activities in living cells are also provided. A method for identifying agents that alter protein kinase activity in vitro and a method for identifying agents that alter DNA-PK activity in living cells are also provided.

7 Claims, 25 Drawing Sheets

OTHER PUBLICATIONS

Lees–Miller, et al., "The Human Double–stranded DNA–activated Protein Kinase Phosphorylates the 90–kDa Heat–shock Protein, hsp90α at Two $NH_2$–terminal Threonine Residues", *The Journal of Biological Chemistry*, 264: 17275–17280 (1989).

Soussi, et al., "Structural Aspects of the p53 Protein in Relation to Gene Evolution", *Oncogene* 5: 945–952 (1990).

Dayhoff, "A Model of Evolutionary Change in Proteins", *Atlas of Protein Sequence and Structure*, 5: 345–352 (1978).

Muszyhaka, et al., "Selective Adsorption of Phosphoproteins on Gel–Immobilized Ferric Chelate", *Biochemistry*, 25: 6850–6853 (1986).

Andersson, et al., "Isolation of Phosphoproteins by Immobilized Metal ($Fe^{3+}$) Affinity Chromatography", *Analytical Biochemistry*, 154: 250–254 (1986).

Buss, et al., "Measurement of Chemical Phosphate in Proteins", *Methods in Enzymology*, 99: 7–14 (1983).

* cited by examiner

Phosphorylation of Synthetic Peptides by Purified Human DNA-PK

FIGURE 5B

Expressed Protein Product of pT7HPOU1 pT7HPOU1: Expression Vector for Human Oct-1 POU Domain with His6 leader
T7HPOU1    5005 bases, circular Lab Strain:  #236 = pT7HPOU1/DH5[alpha]
Lab Strain:  #237 = pT7HPOU1/BL21(DE3)

Plasmid Construction:
    Vector: pT7HIS2 (pET-3 with His6 leader and T7 gene 2.5)
            Cut with Nco I and BamH I
    Insert: POU domain from pET11c-OCT1POU (CWA Strain #234) from
            Winship Herr, Cold Spring Harbor Laboratory.  POU
            domain DNA was made by PCR using primers #761 and #430
            (pBR322 EcoR I site).  PCR fragment was cut with NcoI
            and BamHI, purified, and inserted in similarly cut
            pT7HIS2 vector (also called pT7AdEP-DBP).

```
        PREDICTED PROTEIN SEQUENCE OF EXPRESSION PRODUCT
                       Segment: 4469-5005

(SEQ ID NO:59)

Composition

8 Ala         7 Gln        18 Leu        18 Ser
            12 Arg        17 Glu        15 Lys         9 Thr
            11 Asn        11 Gly         8 Met         2 Trp
             6 Asp         6 His         8 Phe         1 Tyr
             2 Cys         9 Ile         6 Pro         4 Val

Mol. wt. unmod. chain = 20,352      Number of residues = 178

Met Ala Ser Met Thr Gly His His His His His His Gly Met Ser Gly
 1           5                     10                    15

Gly Met Glu Glu Pro Ser Asp Leu Glu Glu Leu Glu Gln Phe Ala Lys
            20                  25                   30

Thr Phe Lys Gln Arg Arg Ile Lys Leu Gly Phe Thr Gln Gly Asp Val
            35                  40                   45

Gly Leu Ala Met Gly Lys Leu Tyr Gly Asn Asp Phe Ser Gln Thr Thr
            50                  55                   60
```

FIGURE 5B (Continued)

(SEQ ID NO:59)

```
Ile Ser Arg Phe Glu Ala Leu Asn Leu Ser Phe Lys Asn Met Cys Lys
65              70              75              80

Leu Lys Phe Leu Leu Glu Lys Trp Leu Asn Asp Ala Glu Asn Leu Ser
            85              90              95

Ser Asp Ser Ser Leu Ser Ser Pro Ser Ala Leu Asn Ser Pro Gly Ile
            100             105             110

Glu Gly Leu Ser Arg Arg Arg Lys Lys Arg Thr Ser Ile Glu Thr Asn
        115             120             125

Ile Arg Val Leu Glu Lys Ser Phe Leu Glu Asn Gln Lys Pro Thr Ser
    130             135             140

Glu Glu Ile Thr Met Ile Ala Asp Gln Leu Asn Met Glu Lys Glu Val
145             150             155             160

Ile Arg Val Trp Phe Cys Asn Arg Arg Gln Lys Glu Lys Arg Ile Asn
            165             170             175

Pro
```

Reference: Anderson, C. W., and S. P. Lees-Miller. 1992. The nuclear serine/threonine protein kinase DNA-PK. Crit. Rev. Eukaryotic Gene Express. 2, 283-314.

Figure 5C

NUCLEOTIDE SEQUENCE OF pT7HPOU1

(SEQ ID NO:60)

| | | | | | | |
|---|---|---|---|---|---|---|
| GATCCACAGG | ACGGGTGTGG | TCGCCATGAT | CGCGTAGTCG | ATAGTGGCTC | CAAGTAGCGA | 60 |
| AGCGAGCAGG | ACTGGGCGGC | GGCCAAAGCG | GTCGGACAGT | GCTCCGAGAA | CGGGTGCGCA | 120 |
| TAGAAATTGC | ATCAACGCAT | ATAGCGCTAG | CAGCACGCCA | TAGTGACTGG | CGATGCTGTC | 180 |
| GGAATGGACG | ATATCCCGCA | AGAGGCCCGG | CAGTACCGGC | ATAACCAAGC | CTATGCCTAC | 240 |
| AGCATCCAGG | GTGACGGTGC | CGAGGATGAC | GATGAGCGCA | TTGTTAGATT | TCATACACGG | 300 |
| TGCCTGACTG | CGTTAGCAAT | TTAACTGTGA | TAAACTACCG | CATTAAAGCT | TATCGATGAT | 360 |
| AAGCTGTCAA | ACATGAGAAT | TCTTGAAGAC | GAAAGGGCCT | CGTGATACGC | CTATTTTTAT | 420 |
| AGGTTAATGT | CATGATAATA | ATGGTTTCTT | AGACGTCAGG | TGGCACTTTT | CGGGGAAATG | 480 |
| TGCGCGGAAC | CCCTATTTGT | TTATTTTTCT | AAATACATTC | AAATATGTAT | CCGCTCATGA | 540 |
| GACAATAACC | CTGATAAATG | CTTCAATAAT | ATTGAAAAAG | GAAGAGTATG | AGTATTCAAC | 600 |
| ATTTCCGTGT | CGCCCTTATT | CCCTTTTTTG | CGGCATTTTG | CCTTCCTGTT | TTTGCTCACC | 660 |
| CAGAAACGCT | GGTGAAAGTA | AAAGATGCTG | AAGATCAGTT | GGGTGCACGA | GTGGGTTACA | 720 |
| TCGAACTGGA | TCTCAACAGC | GGTAAGATCC | TTGAGAGTTT | TCGCCCCGAA | GAACGTTTTC | 780 |
| CAATGATGAG | CACTTTTAAA | GTTCTGCTAT | GTGGCGCGGT | ATTATCCCGT | GTTGACGCCG | 840 |
| GGCAAGAGCA | ACTCGGTCGC | CGCATACACT | ATTCTCAGAA | TGACTTGGTT | GAGTACTCAC | 900 |
| CAGTCACAGA | AAAGCATCTT | ACGGATGGCA | TGACAGTAAG | AGAATTATGC | AGTGCTGCCA | 960 |
| TAACCATGAG | TGATAACACT | GCGGCCAACT | TACTTCTGAC | AACGATCGGA | GGACCGAAGG | 1020 |
| AGCTAACCGC | TTTTTTGCAC | AACATGGGGG | ATCATGTAAC | TCGCCTTGAT | CGTTGGGAAC | 1080 |
| CGGAGCTGAA | TGAAGCCATA | CCAAACGACG | AGCGTGACAC | CACGATGCCT | GCAGCAATGG | 1140 |
| CAACAACGTT | GCGCAAACTA | TTAACTGGCG | AACTACTTAC | TCTAGCTTCC | CGGCAACAAT | 1200 |
| TAATAGACTG | GATGGAGGCG | GATAAAGTTG | CAGGACCACT | TCTGCGCTCG | GCCCTTCCGG | 1260 |
| CTGGCTGGTT | TATTGCTGAT | AAATCTGGAG | CCGGTGAGCG | TGGGTCTCGC | GGTATCATTG | 1320 |
| CAGCACTGGG | GCCAGATGGT | AAGCCCTCCC | GTATCGTAGT | TATCTACACG | ACGGGGAGTC | 1380 |

Figure 5C (Continued)

(SEQ ID NO:60)

```
AGGCAACTAT GGATGAACGA AATAGACAGA TCGCTGAGAT AGGTGCCTCA CTGATTAAGC 1440
ATTGGTAACT GTCAGACCAA GTTTACTCAT ATATACTTTA GATTGATTTA AAACTTCATT 1500
TTTAATTTAA AAGGATCTAG GTGAAGATCC TTTTTGATAA TCTCATGACC AAAATCCCTT 1560
AACGTGAGTT TTCGTTCCAC TGAGCGTCAG ACCCCGTAGA AAAGATCAAA GGATCTTCTT 1620
GAGATCCTTT TTTTCTGCGC GTAATCTGCT GCTTGCAAAC AAAAAAACCA CCGCTACCAG 1680
CGGTGGTTTG TTTGCCGGAT CAAGAGCTAC CAACTCTTTT TCCGAAGGTA ACTGGCTTCA 1740
GCAGAGCGCA GATACCAAAT ACTGTCCTTC TAGTGTAGCC GTAGTTAGGC CACCACTTCA 1800
AGAACTCTGT AGCACCGCCT ACATACCTCG CTCTGCTAAT CCTGTTACCA GTGGCTGCTG 1860
CCAGTGGCGA TAAGTCGTGT CTTACCGGGT TGGACTCAAG ACGATAGTTA CCGGATAAGG 1920
CGCAGCGGTC GGGCTGAACG GGGGGTTCGT GCACACAGCC CAGCTTGGAG CGAACGACCT 1980
ACACCGAACT GAGATACCTA CAGCGTGAGC ATTGAGAAAG CGCCACGCTT CCCGAAGGGA 2040
GAAAGGCGGA CAGGTATCCG GTAAGCGGCA GGGTCGGAAC AGGAGAGCGC ACGAGGGAGC 2100
TTCCAGGGGG AAACGCCTGG TATCTTTATA GTCCTGTCGG GTTTCGCCAC CTCTGACTTG 2160
AGCGTCGATT TTTGTGATGC TCGTCAGGGG GGCGGAGCCT ATGGAAAAAC GCCAGCAACG 2220
CGGCCTTTTT ACGGTTCCTG GCCTTTTGCT GGCCTTTTGC TCACATGTTC TTTCCTGCGT 2280
TATCCCCTGA TTCTGTGGAT AACCGTATTA CCGCCTTTGA GTGAGCTGAT ACCGCTCGCC 2340
GCAGCCGAAC GACCGAGCGC AGCGAGTCAG TGAGCGAGGA AGCGGAAGAG CGCCTGATGC 2400
GGTATTTTCT CCTTACGCAT CTGTGCGGTA TTTCACACCG CATATATGGT GCACTCTCAG 2460
TACAATCTGC TCTGATGCCG CATAGTTAAG CCAGTATACA CTCCGCTATC GCTACGTGAC 2520
TGGGTCATGG CTGCGCCCCG ACACCCGCCA ACACCCGCTG ACGCGCCCTG ACGGGCTTGT 2580
CTGCTCCCGG CATCCGCTTA CAGACAAGCT GTGACCGTCT CCGGGAGCTG CATGTGTCAG 2640
AGGTTTTCAC CGTCATCACC GAAACGCGCG AGGCAGCTGC GGTAAAGCTC ATCAGCGTGG 2700
TCGTGAAGCG ATTCACAGAT GTCTGCCTGT TCATCCGCGT CCAGCTCGTT GAGTTTCTCC 2760
```

Figure 5C (Continued)

(SEQ ID NO:60)

```
AGAAGCGTTA ATGTCTGGCT TCTGATAAAG CGGGCCATGT TAAGGGCGGT TTTTTCCTGT 2820
TTGGTCACTG ATGCCTCCGT GTAAGGGGGA TTTCTGTTCA TGGGGGTAAT GATACCGATG 2880
AAACGAGAGA GGATGCTCAC GATACGGGTT ACTGATGATG AACATGCCCG GTTACTGGAA 2940
CGTTGTGAGG GTAAACAACT GGCGGTATGG ATGCGGCGGG ACCAGAGAAA AATCACTCAG 3000
GGTCAATGCC AGCGCTTCGT TAATACAGAT GTAGGTGTTC CACAGGGTAG CCAGCAGCAT 3060
CCTGCGATGC AGATCCGGAA CATAATGGTG CAGGGCGCTG ACTTCCGCGT TTCCAGACTT 3120
TACGAAACAC GGAAACCGAA GACCATTCAT GTTGTTGCTC AGGTCGCAGA CGTTTTGCAG 3180
CAGCAGTCGC TTCACGTTCG CTCGCGTATC GGTGATTCAT TCTGCTAACC AGTAAGGCAA 3240
CCCCGCCAGC CTAGCCGGGT CCTCAACGAC AGGAGCACGA TCATGCGCAC CCGTGGCCAG 3300
GACCCAACGC TGCCCGAGAT GCGCCGCGTG CGGCTGCTGG AGATGGCGGA CGCGATGGAT 3360
ATGTTCTGCC AAGGGTTGGT TTGCGCATTC ACAGTTCTCC GCAAGAATTG ATTGGCTCCA 3420
ATTCTTGGAG TGGTGAATCC GTTAGCGAGG TGCCGCCGGC TTCCATTCAG GTCGAGGTGG 3480
CCCGGCTCCA TGCACCGCGA CGCAACGCGG GGAGGCAGAC AAGGTATAGG GCGGCGCCTA 3540
CAATCCATGC CAACCCGTTC CATGTGCTCG CCGAGGCGGC ATAAATCGCC GTGACGATCA 3600
GCGGTCCAGT GATCGAAGTT AGGCTGGTAA GAGCCGCGAG CGATCCTTGA AGCTGTCCCT 3660
GATGGTCGTC ATCTACCTGC CTGGACAGCA TGGCCTGCAA CGCGGGCATC CCGATGCCGC 3720
CGGAAGCGAG AAGAATCATA ATGGGGAAGG CCATCCAGCC TCGCGTCGCG AACGCCAGCA 3780
AGACGTAGCC CAGCGCGTCG GCCGCCATGC CGGCGATAAT GGCCTGCTTC TCGCCGAAAC 3840
GTTTGGTGGC GGGACCAGTG ACGAAGGCTT GAGCGAGGGC GTGCAAGATT CCGAATACCG 3900
CAAGCGACAG GCCGATCATC GTCGCGCTCC AGCGAAAGCG GTCCTCGCCG AAAATGACCC 3960
AGAGCGCTGC CGGCACCTGT CCTACGAGTT GCATGATAAA GAAGACAGTC ATAAGTGCGG 4020
CGACGATAGT CATGCCCCGC GCCCACCGGA AGGAGCTGAC TGGGTTGAAG GCTCTCAAGG 4080
GCATCGGTCG ACGCTCTCCC TTATGCGACT CCTGCATTAG GAAGCAGCCC AGTAGTAGGT 4140
```

Figure 5C (Continued)

(SEQ ID NO:60)

```
TGAGGCCGTT GAGCACCGCC GCCGCAAGGA ATGGTGCATG CAAGGAGATG GCGCCCAACA  4200
GTCCCCCGGC CACGGGGCCT GCCACCATAC CCACGCCGAA ACAAGCGCTC ATGAGCCCGA  4260
AGTGGCGAGC CCGATCTTCC CCATCGGTGA TGTCGGCGAT ATAGGCGCCA GCAACCGCAC  4320
CTGTGGCGCC GGTGATGCCG GCCACGATGC GTCCGGCGTA GAGGATCGAG ATCTCGATCC  4380
CGCGAAATTA ATACGACTCA CTATAGGGAG ACCACAACGG TTTCCCTCTA GAAATAATTT  4440
TGTTTAACTT TAAGAAGGAG ATATACAT ATG GCT TCT ATG ACT GGT CAC CAC      4492
CAC CAT CAC CAT GGT ATG AGC GGC GGC ATG GAG GAG CCC AGT GAC CTT    4540
GAG GAG CTC GAG CAG TTT GCC AAG ACC TTC AAA CAA AGA CGA ATC AAA    4588
CTT GGA TTC ACT CAG GGT GAT GTT GGG CTC GCT ATG GGG AAA CTA TAT    4636
GGA AAT GAC TTC AGC CAA ACT ACC ATC TCT CGA TTT GAA GCC TTG AAC    4684
CTC AGC TTT AAG AAC ATG TGC AAG TTG AAG CCA CTT TTA GAG AAG TGG    4732
CTA AAT GAT GCA GAG AAC CTC TCA TCT GAT TCG TCC CTC TCC AGC CCA    4780
AGT GCC CTG AAT TCT CCA GGA ATT GAG GGC TTG AGC AGG CGC AGG AAG    4828
AAA CGC ACC AGC ATA GAG ACC AAC ATC CGT GTG GCC TTA GAG AAG AGT    4876
TTC TTG GAG AAT CAA AAG CCT ACC TCG GAA GAG ATC ACT ATG ATT GCT    4924
GAT CAG CTC AAT ATG GAA AAA GAG GTG ATT CGT GTT TGG TTC TGT AAC    4972
CGT CGA CAG AAA GAA AAA AGA ATC AAC CCA TAG                        5005
```

FIGURE 8B

Wild-Type Artificial DNA-PK Substrate 1

Lab Stain: #349 = p349SUB1 in DH5[alpha]
Lab Strain #351 = p349SUB1 in BL21(DE3)

Plasmid Construction:
  VECTOR: p410 = derivative pET-28a (Novagen) without BglII site
  INSERT: Substrate encoding XbaI-BamHI fragment was excised from
          p345 with XbaI and BamHI and cloned into XbaI and BamHI
          cleaved p410.
  ANTIBIOTIC SELECTION: 50 ug/ml Kanamycin

PREDICTED SEQUENCE POUSUB1 ARTIFICIAL DNA-PK SUBSTRATE

Segment: 5258-5860

(SEQ ID NO:61)

Composition

| | | | |
|---|---|---|---|
| 8 Ala | 9 Gln | 22 Leu | 18 Ser |
| 12 Arg | 24 Glu | 16 Lys | 9 Thr |
| 11 Asn | 11 Gly | 7 Met | 3 Trp |
| 9 Asp | 6 His | 9 Phe | 1 Tyr |
| 2 Cys | 9 Ile | 11 Pro | 4 Val |

Mol. wt. unmod. chain = 23,126      Number of residues = 201

```
Met Pro Glu Glu Ser Gln Glu Thr Phe Glu Asp Leu Trp Lys Leu Leu
 1               5                   10                  15

Pro Gly His His His His His His Gly Met Ser Gly Gly Met Glu Glu
           20                      25                  30

Pro Ser Asp Leu Glu Glu Leu Glu Gln Phe Ala Lys Thr Phe Lys Gln
         35                  40              45

Arg Arg Ile Lys Leu Gly Phe Thr Gln Gly Asp Val Gly Leu Ala Met
     50              55              60

Gly Lys Leu Tyr Gly Asn Asp Phe Ser Gln Thr Thr Ile Ser Arg Phe
 65              70              75                      80

Glu Ala Leu Asn Leu Ser Phe Lys Asn Met Cys Lys Leu Lys Pro Leu
                 85              90                  95

Leu Glu Lys Trp Leu Asn Asp Ala Glu Asn Leu Ser Ser Asp Ser Ser
             100             105                 110
```

FIGURE 8B (Continued)

(SEQ ID NO:61)

```
Leu Ser Ser Pro Ser Ala Leu Asn Ser Pro Gly Ile Glu Gly Leu Ser
        115             120             125
Arg Arg Arg Lys Lys Arg Thr Ser Ile Glu Thr Asn Ile Arg Val Ala
    130             135             140
Leu Glu Lys Ser Phe Leu Glu Asn Gln Lys Pro Thr Ser Glu Glu Ile
145             150             155             160
Thr Met Ile Ala Asp Gln Leu Asn Met Glu Lys Glu Val Ile Arg Val
            165             170             175
Trp Phe Cys Asn Arg Arg Gln Lys Glu Lys Arg Ile Asn Pro Gln Pro
            180             185             190
Glu Leu Ala Pro Glu Asp Pro Glu Asp
        195             200
```

NOTES:
```
  Ser 5-Gln 6       = Artificial DNA-PK Site
  Glu 10            = Introduced to make BglII site, =Ser in p53,
                      =Ala in peptide
  His 19-His 24     = His tag for Zn/Ni-affinity chromatography
  Met 26-Gly 29     = Adenovirus Proteinase Cleavage Motif
  Glu 31-Pro 190    = POU specific domain of Human Oct-1
  Gln 191-Asp 201   = Novagen HSV Epitope Tag
```

Figure 8C

NUCLEOTIDE SEQUENCE OF p349SUB1

(SEQ ID NO:62)

| | | | | | |
|---|---|---|---|---|---|
| CGAGCTCCGT | CGACAAGCTT | GCGGCCGCAC | TCGAGCACCA | CCACCACCAC | CACTGAGATC | 60
| CGGCTGCTAA | CAAAGCCCGA | AAGGAAGCTG | AGTTGGCTGC | TGCCACCGCT | GAGCAATAAC | 120
| TAGCATAACC | CCTTGGGGCC | TCTAAACGGG | TCTTGAGGGG | TTTTTTGCTG | AAAGGAGGAA | 180
| CTATATCCGG | ATTGGCGAAT | GGGACGCGCC | CTGTAGCGGC | GCATTAAGCG | CGGCGGGTGT | 240
| GGTGGTTACG | CGCAGCGTGA | CCGCTACACT | TGCCAGCGCC | CTAGCGCCCG | CTCCTTTCGC | 300
| TTTCTTCCCT | TCCTTTCTCG | CCACGTTCGC | CGGCTTTCCC | CGTCAAGCTC | TAAATCGGGG | 360
| GCTCCCTTTA | GGGTTCCGAT | TTAGTGCTTT | ACGGCACCTC | GACCCCAAAA | AACTTGATTA | 420
| GGGTGATGGT | TCACGTAGTG | GGCCATCGCC | CTGATAGACG | GTTTTTCGCC | CTTTGACGTT | 480
| GGAGTCCACG | TTCTTTAATA | GTGGACTCTT | GTTCCAAACT | GGAACAACAC | TCAACCCTAT | 540
| CTCGGTCTAT | TCTTTTGATT | TATAAGGGAT | TTTGCCGATT | TCGGCCTATT | GGTTAAAAAA | 600
| TGAGCTGATT | TAACAAAAAT | TTAACGCGAA | TTTTAACAAA | ATATTAACGT | TTACAATTTC | 660
| AGGTGGCACT | TTTCGGGGAA | ATGTGCGCGG | AACCCCTATT | TGTTTATTTT | TCTAAATACA | 720
| TTCAAATATG | TATCCGCTCA | TGAATTAATT | CTTAGAAAAA | CTCATCGAGC | ATCAAATGAA | 780
| ACTGCAATTT | ATTCATATCA | GGATTATCAA | TACCATATTT | TTGAAAAAGC | CGTTTCTGTA | 840
| ATGAAGGAGA | AAACTCACCG | AGGCAGTTCC | ATAGGATGGC | AAGATCCTGG | TATCGGTCTG | 900
| CGATTCCGAC | TCGTCCAACA | TCAATACAAC | CTATTAATTT | CCCCTCGTCA | AAAATAAGGT | 960
| TATCAAGTGA | GAAATCACCA | TGAGTGACGA | CTGAATCCGG | TGAGAATGGC | AAAAGTTTAT | 1020
| GCATTTCTTT | CCAGACTTGT | TCAACAGGCC | AGCCATTACG | CTCGTCATCA | AAATCACTCG | 1080
| CATCAACCAA | ACCGTTATTC | ATTCGTGATT | GCGCCTGAGC | GAGACGAAAT | ACGCGATCGC | 1140
| TGTTAAAAGG | ACAATTACAA | ACAGGAATCG | AATGCAACCG | GCGCAGGAAC | ACTGCCAGCG | 1200
| CATCAACAAT | ATTTTCACCT | GAATCAGGAT | ATTCTTCTAA | TACCTGGAAT | GCTGTTTTCC | 1260
| CGGGGATCGC | AGTGGTGAGT | AACCATGCAT | CATCAGGAGT | ACGGATAAAA | TGCTTGATGG | 1320
| TCGGAAGAGG | CATAAATTCC | GTCAGCCAGT | TTAGTCTGAC | CATCTCATCT | GTAACATCAT | 1380

Figure 8C (Continued)

(SEQ ID NO:62)

```
TGGCAACGCT ACCTTTGCCA TGTTTCAGAA ACAACTCTGG CGCATCGGGC TTCCCATACA 1440
ATCGATAGAT TGTCGCACCT GATTGCCCGA CATTATCGCG AGCCCATTTA TACCCATATA 1500
AATCAGCATC CATGTTGGAA TTTAATCGCG GCCTAGAGCA AGACGTTTCC CGTTAATAT  1560
GGCTCATAAC ACCCCTTGTA TTACTGTTTA TGTAAGCAGA CAGTTTTATT GTTCATGACC 1620
AAAATCCCTT AACGTGAGTT TTCGTTCCAC TGAGCGTCAG ACCCCGTAGA AAAGATCAAA 1680
GGATCTTCTT GAGATCCTTT TTTTCTGCGC GTAATCTGCT GCTTGCAAAC AAAAAAACCA 1740
CCGCTACCAG CGGTGGTTTG TTTGCCGGAT CAAGAGCTAC CAACTCTTTT TCCGAAGGTA 1800
ACTGGCTTCA GCAGAGCGCA GATACCAAAT ACTGTCCTTC TAGTGTAGCC GTAGTTAGGC 1860
CACCACTTCA AGAACTCTGT AGCACCGCCT ACATACCTCG CTCTGCTAAT CCTGTTACCA 1920
GTGGCTGCTG CCAGTGGCGA TAAGTCGTGT CTTACCGGGT TGGACTCAAG ACGATAGTTA 1980
CCGGATAAGG CGCAGCGGTC GGGCTGAACG GGGGGTTCGT GCACACAGCC CAGCTTGGAG 2040
CGAACGACCT ACACCGAACT GAGATACCTA CAGCGTGAGC TATGAGAAAG CGCCACGCTT 2100
CCCGAAGGGA GAAAGGCGGA CAGGTATCCG GTAAGCGGCA GGGTCGGAAC AGGAGAGCGC 2160
ACGAGGGAGC TTCCAGGGGG AAACGCCTGG TATCTTTATA GTCCTGTCGG GTTTCGCCAC 2220
CTCTGACTTG AGCGTCGATT TTTGTGATGC TCGTCAGGGG GGCGGAGCCT ATGGAAAAAC 2280
GCCAGCAACG CGGCCTTTTT ACGGTTCCTG GCCTTTTGCT GGCCTTTTGC TCACATGTTC 2340
TTTCCTGCGT TATCCCCTGA TTCTGTGGAT AACCGTATTA CCGCCTTTGA GTGAGCTGAT 2400
ACCGCTCGCC GCAGCCGAAC GACCGAGCGC AGCGAGTCAG TGAGCGAGGA AGCGGAAGAG 2460
CGCCTGATGC GGTATTTTCT CCTTACGCAT CTGTGCGGTA TTTCACACCG CATATATGGT 2520
GCACTCTCAG TACAATCTGC TCTGATGCCG CATAGTTAAG CCAGTATACA CTCCGCTATC 2580
GCTACGTGAC TGGGTCATGG CTGCGCCCCG ACACCCGCCA ACACCCGCTG ACGCGCCCTG 2640
ACGGGCTTGT CTGCTCCCGG CATCCGCTTA CAGACAAGCT GTGACCGTCT CCGGGAGCTG 2700
CATGTGTCAG AGGTTTTCAC CGTCATCACC GAAACGCGCG AGGCAGCTGC GGTAAAGCTC 2760
```

Figure 8C (Continued)

(SEQ ID NO:62)

```
ATCAGCGTGG TCGTGAAGCG ATTCACAGAT GTCTGCCTGT TCATCCGCGT CCAGCTCGTT 2820
GAGTTTCTCC AGAAGCGTTA ATGTCTGGCT TCTGATAAAG CGGGCCATGT TAAGGGCGGT 2880
TTTTTCCTGT TTGGTCACTG ATGCCTCCGT GTAAGGGGGA TTTCTGTTCA TGGGGGTAAT 2940
GATACCGATG AAACGAGAGA GGATGCTCAC GATACGGGTT ACTGATGATG AACATGCCCG 3000
GTTACTGGAA CGTTGTGAGG GTAAACAACT GGCGGTATGG ATGCGGCGGG ACCAGAGAAA 3060
AATCACTCAG GGTCAATGCC AGCGCTTCGT TAATACAGAT GTAGGTGTTC CACAGGGTAG 3120
CCAGCAGCAT CCTGCGATGC AGATCCGGAA CATAATGGTG CAGGGCGCTG ACTTCCGCGT 3180
TTCCAGACTT TACGAAACAC GGAAACCGAA GACCATTCAT GTTGTTGCTC AGGTCGCAGA 3240
CGTTTTGCAG CAGCAGTCGC TTCACGTTCG CTCGCGTATC GGTGATTCAT TCTGCTAACC 3300
AGTAAGGCAA CCCCGCCAGC CTAGCCGGGT CCTCAACGAC AGGAGCACGA TCATGCGCAC 3360
CCGTGGGGCC GCCATGCCGG CGATAATGGC CTGCTTCTCG CCGAAACGTT TGGTGGCGGG 3420
ACCAGTGACG AAGGCTTGAG CGAGGGCGTG CAAGATTCCG AATACCGCAA GCGACAGGCC 3480
GATCATCGTC GCGCTCCAGC GAAAGCGGTC CTCGCCGAAA ATGACCCAGA GCGCTGCCGG 3540
CACCTGTCCT ACGAGTTGCA TGATAAAGAA GACAGTCATA AGTGCGGCGA CGATAGTCAT 3600
GCCCCGCGCC CACCGGAAGG AGCTGACTGG GTTGAAGGCT CTCAAGGGCA TCGGTCGAGA 3660
TCCCGGTGCC TAATGAGTGA GCTAACTTAC ATTAATTGCG TTGCGCTCAC TGCCCGCTTT 3720
CCAGTCGGGA AACCTGTCGT GCCAGCTGCA TTAATGAATC GGCCAACGCG CGGGGAGAGG 3780
CGGTTTGCGT ATTGGGCGCC AGGGTGGTTT TTCTTTTCAC CAGTGAGACG GCAACAGCT 3840
GATTGCCCTT CACCGCCTGG CCCTGAGAGA GTTGCAGCAA GCGGTCCACG CTGGTTTGCC 3900
CCAGCAGGCG AAAATCCTGT TTGATGGTGG TTAACGGCGG GATATAACAT GAGCTGTCTT 3960
CGGTATCGTC GTATCCCACT ACCGAGATAT CCGCACCAAC GCGCAGCCCG GACTCGGTAA 4020
TGGCGCGCAT TGCGCCCAGC GCCATCTGAT CGTTGGCAAC CAGCATCGCA GTGGGAACGA 4080
TGCCCTCATT CAGCATTTGC ATGGTTTGTT GAAAACCGGA CATGGCACTC CAGTCGCCTT 4140
```

Figure 8C (Continued)

(SEQ ID NO:62)

```
CCCGTTCCGC TATCGGCTGA ATTTGATTGC GAGTGAGATA TTTATGCCAG CCAGCCAGAC    4200
GCAGACGCGC CGAGACAGAA CTTAATGGGC CCGCTAACAG CGCGATTTGC TGGTGACCCA    4260
ATGCGACCAG ATGCTCCACG CCCAGTCGCG TACCGTCTTC ATGGGAGAAA ATAATACTGT    4320
TGATGGGTGT CTGGTCAGAG ACATCAAGAA ATAACGCCGG AACATTAGTG CAGGCAGCTT    4380
CCACAGCAAT GGCATCCTGG TCATCCAGCG GATAGTTAAT GATCAGCCCA CTGACGCGTT    4440
GCGCGAGAAG ATTGTGCACC GCCGCTTTAC AGGCTTCGAC GCCGCTTCGT TCTACCATCG    4500
ACACCACCAC GCTGGCACCC AGTTGATCGG CGCGAGATTT AATCGCCGCG ACAATTTGCG    4560
ACGGCGCGTG CAGGGCCAGA CTGGAGGTGG CAACGCCAAT CAGCAACGAC TGTTTGCCCG    4620
CCAGTTGTTG TGCCACGCGG TTGGGAATGT AATTCAGCTC CGCCATCGCC GCTTCCACTT    4680
TTTCCCGCGT TTTCGCAGAA ACGTGGCTGG CCTGGTTCAC CACGCGGGAA ACGGTCTGAT    4740
AAGAGACACC GGCATACTCT GCGACATCGT ATAACGTTAC TGGTTTCACA TTCACCACCC    4800
TGAATTGACT CTCTTCCGGG CGCTATCATG CCATACCGCG AAAGGTTTTG CGCCATTCGA    4860
TGGTGTCCGG GATCTCGACG CTCTCCCTTA TGCGACTCCT GCATTAGGAA GCAGCCCAGT    4920
AGTAGGTTGA GGCCGTTGAG CACCGCCGCC GCAAGGAATG GTGCATGCAA GGAGATGGCG    4980
CCCAACAGTC CCCCGGCCAC GGGGCCTGCC ACCATACCCA CGCCGAAACA AGCGCTCATG    5040
AGCCCGAAGT GGCGAGCCCG ATCTTCCCCA TCGGTGATGT CGGCGATATA GGCGCCAGCA    5100
ACCGCACCTG TGGCGCCGGT GATGCCGGCC ACGATGCGTC CGGCGTAGAG GATCGAGATC    5160
GATCTCGATC CGCGAAATT AATACGACTC ACTATAGGGG AATTGTGAGC GGATAACAAT    5220
TCCCCTCTAG AAGTCGACTT TAAGAAGGAG TACCAAG ATG CCT GAG GAA AGT CAG    5275
GAG ACA TTC GAA GAT CTA TGG AAA CTA CTT CCT GGT CAC CAC CAC CAT    5323
CAC CAT GGT ATG AGC GGC GGC ATG GAG GAG CCC AGT GAC CTT GAG GAG    5371
CTC GAG CAG TTT GCC AAG ACC TTC AAA CAA AGA CGA ATC AAA CTT GGA    5419
TTC ACT CAG GGT GAT GTT GGG CTC GCT ATG GGG AAA CTA TAT GGA AAT    5467
```

Figure 8C (Continued)

(SEQ ID NO:62)

```
GAC TTC AGC CAA ACT ACC ATC TCT CGA TTT GAA GCC TTG AAC CTC AGC    5515
TTT AAG AAC ATG TGC AAG TTG AAG CCA CTT TTA GAG AAG TGG CTA AAT    5563
GAT GCA GAG AAC CTC TCA TCT GAT TCG TCC CTC TCC AGC CCA AGT GCC    5611
CTG AAT TCT CCA GGA ATT GAG GGC TTG AGC AGG CGC CGT AAG AAA CGC    5659
ACC AGC ATA GAG ACC AAC ATC CGT GTG GCC TTA GAG AAG AGT TTC TTG    5707
GAG AAT CAA AAG CCT ACC TCG GAA GAG ATC ACT ATG ATT GCT GAT CAG    5755
CTC AAT ATG GAA AAA GAG GTG ATT CGT GTT TGG TTC TGT AAC CGT CGA    5803
CAG AAA GAA AAA AGA ATC AAC CCA CAG CCA GAA CTC GCC CCG GAA GAC    5851
CCC GAG GAT TAGGATCCGA ATT                                          5873
```

DNA-PK ASSAY

The present application is a continuation-in-part of U.S. patent application Ser. No. 08/398,139 filed on Mar. 3, 1995, now abandoned, which is a continuation-in-part of U.S. patent application Ser. No. 08/132,284 filed on Oct. 6, 1993, now abandoned.

This invention was made with Government support under contract number DE-AC02-98CH10886, awarded by the U.S. Department of Energy. The Government has certain rights in the invention.

BACKGROUND OF THE INVENTION

1. Field of the Invention

The present invention relates to compositions and methods useful for detecting the presence and quantifying the amount of double-stranded DNA-activated protein kinase (DNA-PK) in a biological sample and a method of monitoring DNA-PK activity or DNA-PK activity state in living cells.

2. Background of the Related Art

Eukaryotic cells contain many different protein kinases, each having specific functions and properties. Protein kinases are important signal transduction enzymes that regulate many aspects of cell metabolism and cell growth in eukaryotic cells. Protein kinases alter the properties of other enzymes or structural proteins by transferring a phosphate from a donor molecule, often ATP, to one or more acceptor amino acids of a substrate protein. Although the basic amino acids lysine, arginine and histidine can be phosphorylated by certain protein kinases which are primarily associated with bacterial organisms, the most common and more widely recognized phosphate acceptor amino acids in protein substrates in eukaryotic organisms are serine, threonine and/or tyrosine residues. The most common and more well-studied protein kinases are either protein-serine/threonine kinases, which are capable of transferring phosphate groups from donor molecules to serine and threonine acceptor amino acid residues in substrate proteins, or protein-tyrosine kinases, which are capable of transferring phosphate groups from donor molecules to tyrosine acceptor amino acid residues in substrate proteins.

Protein kinases have been found to modulate the activities of proteins in cells by phosphorylating their specific protein substrates. These specific phosphorylation reactions constitute a major mechanism for regulating biochemical pathways in multicellular eukaryotic organisms. Nuclear events, metabolic processes and signal transduction at the cytoplasmic membrane are coordinated through the phosphorylation and dephosphorylation of proteins that perform and, control these processes. Transcription and DNA replication are also regulated by phosphorylation. Most replication and transcription factors are phosphorylated at several sites and often by several different protein kinases. Kinases have been described that are activated by a variety of agents including cyclic nucleotides, phorbol esters, phospholipids, calcium ions, heme groups, double-stranded RNA (dsRNA); and double-stranded DNA (dsDNA). A growing number of nuclear regulatory proteins are known to be phosphorylated, but the kinases which phosphorylate these proteins frequently remain unidentified. Furthermore, many of the kinases which have been identified are not well characterized.

The characterization of many protein kinases has been facilitated by the development of in vitro protein kinase assays that specifically and quantitatively detect a particular kinase in a biological sample. Early work in this area was performed by Glass, et al. and is reported in *Anal. Biochem.*, 87:566 (1978). Glass, et al. developed a procedure for isolating phosphorylated peptides and proteins on ion exchange papers under acidic conditions that is applicable to the study of protein-serine/threonine and protein-tyrosine kinases. The method is not applicable to the study of protein kinases that phosphorylate the basic amino acids because the bond between the phosphate group and the basic amino acid is hydrolyzed in the acidic conditions of the method. The paper-binding method was applied to protein kinase, assays that utilized synthetic peptides with amino acid sequences corresponding to the primary amino acid sequence at the phosphorylation sites of native proteins. Synthetic peptide substrates and methods for their rapid separation from kinase assay reaction mixtures have been useful in the detection, quantitation and characterization of numerous protein kinases.

Studies using substrate proteins and synthetic peptide substrates enabled the demonstration that a given protein kinase, whether of the protein-serine/threonine or the protein-tyrosine kinase class, did not phosphorylate all acceptor amino acid residues in a protein or peptide substrate, but was capable of specific selection of the serine, threonine or tyrosine that was to be phosphorylated in its various protein and peptide substrates. These studies lead to the determination that each protein kinase exhibited a specific phosphorylation site consensus sequence motif requirement for selection of the acceptor amino acid (phosphorylation site) in protein substrates or synthetic peptide substrates. Phosphorylation site consensus sequence motifs are comprised of a phosphorylation site acceptor amino acid (serine, threonine or tyrosine) embedded in a sequence or arrangement of amino acids that is specifically recognized by the protein kinase such that the kinase transfers the phosphate to that acceptor amino acid rather than to serines, threonines or tyrosines that are found elsewhere in the substrate but which are not so embedded. Pearson, et al. in *Methods Enzymol.*, 220:62 (1991) tabulated protein kinase phosphorylation site consensus sequence motifs for over 240 protein-serine/threonine and protein-tyrosine kinases. That tabulation was derived from studies of protein kinases utilizing assays containing protein substrates or assays containing synthetic peptide substrates that were synthesized as analogs of natural phosphorylation site sequences.

Synthetic peptide analogs of phosphorylation site consensus sequence motifs are useful for detecting, quantifying and characterizing protein kinases. Synthetic peptide substrates have played an important role in the study of protein kinase (PK) substrate specificity as well as in the measurement of protein kinase activities in cell extracts. The major goals of designing synthetic peptide substrates for protein kinases are to construct peptides that have excellent kinetic properties and a high degree of specificity (Kemp, et al, 1991, *Methods Enzymol.*, 200:121; Pearson, et al., 1991, *Methods Enzymol.*, 200:62).

While synthetic peptides with amino acid sequences corresponding to the primary amino acid sequence at the phosphorylated sties of proteins have been found to serve as specific substrates for certain protein kinases, the degree of specificity of synthetic peptide substrates varies widely. A number of synthetic peptides act as substrates for multiple protein kinases. For example, phosphorylate kinase, protein kinase C, and the multi-functional calmodulin-dependent protein kinase all phosphorylate Ser[7] in a glycogen synthase peptide.

Synthetic peptide substrates for protein kinases are particularly useful if they are specifically phosphorylated only by the protein kinase of interest. A specific synthetic peptide substrate comprises a kinase-specific phosphorylation site consensus sequence motif and sufficient additional amino acids (amino acid spacer sequences) so as to create a peptide providing excellent kinetic properties in an assay. Preferably, a specific synthetic peptide substrate provides a kinase-specific phosphorylation site consensus sequence motif and sufficient amino acid spacer sequences so as to provide excellent kinetic properties in an assay and which amino acid spacer sequences do not provide another phosphorylation site consensus sequence motif. Additionally preferable is a specific synthetic peptide substrate providing a kinase-specific phosphorylation site consensus sequence motif, sufficient amino acid spacer sequences to provide excellent kinetic properties in an assay that do not provide another phosphorylation site consensus sequence motif and which amino acid spacer sequences do not contain another phosphate acceptor amino acid. To provide for economic synthetic procedures, it is especially preferable that a specific synthetic peptide substrate be as short as possible while providing the features described above.

Recently, a kinase that undergoes activation by linear double stranded (ds) DNA was discovered. This kinase is now known as the double-stranded DNA-activated (or dependent) protein kinase (DNA-PK). DNA-PK is perhaps the most abundant nuclear protein kinase in human cells. It is active in vitro only when certain double-stranded DNA molecules are also present. Both natural DNAs and synthetic oligonucleotides are DNA-PK activators. DNA-PK is a protein-serine/threonine kinase and therefore phosphorylates certain serine and threonine residues in specific polypeptide sequences by transferring a phosphate from the γ-position of a suitable phosphate donor, such as adenosine triphosphate (ATP), to specific serine and threonine acceptor amino acids in its substrate proteins.

DNA-PK phosphorylates several viral and cellular proteins in vitro, including the simian virus 40 large tumor antigen (SV40 TAg), heat shock protein (hsp90), the human and murine p53 tumor suppressor proteins, and several transcription factors including Sp1, Oct-1, Fos, Jun and Serum Response Factor (SRF). Many of these proteins are DNA-binding proteins that function in RNA transcription, DNA replication, DNA recombination and DNA repair. The ability of DNA-PK to phosphorylate these regulatory proteins provides a means for elucidating important regulatory pathways. DNA-PK may be useful for studying the extent to which phosphorylation regulates gene expression and cell growth. Additionally, DNA-PK may be an important cellular enzyme in that it may play a role in transcription regulation, DNA replication, and/or DNA repair. DNA-PK may be a regulatory kinase which may be useful in detecting damaged DNA. The phosphorylation of cellular protein substrates by DNA-PK may activate cell cycle checkpoint mechanisms that arrest cell cycle progression in response to DNA damage. DNA-PK may also regulate processes involved in the development of cellular immunity. These and other properties suggest that DNA-PK may be extremely important for regulating the state or utilization of cellular DNA, especially in primate cells.

To determine the function of DNA-PK, it is necessary to understand the factors that result in its activation in cells. A significant technical difficulty in characterizing and studying DNA-PK has been the lack of a simple, quantitative, specific assay analogous to the synthetic peptide substrate assays, as mentioned above, which are available for other protein-serine/threonine kinases and protein-tyrosine kinases. The procedures for the synthesis of peptides for the study of cyclic nucleotide-dependent protein kinases may be applicable to the preparation of synthetic peptides which are specific for DNA-PK.

Previous research has shown that purified SV40 TAg and murine p53 protein were phosphorylated in vitro on serines by the human DNA-activated protein kinase, DNA-PK (Lees-Miller, et al., 1990, *Mol. Cell Biol.*, 10:6472–6481). More recently it was shown that the 14-residue synthetic peptide corresponding to TAg $Thr^{661}$ to $Pro^{674}$ was phosphorylated by DNA-PK primarily on the serine equivalent to TAg residue 665 (Chen, et al., 1991, *J. Virol.*, 10:5131–5140).

Several attempts have been made to provide a quantitative specific assay for DNA-PK. However, these attempts have failed. All known natural protein substrates for DNA-PK are also phosphorylated by other protein kinases. For example, casein which is a substrate of DNA-PK, is inexpensive and readily available. Unfortunately, casein is phosphorylated by several protein-serine/threonine kinases and therefore its phosphorylation, after incubation with a biological sample, for example, would not be a specific measure of DNA-PK activity in the biological sample. Hsp90 is a more specific DNA-PK substrate, but it can also be phosphorylated by CKII (and perhaps other kinases). In addition, although hsp90 is abundant and easy to purify, its purification requires several days' work. Further, the quantitation of hsp90 phosphorylation is cumbersome and the kinetic constants for hsp90 phosphorylation are less than ideal. Consequently, simple cost-effective methods for accurately detecting the presence of DNA-PK are needed.

A further complication in characterizing and studying DNA-PK has been the lack of a meaningful correlation between the activity observed in vitro and DNA-PK activity in vivo. DNA-PK is activated in vitro by linear double-stranded DNA fragments, by nicked or gapped double-stranded DNAs or by DNAs with single-to-double strand transitions (bubbles, forks, hairpins, etc.) (Morozov, et al., 1994, *J. Biol. Chem.* 269:16684–16688). The preparation of cell extracts, for the determination of DNA-PK activity, inevitably introduces nicks and breaks into endogenous cellular DNA. DNA-PK or its Ku targeting/regulatory domain binds to the DNA at these nicks or breaks and becomes artificially activated. This artificial activation of DNA-PK upon cell disruption to form cell extracts makes it impossible to measure the status of intracellular DNA-PK activity using an in vitro cell extract assay.

An intracellular, in vivo method for measuring the intracellular DNA-PK activity and the activation status of DNA-PK within, a cell would provide an alternative strategy. Such a strategy could include a determination of the in vivo phosphorylation state of known substrates. However, nearly all of the putative physiological substrates of DNA-PK are proteins that are present in cells at low abundance, making quantitation difficult. In addition, these proteins are also phosphorylated by other protein kinases. Consequently, it has not been possible to ascertain the activity state of DNA-PK in living cells by examining the phosphorylation state of suspected substrates. Further, determining the activity of DNA-PK in cells or changes in its activity by examining the state of endogenous substrates is also complicated by the fact that determining the phosphorylation state of these proteins most often requires incubating cells with radioactive $^{32}PO_4$. The radiation emitted by this compound produces single-strand and double-strand breaks in the endogenous cellular DNA which alters the activity of DNA-PK in living cells. In fact, as previously mentioned, part of the in vivo function of DNA-PK may be to detect such DNA damage. It is known, for example, that radioactive nucleic acid precursors (e.g. [$^3$H]-thymidine) cause an accumulation of the tumor suppressor protein p53, a putative DNA-PK substrate (Dover, et al.,1994, *J. Cell Sci.* 107:1181–1184). Further, p53 accumulation in response to DNA breaks and other damage arrests cell cycle progression in the G$_1$ phase of the cell cycle (Nelson, et al., 1994, *Mol. Cell. Biol.* 14:1815–1823).

In light of the foregoing, it is a purpose of the present invention to provide a composition that comprises a synthetic peptide substrate which is a specific substrate for DNA-PK and which therefore can be used to specifically detect, quantitate and monitor DNA-PK activity.

Another purpose of the present invention is to provide specific quantitative methods of detecting the presence of DNA-PK activity in a biological sample.

Another purpose of the present invention is to provide methods of monitoring DNA-PK activity in living cells.

A further goal of the present invention is to provide a method of identifying agents which modulate DNA-PK activity in vivo and in vitro.

A further purpose of the present invention is to provide a kit for in vitro detection of the presence and relative amount of DNA-PK in a biological sample.

An additional purpose of the present invention is to provide a kit for monitoring the intracellular activity and activation status of DNA-PK.

SUMMARY OF THE INVENTION

These and other purposes and goals are accomplished by the present invention which provides a composition that comprises a synthetic peptide substrate that is a specific substrate for DNA-PK and which therefore is useful to specifically detect, quantitate and monitor DNA-PK activity. The synthetic peptide substrate of the present invention is a peptide substrate defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, of which spacer sequences may include any combination of amino acids that does not provide a phosphorylation site consensus sequence motif; and, (5) a tag moiety, which may be an amino acid sequence or another chemical entity that permits separating the synthetic peptide from the phosphate donor.

Synthetic peptide substrates providing some or all of these features include: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Asn Asn Val Leu: Ser Pro Leu Pro Ser Gln Ala Met Asp Asp Leu Met Lys Lys (SEQ ID NO: 6), Met Ala Ile Tyr Lys Gln Ser Gln His Met Thr Glu Val Val Arg Arg (SEQ ID NO: 7), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Leu Glu Ala Phe Ala Asp Leu Trp Lys Lys (SEQ ID NO: 14), Glu Pro Pro Gln Ser Gln Ala Phe Ala Asp Leu Trp Lys Lys (SEQ ID NO: 15), Glu Pro Pro Leu Thr Gln Glu Ala Phe Ala Asp Leu Trp Lys Lys (SEQ ID NO: 16), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

In a preferred embodiment the synthetic peptide substrate providing all of the features described above to provide specific recognition and phosphorylation by DNA-PK is a synthetic peptide substrate which is identical to or a variant of the amino acid sequence found at the amino terminus of human or murine p53 tumor suppressor proteins, and which contains either Ser$^{15}$ of human p53 tumor suppressor protein or Ser$^7$ or Ser$^{18}$ of murine p53 protein, including the following synthetic peptides: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser. Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Gln Glu Ala Phe Ala Asp Leu Trp Lys Lys (SEQ ID NO: 15), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18), Pro Glu Ser Gln Glu Ala Phe Ala Asp Leu Trp Lys Lys (SEQ ID NO: 19), Pro Leu Ser Gln Glu Thr Phe Ser Gly Leu Trp Lys Leu Leu Pro Pro-Lys Lys (SEQ ID NO: 63), and Pro Leu Ser Gln Glu Ala Phe Ala Gly Leu Trp Lys Leu Leu Pro Pro-Lys Lys (SEQ ID NO: 64).

In a most preferred embodiment the synthetic peptide substrate providing all of the features described above to provide specific recognition and phosphorylation by DNA-PK is a synthetic peptide substrate which is a variant of the amino acid sequence found at the amino terminus of human p53 tumor suppressor proteins, and which contains Ser$^{15}$ of human p53 tumor suppressor protein, including the following peptides: Glu Pro Pro Leu Ser Gln Glu Ala Phe Ala Asp Leu Trp Lys Lys (SEQ ID NO: 11), Glu Pro Pro Gln Ser Gln Glu Ala Phe Ala Asp Leu Trp Lys Lys (SEQ ID NO: 15), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

The present invention also provides a quantitative method for detecting the presence of DNA-PK activity in biological samples. The method includes forming a reaction mixture by contacting a biological sample with a detectably-labeled phosphate donor and a synthetic peptide substrate in the presence or absence of added exogenous DNA. The synthetic peptide substrate is a peptide substrate defined by the following features to provide specific recognition and phosphorylation by DNA-PK: (1) a phosphate-accepting amino acid pair which may include serine-glutamine (Ser-Gln)

(SQ), threonine-glutamine (Thr-Gln) (TQ), glutaminie-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and, (5) a tag moiety, which may be an amino acid sequence or another chemical entity that permits separating the synthetic peptide from the phosphate donor. Synthetic peptide substrates providing some or all of these features include: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Asn Asn Val Leu Ser Pro Leu Pro Ser Gln Ala Met Asp Asp Leu Met Lys Lys (SEQ ID NO: 6), Met Ala lie Tyr Lys Gln Ser Gln His Met Thr Glu Val Val Arg Arg (SEQ ID NO: 7), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Leu Glu Ala Phe Ala Asp Leu Trp Lys Lys (SEQ ID NO: 14), Glu Pro Pro Gln Ser Gln Glu Ala Phe Ala Asp Leu Trp Lys Lys (SEQ ID NO: 15), Glu Pro Pro Leu Thr Gln Glu Ala Phe Ala Asp Leu Trp Lys Lys (SEQ ID NO: 16), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

In a preferred embodiment of this method, a biological sample is contacted with a synthetic peptide substrate which provides all of the features described above to provide specific recognition and phosphorylation by DNA-PK and which is identical to or a variant of the amino acid sequence found at the amino terminus of human or murine p53 tumor suppressor proteins, and which contains either $Ser^{15}$ of human p53 tumor suppressor protein or $Ser^7$ or $Ser^{18}$ of murine p53 protein, including the following synthetic peptides: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Gln Glu Ala Phe Ala Asp Leu Trp Lys Lys (SEQ ID NO: 15), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18), Pro Glu Ser Gln Glu Ala Phe Ala Asp Leu Trp Lys Lys (SEQ ID NO: 19), Pro Leu Ser Gln Glu Thr Phe Ser Gly Leu Trp Lys Leu Leu Pro Pro-Lys Lys (SEQ ID NO: 63), and Pro Leu Ser Gln Glu Ala Phe Ala Gly Leu Trp Lys Leu Leu Pro Pro-Lys Lys (SEQ ID NO: 64).

In a most preferred embodiment of this method, a biological sample is contacted with a synthetic peptide substrate which provides all of the features described above to provide specific recognition and phosphorylation by DNA-PK and which is a variant of amino acid sequence found at the amino terminus of human p53 tumor suppressor proteins, and which contains $Ser^{15}$ of human p53 tumor suppressor protein, including the following peptides: Glu Pro Pro Leu Ser Gln Glu Ala Phe Ala Asp Leu Trp Lys Lys (SEQ ID NO: 11), Glu Pro Pro Gln Ser Gln Glu Ala Phe Ala Asp Leu Trp Lys Lys (SEQ ID NO: 15), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

Next, the reaction mixture is incubated for a time at a temperature to allow the transfer of phosphate from the phosphate donor to the acceptor amino acid in the synthetic peptide substrate. After the incubation step, the transfer of phosphate from the phosphate donor to the acceptor amino acid in the synthetic peptide substrate is stopped. Finally, the method is used to determine the amount of phosphate which was transferred from the phosphate donor to the acceptor amino acid in the synthetic peptide substrate and to correlate the amount of phosphate transferred with a concentration of DNA-PK in a biological sample.

In a preferred embodiment of the invention, the gamma phosphate of the phosphate donor, ATP, contains a radioactive phosphorous isotope, e.g. [$^{32}$P] or [$^{33}$P]. After the incubation, the synthetic peptide, containing the radioactive phosphate transferred by DNA-PK from the radiolabeled ATP, is separated from remaining labeled ATP and phosphate using the tag moiety of the peptide substrate. In a preferred embodiment, this separation is accomplished by absorbing the peptide to phosphocellulose and washing the phosphocellulose with dilute acid to remove the unreacted ATP phosphate donor. The amount of radioactivity transferred to the peptide is then determined using a device, such as a scintillation counter, a beta particle detector, gamma ray detector, or a phosphoimager, to quantitate the radioactivity in a known portion of the reaction. The amount of phosphate transferred to the peptide is then calculated from the known specific activity of the ATP.

A method of detecting the presence of linear double-stranded DNA in a biological sample is also provided. The method includes forming a reaction mixture by contacting a biological sample with a detectably-labeled phosphate donor, DNA-PK and a synthetic peptide substrate defined by the following features to provide specific recognition and phosphorylation by DNA-PK: (1),a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gln-Thr) (QT); (2) enhancer amino acids which may include glutamic: acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor. The transfer of phosphate from the phosphate donor to the peptide substrate is indicative of the presence of linear double-stranded DNA in the sample because it is required for activation of DNA-PK and was not supplied in the reaction mixture.

A method of detecting the presence of substances in a sample that alter the activity of DNA-PK and DNA is also provided. The method includes forming a reaction mixture by contacting increasing amounts of a sample with a detectably-labeled phosphate donor, DNA-PK, linear double-stranded DNA and a synthetic peptide substrate defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair arid forming an amino acid pair-enhancer unit; (3) a, first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and, (5) a tag moiety, which may be an amino acid sequence or another chemical entity that permits separating the synthetic peptide from the phosphate donor. Changes in the amount or rate of transfer of phosphate from the phosphate donor to the peptide substrate caused by contacting the sample is related to the presence of substances that alter the activity of DNA-PK.

The present invention also provides a method of detecting the presence of protein phosphatases in a biological sample. The method includes contacting a biological sample with a phosphorylated synthetic peptide substrate defined by the following features to provide specific recognition by DNA-PK: (1) a phosphorylated amino acid pair which may include phosphoserine-glutamine ($PO_4 \cdot Ser\text{-}Gln$), phosphothreonine-glutamine ($PO_4 \cdot Thr\text{-}Gln$), glutamine-phosphoserine ($Gln\text{-}PO_4 \cdot Ser$), or glutamine-phosphothreonine ($Gln\text{-}PO_4 \cdot Thr$); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor. The loss of phosphate from the phosphorylated peptide substrate is related to the presence of protein phosphatase in the sample.

The present invention also provides a composition useful in the specific, quantitative detection of DNA-PK activity in a biological sample. The composition is a synthetic peptide substrate defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamne-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor.

The present invention also provides a kit for detecting the presence of DNA-PK activity in a biological sample for use in accordance with the method of the present invention. The kit includes a detectably-labeled phosphate donor, double-stranded DNA, a composition useful in specific detection and quantitation of DNA-PK which comprises a synthetic peptide substrate that is phosphorylated by DNA-PK, a negative control peptide that is not phosphorylated by DNA-PK, a preparation of DNA-PK and a reagent to separate the substrate peptide from the phosphate donor.

A negative control peptide that is not phosphorylated by DNA-PK may include a synthetic peptide with an amino acid sequence and composition similar to that of the synthetic peptide substrate, but with a variation of:the phosphorylation site consensus sequence motif such that the acceptor amino acid is no longer phosphorylated by DNA-PK. Peptides with amino acid sequences and compositions that are similar to that of the synthetic peptide substrate may generally be comprised of the same amino acids as the peptide substrate with an alteration of the primary sequence such that the peptide no longer contains the appropriate phosphorylation site consensus motif and is thus not phosphorylated by the DNA-PK. Such negative control peptides thus provide non-phosphorylated peptides that have the same ionic and physical properties as the phosphorylated synthetic peptide substrate.

In the present invention, a negative control peptide may include a synthetic peptide identical in sequence to the synthetic peptide substrate with the single exception that the phosphorylated serine or threonine of the amino acid pairs serine-glutamine (SQ), threonine-glutamine (TQ), glutamine-serine (QS), or glutamine-threonine (QT) of the synthetic peptide substrate is replaced with a non-phosphorylated amino acid such as alanine or other neutral amino acid that does not alter the ionic character of the peptide.

In the present invention, a negative control peptide may also include a synthetic peptide identical in amino acid composition and sequence to the synthetic peptide substrate with the single exception that the enhancer amino acid glutamic acid is inserted between the serine and glutamine of the serine-glutamine (SQ) amino acid pair, or between the threonine and glutamine of the threonine-glutamine (TQ) amino acid, or between the glutamine and the serine of the glutamine-serine (QS) pair or between the glutamine and the threonine of the glutamine-threonine (QT) pair of the peptide rather than being located immediately adjacent at the amino- or carboxyl-side of the amino acid pair.

A method of monitoring intracellular protein kinase activity is also provided by the present invention. The method includes introducing an expression vector into a cell, in which the expression vector has the following features to provide monitoring intracellular protein kinase activity: (1) a gene coding for a protein substrate having a protein segment containing a phosphorylation site consensus sequence motif specific for a protein kinase; (2) an optional nuclear localization signal; (3) an optional DNA-binding domain; and (4) a detectable epitope. The expression of this protein substrate provides a phosphorylated protein substrate. By determining the amount of phosphorylated protein substrate, a correlation to the concentration of protein kinase activity in the cell is made.

The present invention also provides a method for monitoring intracellular DNA-PK activity. The method includes introducing an expression vector into a cell, in which the expression vector has the following features to provide for monitoring intracellular DNA-PK activity: (1) a gene coding for a protein substrate having a protein segment containing a phosphorylation site consensus sequence motif specific for DNA-PK; (2) a nuclear localization signal; (3) a DNA-binding domain; and (4) a detectable epitope. The expression of this protein substrate provides a phosphorylated protein substrate. By determining the amount of phosphorylated protein substrate, a correlation to the concentration of DNA-PK activity in the cell is made.

In either embodiment of the present invention for monitoring intracellular protein kinase activity, the protein substrate can further include: (1) an epitope for affinity purification; and (2) a cleavage site which permits excision of the phosphorylation site from the protein segment.

The present invention also provides a composition for monitoring intracellular protein kinase activity. The composition is an expression vector having the following features to facilitate monitoring protein kinase activity: (1) a gene coding for a protein substrate having a protein segment containing a phosphorylation site consensus sequence motif specific for a protein kinase; (2) an optional nuclear localization signal; (3) an optional DNA-binding domain; and (4) a detectable epitope.

A composition for monitoring intracellular DNA-PK activity is also provided by the present invention. The composition is an expression vector having the following features to facilitate monitoring DNA-PK activity: (1) a gene coding for a protein substrate having a protein segment containing a phosphorylation site consensus sequence motif specific for DNA-PK; (2) a nuclear localization signal; (3) a DNA-binding domain; and (4) a detectable epitope.

The present invention also provides a kit for monitoring intracellular protein kinase activity for use in accordance with the methods of the present invention. The kit includes: (1) an expression vector containing a gene coding for a protein substrate having a protein segment containing a phosphorylation site consensus sequence motif, in which the phosphorylation site consensus sequence motif is specific for a protein kinase, a nuclear localization signal, a DNA-binding domain, and a detectable epitope; and (2) means for detecting a phosphorylated protein substrate. The detection of the phosphorylated protein substrate is utilized to determine the amount of protein kinase activity in the cell.

A kit for monitoring intracellular DNA-PK activity for use in accordance with the methods of the present invention is also provided. The kit includes: (1) an expression vector containing a gene coding for a protein substrate having a protein segment containing a phosphorylation site consensus sequence motif specific for DNA-PK, a nuclear localization signal, a DNA-binding domain, and a detectable epitope; and (2) means for detecting a phosphorylated protein substrate. The detection of the phosphorylated protein substrate is utilized to determine the amount of the DNA-PK activity in the cell.

The present invention also provides a method for identifying agents that alter the activity of a protein kinase in a cell. The method includes introducing an expression vector into a cell, in which the expression vector has the following features to facilitate identification of the agents: (1) a gene coding for a protein substrate having a protein segment containing a phosphorylation site consensus sequence motif specific for a protein kinase; (2) an optional nuclear localization signal; (3) an optional DNA-binding domain; and (4) a detectable epitope. The cell is contacted with the suspected agent. The expression of the protein substrate by the cell provides a phosphorylated protein substrate from which the amount of phosphorylated protein substrate is determined. The amount of phosphorylated protein substrate is then correlated to the concentration of protein kinase activity in the cell and changes in the activity resulting from contacting the cell with the suspected agent.

A method for identifying agents that alter the activity of a DNA-PK in a cell is also provided by the present invention. The method includes introducing an expression vector into a cell, in which the expression vector has the following features to facilitate identification of the agents: (1) a gene coding for a protein substrate having a protein segment containing a phosphorylation site consensus sequence motif specific for DNA-PK; (2) a nuclear localization signal; (3) a DNA-binding domain; and (4) a detectable epitope. The cell is contacted with the suspected agent. The expression of the protein substrate by the cell provides a phosphorylated protein substrate from which the amount of phosphorylated protein substrate is determined. The amount of phosphorylated protein substrate is correlated to the concentration of the DNA-PK activity in said cell and changes in the activity resulting from contacting the cell with the suspected agent.

The present invention also provides a method for monitoring a protein kinase activity in a cell through the expression of a reporter gene. The method includes introducing an expression vector into a cell, in which the expression vector has the following features to facilitate monitoring a protein kinase activity: (1) a gene coding for a protein substrate having a protein segment containing a phosphorylation site consensus sequence motif specific for the protein kinase; (2) an optional nuclear localization signal; (3) an optional DNA-binding domain; and (4) a detectable epitope. The expression of the protein substrate provides a phosphorylated protein substrate, which is capable of activating expression of a reporter gene to provide a reporter gene product. By determining the amount of reporter gene product expressed, a correlation to the concentration of protein kinase activity in the cell is made.

A method for monitoring a DNA-PK activity in a cell through the expression of a reporter gene is also provided by the present invention. The method includes introducing an expression vector into a cell, in which the expression vector has the following features to facilitate monitoring DNA-PK activity: (1) a gene coding for a protein substrate having a protein segment containing a phosphorylation site consensus sequence motif specific for DNA-PK; (2) a nuclear localization signal; (3) a DNA-binding domain; and (4) a detectable epitope. The expression of the protein substrate provides a phosphorylated protein substrate, which is capable of activating expression of a reporter gene to provide a reporter gene product. By determining the amount of reporter gene product expressed, a correlation to the concentration of DNA-PK activity in the cell is made.

For a better understanding of the present invention, reference is made to the following description taken together with the accompanying drawings and sequence listings, the scope of which is pointed out in the appended claims.

BRIEF DESCRIPTION OF THE DRAWINGS

FIG. 5B depicts the primary amino acid sequence of the expressed protein product of plasmid pT7HPOU1 (SEQ ID NO: 59).

FIG. 5C depicts the nucleotide sequence for plasmid pT7HPOU1 (SEQ ID NO: 60).

FIG. 8B depicts the primary amino acid sequence of the expressed product of plasmid p349SUB1 (SEQ ID NO: 61).

FIG. 8C depicts the nucleotide sequence for plasmid p349SUB1 (SEQ ID NO: 62).

DETAILED DESCRIPTION OF THE INVENTION

Figure 1:
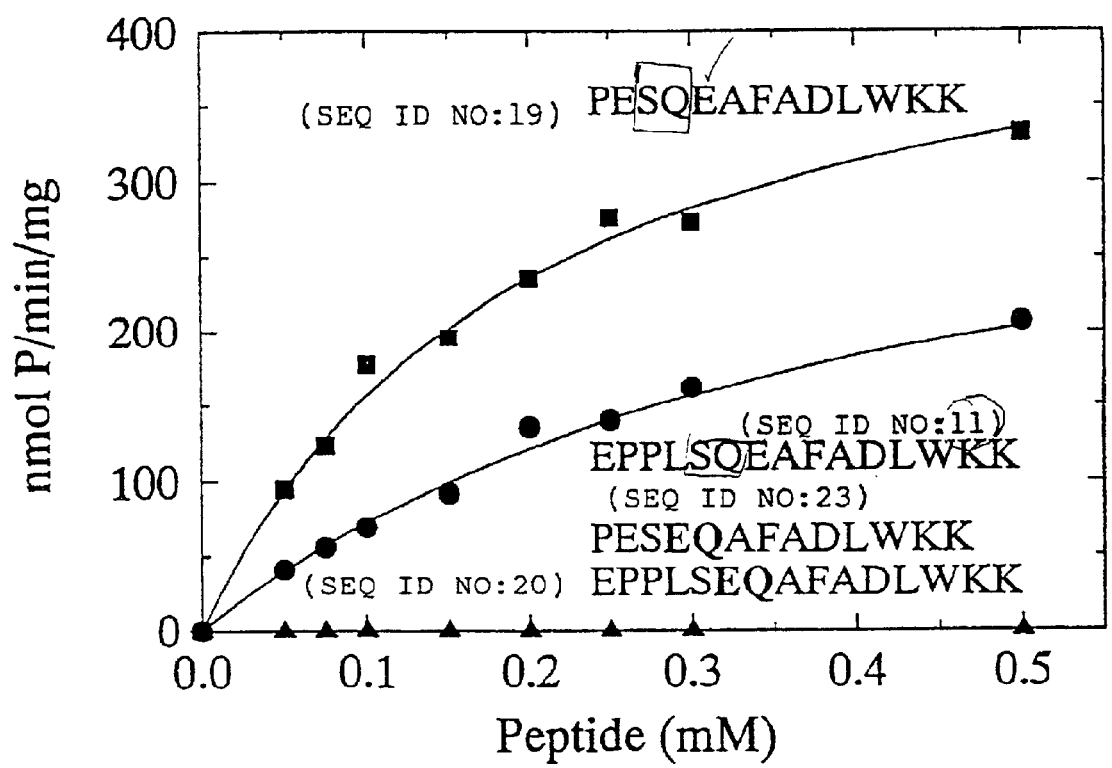
FIG. 1 is a graphical representation of the rates of peptide phosphorylation (nanomoles of phosphate incorporated per minute per milligram of DNA-PK protein) as a function of peptide concentration for synthetic peptide (SEQ ID NO: 11) and synthetic peptide (SEQ ID NO: 19). The amino acid sequences of (SEQ ID NOS: 11 and 19) are listed in Table 1.
Figure 2:
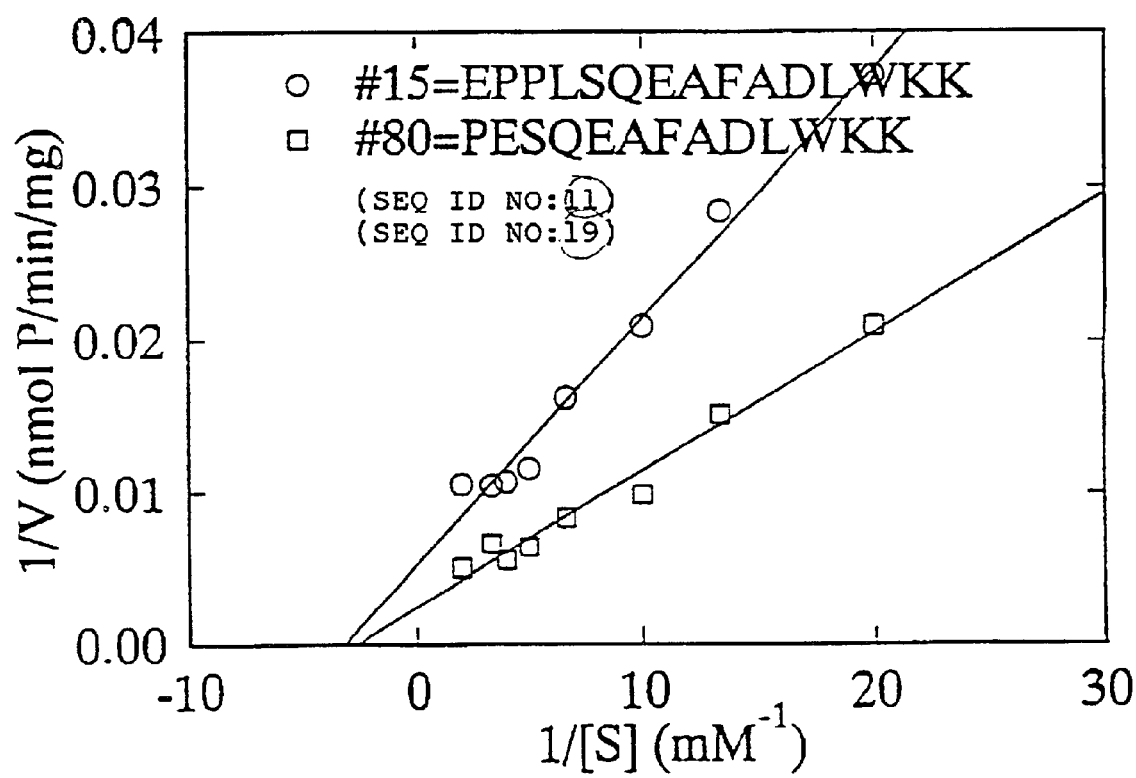
FIG. 2 is a graphical representation of reciprocal plots used to determine the key substrate parameters, $V_{max}$ and $K_m$, for reactions of DNA-PK with synthetic peptide (SEQ ID NO: 11) and synthetic peptide (SEQ ID NO: 18).
Figure 3:
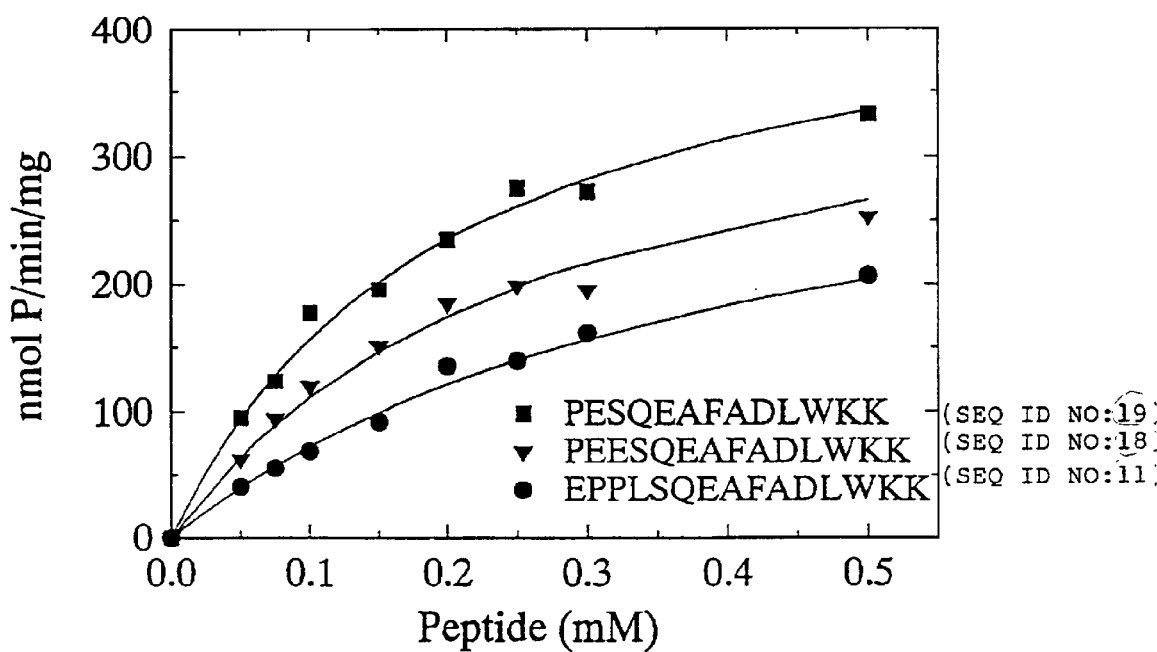
FIG. 3 is a graphical representation of the rates of peptide phosphorylation (nanomoles of phosphate incorporated per minute per milligram of DNA-PK protein) as a function of peptide concentration for synthetic peptide (SEQ ID NO: 19), synthetic peptide (SEQ ID NO: 11), and synthetic peptide (SEQ ID NO: 18). The amino acid sequences of (SEQ ID NOS: 19, 11 and 18) are listed in Table 1.

In accordance with the present invention a method and kit for detecting DNA-PK activity are provided. The method includes forming a reaction mixture by contacting a biological sample with a detectably-labeled phosphate donor and a synthetic peptide substrate in the presence or absence of added exogenous DNA wherein the synthetic peptide substrate is a peptide substrate defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor. Synthetic peptide substrates providing some or all of these features include: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Le:u Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Asn Asn Val Leu Ser Pro Leu Pro Ser Gln Ala Met Asp Asp Leu Met Lys Lys (SEQ ID NO: 6), Met Ala Ile Tyr Lys Gln Ser Gln His Met Thr Glu Val Val Arg Arg (SEQ ID NO: 7), Glu Pro Pro Leu Ser Gln Glu Thr Phe Ser Asp Leu Trp Lys Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Trp Lys Lys (SEQ ID NO: 12), Glu Pro Pro Gln Ser Glen Glu Ala Phe Ala Asp Leu Leu Lys Lys (SEQ ID NO: 14) Glu Pro Pro Gln Ser Gln Glu Ala Phe Ala Asp Leu Trp Lys Lys (SEQ ID NO: 15), Glu Pro Pro Leu Gln Gln Glu Ala Phe Ala Asp Leu Trp Lys Lys (SEQ ID NO: 16), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

In a preferred embodiment of this method, a biological sample is contacted with a synthetic peptide substrate which provides all of the features described above to provide specific recognition and phosphorylation by DNA-PK and which is identical to or a variant of the amino acid sequence found at the amino terminus of human or murine p53 tumor suppressor proteins, and which, contains either Ser[15] of human p53 tumor suppressor protein or Ser[7] or Ser[18] of murine p53 protein, including the following synthetic peptides: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Glu Pro Pro Leu Ser Gln Glu Thr Phe Ser Asp Leu Trp Lys Lys (SEQ ID NO: 8), Glu Pro Pro Leu Ser Gln Gln Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Gln Glu Ala Phe Ala Asp Leu Trp Lys Lys (SEQ ID NO: 15), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18), Pro Glu Ser Gln Glu Ala Phe Ala Asp Leu Trp Lys Lys (SEQ ID NO: 19), Pro Leu Ser Gln Gln Thr Phe Ser Gly Leu Trp Lys Leu Leu Pro Pro-Lys Lys (SEQ ID NO: 63), and Pro Leu Ser Gln Glu Ala Phe Ala Gly Leu Trp Lys Leu Leu Pro Pro-Lys Lys (SEQ ID NO: 64).

In a most preferred embodiment of this method, a biological sample is contacted with a synthetic peptide substrate which provides all of the features described above to provide specific recognition and phosphorylation by DNA-PK and which is a variant of amino acid sequence found at the amino terminus of human p53 tumor suppressor proteins, and which contains Ser$^{15}$ of human p53 tumor suppressor protein, including the following peptides: Glu Pro Pro Leu Ser Gln Glu Ala Phe Ala Asp Leu Trp Lys Lys (SEQ ID NO: 11), Glu Pro Pro Gln Ser Gln Glu Ala Phe Ala Asp Leu Trp Lys Lys (SEQ ID NO: 15), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

Examples of amino acid tag moieties include but are not limited to (1) two or more basic amino acids (arginine or lysine) that, in conjunction with the amino-terminus, permit binding to phosphocellulose, (2) three or more acidic residues that permit binding to an anion exchange resin, (3) six or more histidines that permit binding to immobilized nickel or zinc ions and (4) an amino acid sequence that is recognized by a monoclonal or polyclonal antibody.

Next, the reaction mixture is incubated, preferably at 30° C., for a time, preferably for seven to ten minutes, facilitating the transfer of phosphate from the phosphate donor to the synthetic peptide substrate. The transfer of phosphate to the synthetic peptide substrate is stopped by the addition of an acid, preferably an equal volume of 30% acetic acid, or by the addition of a sufficient amount of detergent or other substance known to inhibit enzyme activity. The amount of labeled phosphate transferred to the synthetic peptide is then determined. In a preferred method, to determine the amount of labeled phosphate transferred to the synthetic peptide, the reaction mixtures are spotted onto phosphocellulose filter paper and washed to remove any unreacted labeled ATP phosphate donor molecules. The filter papers containing the synthetic peptide are transferred to scintillation vials and the bound radioactivity is determined from the Cerenkov radiation.

The amount of phosphate transferred to the synthetic peptide substrates is calculated and compared to negative controls which do not contain DNA-PK and positive controls which contain a known amount of DNA-PK. The amount of phosphate transferred to the synthetic peptide substrate is then correlated with a concentration of DNA-PK in the biological sample. In particular, the amount of phosphate transferred to the synthetic peptide substrate is calculated from the specific activity of the phosphate donor and that amount is compared to the amount of phosphate transferred in various negative control reactions including negative control reactions that do not contain synthetic peptide substrate, or those containing a negative control peptide that is not phosphorylated by DNA-PK, or those lacking activating DNA, or those which contain no biological sample or other source or preparation of DNA-PK. The amount of excess phosphate transferred to the substrate peptide compared to appropriate negative control reactions provides a specific measure of the amount of DNA-PK that is present. The assay may be used to compare the amounts of DNA-PK in two or more biological samples, or from the known specific activity of the kinase, to provide a minimal estimate of the absolute amount of active and/or activatable DNA-PK that is present in the sample.

All known natural protein substrates for DNA-PK are also phosphorylated by other protein kinases. Thus, phosphorylation of such natural protein substrates following contact with a biological sample is not completely attributable nor necessarily related to DNA-PK activity. An advantage of using the synthetic peptide substrate of the present invention which is specific for DNA-PK in the assay compared to using protein substrates known to be phosphorylated by DNA-PK (e.g. casein, hsp90, SV40 T-antigen), is that the measured activity is specific for DNA-PK because the other protein kinases do not phosphorylate the synthetic peptide substrate of the present invention.

Another advantage of using a synthetic peptide substrate of the present invention which is specific for DNA-PK in the assay, compared to using protein substrates known to be phosphorylated by DNA-PK (e.g. casein, hsp90, SV40 T-antigen), is that appropriate negative control peptides may be used to ensure that the measured activity is specific for DNA-PK. If a negative control peptide becomes phosphorylated following contact with a biological sample it would suggest that some portion of the activity measured with the DNA-PK peptide substrate may have been attributable to an unknown protein kinase also contained in the biological sample. Thus, further testing would be required to accurately assess the amount and activity of the DNA-PK in the biological sample.

A negative control peptide that is not phosphorylated by DNA-PK may include a synthetic peptide providing an amino acid sequence and composition similar to that of the DNA-PK synthetic peptide substrate, but with a variation of the phosphorylation site consensus sequence motif such that the acceptor amino acid is no longer recognized nor phosphorylated by DNA-PK or other protein kinases. Peptides providing amino acid sequences and compositions that are similar to those of the synthetic peptide substrate may generally contain the same amino acids as the peptide substrate, but with an alteration of the primary sequence such that the peptide no longer contains a phosphorylation site consensus motif for DNA-PK and is thus not recognized nor phosphorylated by the DNA-PK. Such negative control peptides thus provide non-phosphorylated peptides that have the same ionic; and physical properties of the phosphorylated synthetic peptide substrate.

In a preferred embodiment of the present invention, negative control peptides may include synthetic peptides identical in sequence to the synthetic peptide substrate with the single exception that the phosphorylated serine or threonine of the amino acid pairs serine-glutamine (SQ), threonine-glutamine (TQ), glutamine-serine (QS), or glutamine-threonine (QT) of the synthetic peptide substrate is replaced with a non-phosphorylated amino acid such as alanine or other neutral amino acid that does not alter the ionic character of the peptide.

In an additionally preferred embodiment of the present invention, negative control peptides may include synthetic peptides identical in amino acid composition and sequence to the synthetic peptide substrate with the single exception that the enhancer amino acid glutamic acid is inserted between the serine and glutamine of the serine-glutamine (SQ) amino acid pair, or between the threonine and glutamine of the threonine-glutamine (TQ) amino acid, or between the glutamine and the serine of the glutamine-serine (QS) pair or between the glutamine and the threonine of the glutamine-threonine (QT) pair of the peptide rather than being located immediately adjacent at the amino- or carboxyl-side of the phosphate-accepting amino acid pair.

Control peptides are used to estimate and correct for the incorporation of phosphate by DNA-PK into other peptides and proteins or other substances in the assay, or for the incorporation of phosphate by other kinases into assay components. As discussed, control peptides should not be phosphorylated by DNA-PK but, in general, should resemble substrate peptides in sequence and composition as closely as possible. Thus, Glu Pro Pro Leu Ser Glu Gln Ala Phe Ala Asp Leu Trp Lys Lys (SEQ ID NO: 20) might serve as a negative control peptide for the substrate peptide Glu Pro Pro Leu Ser Gln Glu Ala Phe Ala Asp Leu Trp Lys Lys (SEQ ID NO: 11) since their compositions are identical, but the negative control peptide (SEQ ID NO: 20) lacks the mandatory phosphorylation site consensus sequence motif serine-glutamine (SQ) by virtue of changing the Ser-Gln-Glu sequence of the substrate peptide to Ser-Glu-Gln in (SEQ ID NO: 20). Similarly, Pro Glu Ser Glu Gln Ala Phe Ala Asp Leu Trp Lys Lys (SEQ ID NO: 23) might serve as a negative control peptide for substrate peptide Pro Glu Ser Gln Glu Ala Phe Ala Asp Leu Trp Lys Lys (SEQ ID NO: 19). (SEQ ID NO: 20) and (SEQ ID NO: 23) have the same compositions as substrate peptides (SEQ ID NO: 11) and (SEQ ID NO: 19), respectively, but the order of the Gln and Gnu are reversed so as to disrupt the requisite serine-glutamine phosphate-accepting amino acid pair of the DNA-PK synthetic peptide substrates and therefore they are not phosphorylated by DNA-PK (Table 1). The peptide Glu Pro Pro Leu Ala Gln Glu Ala Phe Ala Asp Leu Trp Lys Lys (SEQ ID NO: 21) might serve as a negative control peptide for the substrate peptide Glu Pro Pro Leu Ser Gln Glu Ala Phe Ala Asp Leu Trp Lys Lys (SEQ ID NO: 1). Glu Pro Pro Leu Ala Gln Glu Ala Phe Ala Asp Leu Trp Lys Lys (SEQ ID NO: 21) has an alanine substituted for the serine of the phosphate accepting amino acid pair; and therefore has no site that can be phosphorylated by a serine/threonine protein kinase but it is otherwise identical in sequence to the substrate peptide. Similar to the above examples, negative control peptides for the substrate peptide Pro Glu Glu Ser Gln Glu Ala Phe Ala Asp Leu Trp Lys Lys (SEQ ID NO: 18) are represented by Pro Glu Glu Ala Gln Glu Ala Phe Ala Asp Leu Trp Lys Lys (SEQ ID NO: 24) and Pro Glu Glu Ser Glu Gln Ala Phe Ala Asp Leu Trp Lys Lys (SEQ ID NO: 25).

Glu Pro Pro Leu Ala Gln Glu Thr Phe Ser Asp Leu Trp Lys Lys (SEQ ID NO: 22) is an appropriate negative control peptide for Glu Pro Pro Leu Ser Gln Glu Thr Phe Ser Asp Leu Trp Lys Lys (SEQ ID NO: 8) since it does not have a Ser-Gln or Gln-Ser or Thr-Gln or Gln-Thr phosphate-accepting amino acid pair site for DNA-PK. SEQ ID NO: 22) is not phosphorylated efficiently by DNA-PK, but it does contain a serine and a threonine that might be recognized and phosphorylated by other kinases in biological samples. Thus, if the DNA-PK protein kinase activity of a biological sample was determined using (SEQ ID NO: 8) as the peptide substrate, using (SEQ ID NO: 22) as the negative control would appropriately test whether some of the phosphate incorporated following contact with the biological sample was attributable to the presence of an unknown protein kinase activity.

Conversely, peptides such as Pro Glu Glu Ala Gln Glu Thr Phe Ser Asp Leu Trp Lys Lys (SEQ ID NO: 26), for example, would be inappropriate negative control peptides for the substrate peptide Pro Glu Glu Ser Gln Glu Ala Phe Ala Asp Leu Trp Lys Lys (SEQ ID NO: 18) because of the presence of the serine and the threonine residues in (SEQ ID NO: 26) that might be recognized and phosphorylated by other kinases in biological samples and because of their absence from the peptide substrate (SEQ ID NO: 18).

In a particularly preferred embodiment, the gamma phosphate of the phosphate donor ATP, is labeled with a radioactive phosphorous isotope, e.g. [$^{32}$P] or [$^{33}$P]. After the incubation, the synthetic peptide, containing the radioactive phosphate transferred by DNA-PK from the radiolabeled ATP, is separated from remaining labeled ATP and phosphate using the tag moiety. In one preferred embodiment, this separation is accomplished by absorbing the peptide to phosphocellulose and washing the phosphocellulose with dilute acid to remove unbound ATP. The amount of radioactivity transferred to the peptide is then determined using a device, such as a scintillation counter, a beta particle detector, gamma ray detector, or a phosphoimager, to quantitate the radioactivity in a known portion of the reaction. The amount of phosphate transferred to the peptide is then calculated from the known specific activity of the ATP. For example, if the specific activity of the ATP were 300 Ci/mole and the amount of radioactivity transferred to the peptide were 0.003 microcuries, then the amount of phosphate transferred to the peptide in the portion measured is 1 nanomole (0.003 µCi divided by 300 Ci/mole).

One unit of DNA-PK activity currently is defined as 1 nanomole of phosphate transferred per minute per mg of protein at 30° C. at pH 7.5, 100 mM KCl, 25 mM HEPES buffer (standard assay conditions) with either hsp90 as a substrate or 200 µM synthetic peptide as a substrate as specified (Lees-Miller et al., 1990, *Mol. Cell. Biol.* 10: 6472–6481; Lees-Miller et al., 1992, *Mol. Cell. Biol.* 12:5041–5049). Using the peptide Glu Pro Pro Leu Ser Gln Glu Ala Phe Ala Asp Leu Trp Lys Lys (SEQ ID NO: 11) as the substrate, 1 mg of purified kinase provides approximately 50 units of DNA-PK activity under these conditions. This is a minimum estimate as the preparation is not completely pure and has not been optimized for the ratio of a 450-kDa catalytic subunit and a targeting subunit known as the Ku autoantigen. Both subunits are required for activity with the peptide assay. Thus, a biological sample yielding a DNA-PK assay result of 1 unit of activity per milliliter would likely have a maximum DNA-PK concentration of approximately 20 µg/ml DNA-PK (1 U/ml divided by 50 U/mg).

In another preferred embodiment, exogenous linear double-stranded DNA is added to the reaction mixture as described in Example 4. The exogenous DNA may include DNA from the following list: plasmid DNA, viral DNA, bacteriophage DNA, calf thymus DNA, salmon testes DNA, salmon sperm DNA, herring sperm DNA, herring testes DNA, *Escherichia coli* DNA, *Micrococcus lysodeikticus* DNA, *Clostridium perfingens* DNA, *Clostridium welchii* DNA, human placenta DNA, synthetically prepared double-stranded DNA fragments, and sources of DNA including chromatin, viruses, cell nuclei and mixtures thereof. The synthetic double-stranded oligonucleotides may be (DG-dC)$_n$ and (dC-DG)$_n$, where n is equal to 7 to 15 (i.e. (GCGC)$_n$ or (CGCG)$_n$) and where the total length is 14 to 30 base pairs. Other synthetic oligonucleotides or DNAs that are not completely double stranded also may be used, for example, circular DNAs with gaps or bubbles, and linear DNAs with single stranded tails. It has been suggested that DNA-PK may have a physical requirement for a DNA end or free 5' nucleotide to become activated in vitro (Anderson and Lees-Miller, 1992, *Crit. Rev. in Eukaryotic Gene Expression*, 2:283–314). Therefore, the above list of DNAs is not exhaustive, but merely representative, as virtually any DNA can be manipulated to provide such an end or free 5' nucleotide and therefore function in the present invention.

The DNA is added to the reaction mixture to provide a concentration of DNA ranging from about 0.01 µg/ml to about 1000 µg/ml of the reaction mixture. In a particularly preferred embodiment, the DNA is added to provide a concentration of from about 5 µg/ml to about 15 µg/ml of the reaction mixture, while in a most preferred embodiment the DNA is added to provide a concentration of DNA of about 10 µg/ml of the reaction mixture.

The detectably-labeled phosphate donor may be [$^{32}$P]-ATP, [$^{32}$P]-dATP, [$^{33}$P]-ATP, [$^{33}$P]-dATP and mixtures thereof. In a preferred embodiment the detectably-labeled phosphate donor is [$^{32}$P]-ATP. The [$^{32}$P]-ATP and non-radioactive ATP are added to the reaction mixture to provide a concentration of ATP ranging from about 20 µM to about 1 mM. The [$^{32}$P]-ATP has an approximate specific activity of 300 mCi/mmole.

In principal, radioactive ATP is not required for detection of phosphate transferred to a peptide. Non-radioactive methods can be used to detect peptide substrate phosphorylation. Phosphorylation of the peptide can be determined from changes in absorbance, fluorescence or changes in the chemical or electrophoretic properties of the peptide. These methods may be coupled with methods for detecting phosphate or the peptide. For example, there are at least three methods for detecting the transfer of non-radioactive phosphate to a peptide: (1) increased mass of the peptide due to the addition of one or more phosphates; (2) increased negative charge of the peptide due to phosphate addition; and (3) binding of the peptide through the phosphate to chelated iron.

The masses of peptides are measured with sensitivity and accuracy using commercial mass spectrometers. A change in the charge of a peptide can be determined by using thin-layer electrophoresis on cellulose plates. The peptide may be detected either by including a chromophor (e.g. nitrophenylalanine, rhodamine coupled to lysine, etc.) in the peptide sequence, or by staining the peptide after electrophoresis with reagents specific for either the peptide sequence (e.g. a monoclonal antibody) or for a specific chemical property of the peptide (e.g. an amino group). Phosphate, including peptide-bound phosphate, binds very tightly to chelated iron at acid pH and is released at alkaline pH. Thus phosphopeptides can be separated from most non-phosphorylated peptides by passing the peptide mixture over a column of iron immobilized on Chelating-Sepharose (Sigma Chemical Co., St. Louis, Mo.) at acid pH and then eluting bound peptide with an alkaline buffer or phosphate. Increased sensitivity can be realized by combining two or more methods; e.g. iron-purified peptides could be subjected to mass analysis or separated by thin-layer electrophoresis. The amount of phosphate transferred to the peptide is quantitatively measured either from a direct chemical measurement of the phosphate in the purified phosphopeptide, or by quantitating the amount of phosphopeptide produced. This is determined by quantitative amino acid analysis of the purified phosphopeptide or by comparing it quantitatively to a phosphopeptide standard of known concentration.

In accordance with the method of the present invention, the synthetic peptide substrate is added to the reaction mixture to provide a concentration of substrate ranging from about 50 $\mu$M to about 1000 $\mu$M. In a preferred embodiment, the synthetic peptide substrate is added to provide a concentration of substrate ranging from about 100 $\mu$M to about 400 $\mu$M of the reaction mixture, while in a most preferred embodiment synthetic peptide substrate is added to provide a concentration of substrate of about 200 $\mu$M of the reaction mixture.

In carrying out the method, the reaction mixture is incubated from about 1 second to about 60 minutes. Preferably the reaction mixture is incubated from about 2 minutes to about 15 minutes, while in a most preferred embodiment the reaction mixture is incubated from about 7 minutes to about, 10 minutes. The reaction mixture is incubated at a temperature ranging from about 5° C. to about 45° C. In a preferred embodiment the reaction mixture is incubated at a temperature from about 20° C. to about 37° C., while in a most preferred embodiment the reaction mixture is incubated at a temperature of about 30° C.

The method of the present invention has other uses in addition to the detection of DNA-PK activity in biological samples. For example, the method may be used to detect double-stranded DNA in samples and to estimate the concentration of DNA in such samples, to detect and estimate the concentration of a phosphate donor in samples, to detect and study substances that alter any of these reagents, i.e. DNA-PK, DNA, phosphate donor that would alter the activity of DNA-PK, and to detect and study enzymes that remove phosphate from the substrate peptide.

In particular, by providing DNA-PK in a reaction, and omitting exogenous DNA from the reaction, the method is configured to detect DNA in a biological sample. The method includes forming a reaction mixture by contacting a biological sample with a detectably-labeled phosphate donor, a source of DNA-PK and a synthetic peptide substrate defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor.

The method of detecting DNA in a biological sample is identical to the method of detecting DNA-PK, except that DNA-PK is added to the reaction mixture and exogenous DNA is not added. Since DNA-PK is dependent on the presence of linear double-stranded DNA or DNA with duplex-to-single-stranded transitions for catalyzing the transfer of phosphate, if such DNA is present in the biological sample the synthetic peptide substrate will be phosphorylated. The amount of phosphorylated substrate can then be correlated to a concentration of DNA in the biological sample. The amount of DNA in the sample would be estimated by comparing the amount of phosphorylated substrate obtained with dilutions of the sample to the amount of phosphorylated substrate obtained with known concentrations of DNA.

By including both a source or preparation of DNA-PK and linear double-stranded DNA in the reaction, the method is configured to detect substances that alter the activity of DNA-PK. The method includes forming a reaction mixture by contacting a sample with a detectably-labeled phosphate donor, a source or preparation of DNA-PK, a source or preparation of linear double-stranded DNA and a synthetic peptide substrate defined by the following features to provide specific recognition and phosphorylation by DNA-PK: (1) a phosphate-accepting amino acid pair which may include serine-glutamine (Ser-Gln) (SQ), threonine glutamine (Thr-Gln) (TQ), glutamine-serine (Gln-Ser) (QS), or glutamine-threonine (Gln-Thr) (QT); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor.

The method of detecting the presence of substances which alter the activity of DNA-PK is identical to the method of detecting DNA-PK except that DNA-PK and linear double-stranded DNA are both added to the reaction mixture. The presence of DNA-PK activity altering substances in the sample can be determined by comparing the amount of phosphorylated substrate obtained in the presence of sample contact to the amount of phosphorylated substrate obtained in control reactions for which sample contact was omitted. Similarly, this method will detect substances which alter the DNA-PK activity by modifying the structure of the linear double-stranded DNA. The result of such modification is detected by an increase or decrease in the catalytic activity of DNA in the DNA-PK mediated phosphorylation reaction.

By prephosphorylating the substrate peptide with DNA-PK, the method is configured to detect the presence in a biological sample of protein phosphatase that removes phosphate from the substrate peptide. The method includes forming a reaction mixture by contacting a biological sample with a phosphorylated synthetic peptide substrate defined by the following features to provide specific recognition by DNA-PK: (1) a phosphorylated amino acid pair which may include phosphoserine-glutamine (PO$_4$•Ser-Gln), phosphothreonine-glutamine (PO$_4$•Thr-Gln), glutamine-phosphoserine (Gln-PO$_4$•Ser), or glutamine-phosphothreonine (Gln-PO$_4$•Thr); (2) enhancer amino acids which may include glutamic acid or glutamine immediately adjacent at the amino- or carboxyl- side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enhancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor.

The method of detecting protein phosphatase, in a biological sample uses synthetic peptide substrates which have been prephosphorylated by DNA-PK. The amount of phosphatase in the sample would be estimated by comparing the amount of phosphorylated substrate remaining after the incubation period to the amount of phosphorylated substrate remaining in control reactions.

A kit for detecting the presence of DNA-PK in a biological sample in accordance with the method of the present invention includes: (1) a detectably-labeled phosphate donor, (2) linear double-stranded DNA, (3) a composition useful in specific detection and quantitation of DNA-PK which comprises a substrate peptide that is phosphorylated by DNA-PK, (4) a negative control peptide of similar composition that is not phosphorylated by DNA-PK, (5) DNA-PK, and (6) a reagent to select or separate the substrate peptide.

Specific synthetic peptide substrates that are phosphorylated by DNA-PK may include: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Asn Asn Val Leu Ser Pro Leu Pro Ser Gln Ala Met Asp Asp Leu Met Lys Lys (SEQ ID NO: 6), Met Ala Ile Tyr Lys Gln Ser Gln His Met Thr Glu Val Val Arg Arg (SEQ ID NO: 7), Glu Pro Pro Leu Ser Gln Glu Thr Phe Ser Asp Leu Trp Lys Lys (SEQ ID NO:. 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Leu Glu Ala Phe Ala Asp Leu Trp Lys Lys (SEQ ID NO: 14), Glu Pro Pro Gln Ser Gln Glu Ala Phe Ala Asp Leu Trp Lys Lys (SEQ ID NO: 15), Glu Pro Pro. Leu Thr Gln Glu Ala Phe Ala Asp Leu Trp Lys Lys (SEQ ID NO: 16), Glu Pro Pro Asp: Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19). The kit may be supplied with or without any or all of the above components, and may also include buffers as appropriate for the intended user, except that it must contain one or more substrate peptides.

In a preferred embodiment the synthetic peptide substrate providing all of the features described above to provide specific recognition and phosphorylation by DNA-PK is a synthetic peptide substrate which is identical to or a variant of the amino acid sequence found at the amino terminus of human or murine p53 tumor suppressor proteins, and which contains either Ser[15] of human p53 tumor suppressor protein or Ser[7] or Ser[18] of murine p53 protein, including the following synthetic peptides: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ. ID NO: 4), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Gln Glu Ala Phe Ala Asp Leu Trp Lys Lys (SEQ ID NO: 15), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18), Pro Glu Ser Gln Glu Ala Phe Ala Asp Leu Trp Lys Lys (SEQ ID NO: 19), Pro Leu Ser Gln Glu Thr Phe Ser Gly Leu Trp Lys Leu Leu Pro Pro-Lys Lys (SEQ ID NO: 63), and Pro Leu Ser Gln Glu Ala Phe Ala Gly Leu Trp Lys Leu Leu Pro Pro-Lys Lys (SEQ ID NO: 64).

In a most preferred embodiment the synthetic peptide substrate providing all of the features described above to provide specific recognition and phosphorylation by DNA-PK is a synthetic peptide substrate which is a variant of the amino acid sequence found at the amino terminus of human p53 tumor suppressor proteins, and which contains Ser[15] of human p53 tumor suppressor protein, including the following peptides: Glu Pro Pro Leu Ser Gln Glu Ala Phe Ala Asp Leu Trp Lys Lys (SEQ ID NO: 11), Glu Pro Pro Gln Ser Gln Glu Ala Phe Ala Asp Leu Trp Lys Lys (SEQ ID NO: 15), Pro Glu Glu Ser Gln Glu Ala Phe Ala Asp Leu Trp. Lys Lys (SEQ ID NO: 18) and Pro Glu Ser Gln Glu Ala Phe Ala Asp Leu Trp Lys Lys (SEQ ID NO: 19).

In particular, in the preferred embodiment, the kit includes, calf thymus DNA or the synthetic oligonucleotide (DA-dC)$_{12}$ (SEQ ID NO: 27), the substrate peptide (SEQ ID NO: 11) or (SEQ ID NO: 18) or (SEQ ID NO: 19), the control peptide (SEQ ID NO: 20) or (SEQ ID NO: 25) or (SEQ ID NO: 23), a concentrated HEPES buffer solution, pH 7.5 containing 250 mM HEPES, pH 7.5, 1 M KCl, 100 mM MgCl$_2$, 1 mM EDTA, 1 mM EGTA, 10 mM DTT, phosphocellulose paper disks, and a set of instructions.

When the above components of the kit are combined in the presence of DNA-PK under the appropriate reaction conditions, the phosphate is transferred from the detectably-labeled phosphate donor to the synthetic peptide substrate. Also included in the kit may be a means for stopping the transfer of the phosphate to the synthetic peptide substrate. Once the transfer of labeled phosphate is stopped, the amount of phosphate transferred from the phosphate donor to, the synthetic peptide substrate is detected. The amount of phosphate transferred to the synthetic peptide substrate is correlated to the concentration of DNA-PK in the biological sample as described in the method of the present invention.

The kit of the present invention has other uses in addition to the detection of DNA-PK activity in biological samples. For example, the kit may be used to detect double-stranded DNA in samples and to estimate the concentration of DNA in such samples, to detect and estimate the concentration of a phosphate donor in samples, to detect and study substances that alter any of these reagents, i.e. DNA-PK, DNA, phosphate donor that would alter the activity of DNA-PK, and to detect and study enzymes that remove phosphate from the substrate peptide. In particular, by including a source or preparation of DNA-PK and omitting a source or preparation of DNA in the reaction mixture, the kit may be used to detect DNA in a biological sample. The amount of DNA in the sample would be estimated by comparing the amount of phosphorylated substrate obtained with dilutions of the sample to the amount of phosphorylated substrate obtained with known concentrations of DNA. By including both a source or preparation of DNA-PK and DNA in a reaction mixture, the kit may be used to detect substances that alter the activity of DNA-PK. By prephosphorylating the substrate peptide with DNA-PK and including the phosphorylated peptide in a reaction mixture in the absence of a source or preparation of DNA-PK, the kit may be used to detect protein phosphatases that remove phosphate from the substrate peptide.

The linear double-stranded DNA utilized in the present invention may be DNA from the following list: plasmid DNA, viral DNA, bacteriophage DNA, calf thymus DNA, salmon testes DNA, salmon sperm DNA, herring sperm DNA, herring testes DNA, *Escherichia coli* DNA, *Micrococcus tysodeikticus* DNA, *Clostidium perfrigens* DNA, *Clostridium welchii* DNA, human placenta DNA, synthetically prepared double-stranded DNA fragments, and sources of DNA including chromatin, viruses, cell nuclei and mixtures thereof. The synthetic double-stranded oligonucleotides may be (dG-dC)$_n$ and (dC-DG)$_n$, where n is equal to 7 to 15 (i.e. (GCGC)$_n$ or (CGCG)$_n$) and where the total length is 14 to 30 base pairs. Other synthetic oligonucleotides or DNAs that are not completely double stranded also may be used, for example, circular DNAs with gaps or bubbles, and linear DNAs with single stranded tails. It has been suggested that DNA-PK may have a physical requirement for a DNA end or free 5' nucleotide to become activated in vitro (Anderson and Lees-Miller, 1992, *Crit. Rev. in Eukaryotic Gene Expression*, 2:283–314). Therefore, the above list of DNAs is not exhaustive, but merely representative, as virtually any DNA can be: manipulated to provide such an end or free 5' nucleotide and therefore function in the present invention.

The detectably-labeled phosphate donor found in the kit of the present invention may be [$^{32}$P]-ATP, [$^{32}$P]-dATP, [$^{33}$P]-ATP and [$^{33}$P]-dATP. In a particularly preferred embodiment the labeled phosphate donor is [$^{32}$P]-ATP labeled in the gamma position.

In addition, compositions useful in specific detection and quantitation of DNA-PK which comprise synthetic peptide substrates for use in the present method and kit are provided. The synthetic peptide substrates are defined by the following features to provide specific recognition and phosphorylation by DNA-PK: (1) a phosphate-accepting amino acid pair which may include serine-glutamine (Ser-Gln) (SQ), threonine-glutamine (Thr-Gln) (TQ), glutamine-serine (Gln-Ser) (QS), or glutamine-threonine (Gin-Thr) (QT); (2) enhancer amino acids which may include glutamic acid or glutamine immediately adjacent at the amino- or carboxyl-side of the amino acid pair and forming an amino acid pair-enhancer unit; (3) a first spacer sequence at the amino terminus of the amino acid pair-enhancer unit; (4) a second spacer sequence at the carboxyl terminus of the amino acid pair-enchancer unit, which spacer sequences may include any combination of amino acids that does not provide a phosphorylation site consensus sequence motif; and (5) a tag moiety, which may be an amino acid sequence or another chemical entity that permits separating the synthetic peptide from the phosphate donor. Synthetic peptide substrates providing some or all of these features include: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO:, 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Asn Asn Val Leu Ser Pro Leu Pro Ser Gln Ala Met Asp Asp Leu Met Lys Lys (SEQ ID NO: 6), Met Ala Ile Tyr Lys Gln Ser Gln His Met Thr Glu Val Val Arg Arg (SEQ ID NO: 7), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Leu Glu Ala Phe Ala Asp Leu Trp Lys Lys (SEQ ID NO: 14), Glu Pro Pro Gln Ser Gln Glu Ala Phe Ala Asp Leu Trp Lys Lys (SEQ ID NO: 15), Glu Pro Pro Leu Thr Gln Glu Ala Phe Ala Asp Leu Trp Lys Lys (SEQ ID NO: 16), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

In a preferred embodiment the synthetic peptide substrate is selected from the following synthetic peptides: Met Glu Glu Pro Gln Ser Asp Pro Ser Val Glu Pro Pro Leu Ser Gln Glu Thr Phe Ser Asp Leu Trp Lys Leu Leu Pro Glu (SEQ ID NO: 1), Met Glu Glu Ser Gln Ser Asp Ile Ser Leu Glu Leu Pro Leu Ser Gln Glu Thr Phe Ser Gly Leu Trp Lys Leu Leu Pro Pro (SEQ ID NO: 2), Met Glu Glu Ser Gln Ser Asp Ile Ser Leu Glu Leu Pro Tyr Lys Lys (SEQ ID NO: 3), Met Glu Glu Pro Gln Ser Asp Pro Ser Val Glu Pro Pro Leu Ser Gln Glu Thr Phe Ser Asp Leu Trp Lys Lys (SEQ ID NO: 4), Glu Pro Pro Leu Ser Gln Glu Thr Phe Ser Asp Leu Trp Lys Lys (SEQ ID NO: 8), Glu Pro Pro Leu Ser Gln Glu Ala Phe Ala Asp Leu Trp Lys Lys (SEQ ID NO: 11), Glu Pro Pro Leu Ser Gln Glu Ala Phe Ala Asp Leu Leu Lys Lys (SEQ ID NO: 12), Glu Pro Pro Gln Ser Gln Glu Ala Phe Ala Asp Leu Trp Lys Lys (SEQ ID NO: 15), Glu Pro Pro Asp Ser Gln Glu Ala Phe Ala Asp Leu Trp Lys Lys (SEQ ID NO: 17), Pro Glu Glu Ser Gln Glu Ala Phe Ala Asp Leu Trp Lys Lys (SEQ ID NO: 18), Pro Glu Ser Gln Glu Ala Phe Ala Asp Leu Trp Lys Lys (SEQ ID NO: 19), Pro Leu Ser Gln Glu Thr Phe Ser Gly Leu Trp Lys Leu Leu Pro Pro-Lys Lys (SEQ ID NO: 63), and Pro Leu Ser Gln Glu Ala Phe Ala Gly Leu Trp Lys Leu Leu Pro Pro-Lys Lys (SEQ ID NO: 64).

In a most preferred embodiment the synthetic peptide substrate is selected from the following peptides: Glu Pro Pro Leu Ser Gln Glu Ala Phe Ala Asp Leu Trp Lys Lys (SEQ. ID NO: 11), Glu Pro Pro Gln Ser Gln Glu Ala Phe Ala Asp Leu Trp Lys Lys (SEQ ID NO: 15), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

The method of the present invention can be used to detect the presence of DNA-PK activity in a biological sample. The biological sample may be any eukaryotic cell extract. For example, the cell extract may be prepared from human tissue culture cell lines such as HeLa cells or 293 cells. In addition, rabbit reticulocytes, Sf9 cells, and the eggs and oocytes of frogs (Xenopus), sea urchins (Arbacia), and clams (Spisula), may also be used. Other biological samples may include extracts of primary tumors, red blood cells, any other eukaryotic cell type and eukaryotic and prokaryotic cells which have been engineered to express DNA-PK.

The DNA-PK may be secreted from the prokaryotic cell or may be found internally in vesicles within the bacterial cell. Similarly, the eukaryotic cells may also secrete DNA-PK or it may be found internally inside the cell. In each of these cases either a cell-free supernatant or cell lysate may be used to assay for DNA-PK activity. The synthetic substrate peptides of the present invention may also be used to detect DNA-PK activity in vivo if the peptide is delivered to the interior of the cell by microinjection or by similar means, or in cells permeabilized to permit entry of the peptide into the cell.

In another embodiment of the present invention, the activity of a protein kinase such as DNA-PK is monitored in living cells. The monitoring of protein kinase activity, such as DNA-PK activity is partially accomplished by introducing to the cells expression vectors containing genes encoding recombinant (artificial) protein substrates. The protein substrates are expressed at moderate levels and are efficiently and specifically phosphorylated when a protein kinase such as DNA-PK is activated.

The typical artificial protein substrate, encoded by a recombinant gene of the present invention, consists of four functional elements, and two additional elements to facilitate analysis of the substrate in vivo and in vitro. The four functional components of these protein substrates are: (1) a protein segment containing a phosphorylation site consensus sequence motif for phosphorylation by a protein kinase or DNA-PK: (2) an optional nuclear localization signal; (3) an optional: DNA-binding domain; and (4) an epitope that can be detected with high sensitivity after fractionation of cell extracts by polyacrylamide gel electrophoresis. The nuclear localization signal is believed to be required when the activity of nuclear kinases, such as DNA-PK, is being monitored. The DNA-binding domain is also believed to be required when the activity of DNA-PK is being monitored. The nuclear localization signal and DNA-binding domain may be omitted when monitoring protein kinases other than DNA-PK.

As previously described, the protein substrates encoded by the recombinant genes may also include two additional facilitating elements. These additional facilitating elements of the protein substrates are: (1) an epitope for affinity purification of the substrate; and (2) a site that permits cleavage (excision) of the segment of the protein substrate containing the phosphorylation site.

The expression vectors of the present invention are originally assembled in a host cell which does allow expression of the protein substrate. This is accomplished utilizing standard techniques known in the art. A suitable host for assembly of the expression vectors include E. coli strain BL21(DE3) (Novagen, 597 Science Drive, Madison, Wis. 53711) and equivalents. Once assembled, the expression vectors are isolated from the host and can be introduced into other living cells. Once the expression vector is transferred, the modified cells can then be tested for expression of DNA-PK or other protein kinase activity.

After expression of the protein substrate, the amount of phosphorylated protein substrate is determined. The phosphorylated and non-phosphorylated protein substrates can be distinguished utilizing the techniques described previously for detecting the transfer of non-radioactive phosphate to a peptide substrate.

One preferred technique, which does not require radiolabeling of the phosphate or phosphoprotein, is to use isoelectrofocusing (IEF) polyacrylamide gel electrophoresis to separate the protein components of cell extracts which have been prepared in the presence of phosphatase and kinase inhibitors. Isoelectrofocusing separates proteins of different net charges. Accordingly, a phosphorylated protein which has a greater negative charge due to the added phosphate groups can be easily separated from its unphosphorylated protein counterpart. The proteins in the gel are then transferred from the gel to a membrane (e.g. nitrocellulose or polyvinylidene difluoride, PVDF) where the position(s) of the protein of interest is detected using an antibody that reacts with it.

If desired the position of the phosphorylated and non-phosphorylated substrates can be confirmed with radioactive precursors such as $^{32}PO_4$. This is accomplished by labeling the living cells with $^{32}PO_4$ prior to fractionation. The protein substrate can also be phosphorylated in vitro with $^{32}PO_4$. In either situation, after separation of the protein substrate and transfer to a membrane, the membrane is developed using autoradiographic procedures.

The protein substrate can also be partially purified utilizing the epitope tags for affinity purification if necessary. This is done if an insufficient amount of protein substrate required for easy detection is expressed in the cells, or if removal of proteins other than the protein substrate is desired. In a preferred embodiment, the epitope is a sequence of amino acids which allow immobilized metal affinity purification. In a most preferred embodiment, six consecutive histidine (His) residues are inserted after the N-terminal phosphorylation site segment to provide the epitope. This allows purification with immobilized metals such as Nickel (Ni) or Zinc (Zn).

The determination of the amount of phosphorylated protein substrate is correlated to the concentration of either protein kinase or DNA-PK activity; any of the methods described previously for determining activity are applicable.

Figure 4:
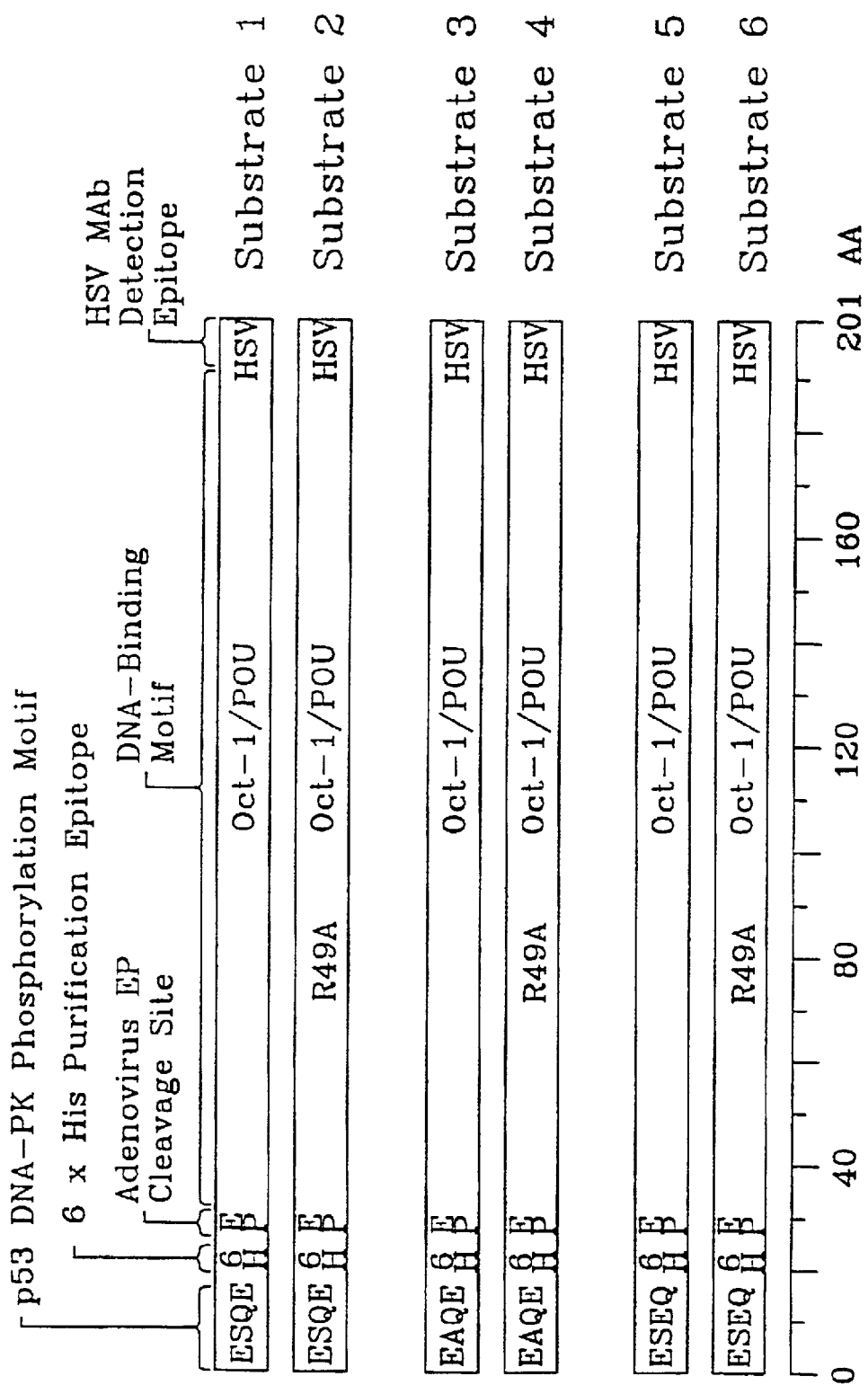
FIG. 4 is a schematic representation of six recombinant (artificial) DNA-PK substrates partially derived from human tumor suppressor gene product p53.

In a preferred embodiment of the method of monitoring DNA-PK activity in a cell, recombinant DNA encoding the protein substrates 1 and 4 shown in FIG. 4, is utilized. The recombinant gene encoding protein substrate 1 is most preferred. The insertion of one of these prototype recombinant genes in an appropriate expression vector system, e.g.

the T7-derived plasmid expression vector, pET28 enables the encoded proteins to be efficiently produced in *Echerichia coli*.

All six protein substrates shown in FIG. 4 contain the following elements: (1) a phosphorylation site concensus sequence motif for DNA-PK; (2) a DNA-binding domain; (3) a detection epitope tag; (4) an epitope of six consecutive histidine residues for immobilized metal-affinity purification; and (5) a consensus cleavage site located after the histidine tag.

The phosphorylation site for DNA-PK is contained within the sequence Met Pro Glu Glu Ser Gln Glu Thr Phe Glu Asp Leu Trp Lys Leu Leu Pro (SEQ ID NO: 40) in which serine residue 5 is phosphorylated by DNA-PK in vitro. This sequence is comprised of the first four residues of human hsp90, Met Pro Glu Glu (SEQ ID NO: 41), and a variant of residues 15 to 27 of human p53, Ser Gln Glu Thr Phe Ser Asp Leu Trp Lys Leu Leu Pro (SEQ ID NO: 42). The substitution of glutamic acid (Glu) for the second serine (Ser) at the position of serine in human p53 allowed the introduction of a Bgl II restriction endonuclease cloning site in the substrate gene which facilitates the construction of genes with different phosphorylation sites. With a few exceptions, (SEQ ID NO: 40) is also identical to the synthetic peptide substrate Pro Glu Glu Ser Gln Glu Ala Phe Ala Asp Leu Trp Lys Lys (SEQ ID NO: 18). First, the synthetic peptide substrate lacks the amino-terminal methionine (Met) which is expected to be removed in vivo (Lees-Miller, et al., 1989, *J. Biol. Chem.*, 264:17275–17280). Second, threonine (Thr) at the position of threonine, 18 of human p53 protein and serine (Ser) at the position of serine 20 of human p53 protein are replaced by alanine in the synthetic peptide substrate (SEQ ID NO: 18).

The DNA-binding domain is the wild-type human POU domain (residues $Glu^{280}$-$Pro^{439}$) of the human Oct-1 transcription factor (Genbank accession no. X13403 (HSOCT1), human mRNA for octamer-binding protein Oct-1, 2584 bp). Sequences within this domain also act as nuclear localization signals. A mutant POU domain which lacks a natural protein kinase A (PKA) site at $Ser^{285}$ in the human Oct-1 protein also may be used.

The detection epitope tag is the sequence Glu Pro Glu Leu Ala Pro Glu Asp Pro Glu Asp (SEQ ID NO: 43), which corresponds to a segment (residues 289–299) from the Herpes simplex virus 1 glycoprotein D precursor, and is derived from the Novagen pET-25b vector.

A series of six consecutive histidines are inserted after the N-terminal phosphorylation site segment to provide an epitope for immobilized metal-affinity purification. Thus, partial purification of the expressed protein substrate can be accomplished through the utilization of this tag.

Finally, a consensus cleavage site Met Ser Gly Gly (SEQ ID NO: 44) for the human adenovirus endoproteinase (C. W. Anderson, 1993, *Protein Express. Purif.*: 4:8–15) is located after the histidine tag.

The predicted primary sequence of the most preferred protein substrate, the wild-type artificial substrate (substrate 1 in FIG. 4) is shown in FIG. 8B.

The kit to monitor protein kinase or DNA-PK activity within a cell includes the expression vector described in the method of the invention. Accordingly, the appropriate protein substrate encoding gene is incorporated into the expression vector to provide the desired phosphorylation site consensus sequence motif for either the protein kinase or DNA-PK. With the kit for monitoring DNA-PK activity, an agent that nicks or otherwise damages DNA may also be included to provide short DNA segments to activate DNA-PK within the cell. Purified samples of the protein substrates, and their phosphorylated counterparts, may also be included as controls. An appropriate reagent to determine the amount of phosphorylated peptide substrate following expression in the cell may also be included in the kit. Such reagents may include: (1) monoclonal antibodies to detect the substrate tag; (2) sources or preparations of DNA-PK and DNA; (3) materials for polyacrylamide gel electrophoresis and/or IEF gel electrophoresis; and (4) materials for blotting the protein substrate on nitrocellulose and PVDF membranes.

The method for identifying agents that alter either intracellular protein kinase or intracellular DNA-PK activity is identical to the method of monitoring activity except for an additional step. The cells are contacted with agents that may alter protein kinase or DNA-PK activity. This procedure is basically the same as in the method for detecting substances that alter the activity of DNA-PK in vitro. In a second embodiment of the method, cells may be treated with an agent that activates the protein kinase or DNA-PK, then the cells are contacted, either before or after, with an agent that may inhibit activation of the protein kinase or DNA-PK. The amount of phosphorylated substrate in the treated cells is then compared to the amount of phosphorylated substrate in control (i.e., non-contacted) cells, containing the protein substrates.

The monitoring of intracellular protein kinase activity and DNA-PK activity is also accomplished through the expression of a reporter gene product in a transfected or transformed cell. This is partially accomplished by introducing into a living cell an expression vector, such as those previously described, with one modification. The expression vector will contain a gene coding for a phosphorylated protein substrate capable of activating the transcription of a reporter gene. By determining the amount of reporter gene product expressed, a correlation to the concentration of protein kinase or DNA-PK activity can be accomplished. Alternatively, the expression of the reporter gene product can be used in a qualitative manner to determine if protein kinase or DNA-PK activity exists.

As previously described, the phosphorylation of the protein substrate activates the expression of the reporter gene product whose synthesis and activity can be determined or for which a qualitative selection mechanism is available (e.g. confers antibiotic resistance). Common reporter genes are β-galactosidase, luciferase, the gene for neomycin resistance, or the DHFR gene for MTX resistance.

The protein substrate for this embodiment of the present invention has the following elements to facilitate transcription of the reporter gene: (1) a transactivation domain which contains a phosphorylation site consensus sequence motif specific for either a protein kinase or DNA-PK; and (2) a DNA binding domain. The activation of the transactivation domain by phosphorylation thereby activates the transcription of the reporter gene.

As known in the art, the activation of transactivation domain can be accomplished directly or indirectly via phosphorylation. In the preferred embodiment of the present invention, activation of the transactivation domain is achieved indirectly via phosphorylation. In the most preferred embodiment of the present invention, indirect activation of the transactivation domain is achieved via phosphorylation by DNA-PK.

The most preferred protein substrate for DNA-PK phosphorylation includes as the transactivation domain residues 1–73 of p53 and as the DNA binding domain residues 1–147 of gal4. This embodiment of the invention is based on the assumption that phosphorylation of the DNA-PK site in the transactivation domain of the human p53 protein regulates its interaction with the Hmd2 protein. Hmd2 is the product of a cellular proto-oncogene that has been shown to regulate (i.e., inactivate) the transcriptional activity of p53 by binding to a site near the amino terminus of p53. The Hmd2 binding site is located adjacent to the serine 15 phosphorylation site for DNA-PK (Chen et al., 1994, *Proc. Natl. Acad. Sci. USA*, 91;2684–2688; Haines et al., 1994, *Mol. Cell. Biol.*, 14:1171–1178; Lin et al., 1994, *Genes Dev.*, 8:1235–1246; Momand et al., 1992, *Cell*, 69:1237–1245; Oliner et al., 1993, *Nature*, 362:857–860; Wu et al., 1992, *Genes Dev.*, 7:1126–1132; D. Lane, personal communication).

As known in the art, the phosphorylation of human p53 at amino terminal serines including serine 15 by DNA-PK is believed to inhibit Hmd2 binding to p53, thereby activating p53-mediated transcription. Similarly, it is believed that the activation of transcription of a reporter gene can be achieved with the artificial recombinant transcription factor of the present invention, which includes the transactivation region of p53, residues 1–73 of human p53 (Unger et al., 1992, *EMBO J.*, 11:1383–1390; A. J. Levine, 1993, *Ann. Rev. Biochem.*, 62:623–651), attached to an appropriate DNA-binding domain, e.g. residues 1–147 of the yeast gal4 protein.

In cells that overexpress Hmd2, whether naturally or through genetic engineering, the artificial recombinant transcription factor will remain inactive because of its complex formation with Hmd2. Upon activation of DNA-PK and other protein kinases, the recombinant transcription factor will be phosphorylated and activated, which, in turn, will activate transcription of the reporter gene.

As will be apparent to one skilled in the art, variations of the most preferred embodiment are possible. However, the protein substrate must efficiently bind Hmd2 (or an equivalent factor) and phosphorylation of the protein substrate must inhibit this interaction.

In a second embodiment of this method, the activation of the transactivation domain is achieved directly via phosphorylation of the protein substrate. The direct activation of the protein substrate provides a simpler mechanism for transcription of the reporter gene since an inhibiting protein, such as Hmd2, is not present.

The preferred protein substrate for this embodiment contains the residues of the protein c-Jun, which is found in eukaryotic cells. C-Jun is composed of two functional domains, a DNA-binding domain located near its carboxyl-terminus and a transactivation domain near its amino terminus (Angel, et al., 1989, *New Biol.*, 1:35–43; Bohmann, et al., 1989, *Cell*, 59:709–711; Smeal, et al., 1989, *Genes & Dev.*, 3:2091–2100). It has been found that the phosphorylation of serine 63 and serine 73 in the amino-terminal activation domain of the protein c-Jun potentiates its transactivation function (Hibi, et al., 1993, *Genes & Dev.*, 7:2135–2148). Accordingly, expression vectors containing the protooncogene c-Jun, or a modified version thereof, can be constructed and utilized in accordance with the present invention. For example, the sequence of the c-Jun transactivation region would be modified around the serine 63 and 73 sites to make these sites specific for DNA-PK.

EXAMPLES

The following examples are provided to further illustrate the present invention. Examples 1–8, are provided to illustrate protocols useful in the preparation of the materials needed for the present invention. Examples 9–14 specifically illustrate preferred embodiments and methods of using the present invention. Examples 15–17 illustrate the preferred additional embodiments of the present invention utilizing expression vectors which encode the recombinant protein substrates for DNA-PK.

Example 1

Preparation of Cell Extracts

Those skilled in the art recognize that many methods exist to prepare cell extracts and cell free supernatants. The method used will depend upon the source of the starting material. For example, if eukaryotic tissue culture cells are used they are grown in an appropriate nutrient medium. Cells are usually grown to a concentration of approximately 0.7 to $1 \times 10^6$ cells per milliliter, however, optimal concentrations will vary according to the cell line employed as well as other parameters known in the art. Furthermore, the health and viability of the cells is more important than cell density.

Once the cell cultures are ready to be harvested, cell extracts can be prepared by any of several methods known to those skilled in the art in order to provide a solution containing DNA-PK. In particular, cytoplasmic extracts of HeLa and mouse cells can be prepared from cells grown in suspension culture to approximately $5 \times 10^5$ cells/ml. Cells are harvested by centrifugation at 4° C. After three washes in ice-cold phosphate buffered saline (PBS), the cell pellet is resuspended in one packed cell volume of ice-cold low salt buffer (LSB: 25 mM KCl, 10 mM NaCl, 1.1 mM $MgCl_2$, 0.1 mM EDTA, 10 mM HEPES, pH 7.2 with KOH at 20° C.), and allowed to swell for 10 min. Cells are broken by approximately strokes in a tight fitting stainless steel homogenizer (Wheaton Instruments, Millville, N.J.).

An S10 supernatant was prepared from the homogenate by centrifugation at 10,000 g for 30 min at 4° C. Supernatants were stored frozen in liquid nitrogen in small aliquots. Typical extracts may have an absorbance at 260 nm of between 50 and 100. To prepare extracts from small numbers of cells (e.g., approximately $5 \times 10^6 – 5 \times 10^7$) the homogenization step was replaced by a single freeze-thaw cycle. Other cell types were also prepared in a similar fashion. For example, rabbit reticulocyte lysates can be prepared as described by Jackson, et al., in *Methods Enzymol.*, 96:50–74 (1983). Extracts of Arbacia eggs can be prepared as described by Ballinger, et al., in *Dev. Biol.*, 101:192–200 (1984).

Example 2

Preparation of DNA-PK, Mouse p53, hsp 90 and Olignucleotides

DNA-PK was purified from HeLa cells as described previously by Lees-Miller, et al., *Mol. Cell. Biol.*, 10:6472–6481 (1990) and as modified in Lees-Miller, et al., *Mol. Cell. Biol.*, 12:5041–5049 (1992). In particular, extracts of HeLa S3 cells were prepared by a single freeze-thaw cycle of a cell suspension as described in Example 1 and reported by Lees-Miller, et al., *J. Biol. Chem.*, 264:2431–2437 (1989). Phenylmethylsulfonyl fluoride was added to the S10 (10,000×g) supernatant as a powder to 0.5 mM. DNA-PK activity was found in the 100,000×g (ribosomal) pellet. DNA-PK preparations typically were made from 200 ml of S10 supernatant that had been derived from approximately $10^{10}$ cells. All steps were performed at 4° C. unless indicated otherwise.

The S100 ribosomal pellet containing DNA-PK activity was solubilized by sonicating twice for 5 seconds each time in the water-cooled horn of a Branson Sonifier (Branson Sonic Power Co., Danbury, Conn.) in 40 ml of 25' mM N-2-hydroxyethyl-piperazine-N'-2-ethanesulfonic acid (HEPES)-0.2 mM EDTA-0.5 mM dithiothreitol (pH 7.5) (HEPES buffer) containing 0.5 M KCl and 10 mM $MgCl_2$. After recentrifugation at 100,000×g for 60 min, the ribosomal salt wash can be stored frozen at −70° C. The salt wash was diluted with HEPES buffer to give a KCl concentration of 0.1 M, centrifuged for 15 min at 10,000×g to remove precipitates, and applied to a column (2.5 by 5 cm) of DEAE-Sepharose CL6B (Sigma Chemical Co., St. Louis, Mo.) equilibrated in HEPES buffer containing 0.1 M KCl. After being washed, the column was eluted with HEPES buffer containing 0.5 M KCl. This eluate was dialyzed for 1 hour against 10 volumes of HEPES buffer containing 50 mM KCl and adjusted to 0.1 M KCl before application to a column (1.5 by 4 cm) of dsDNA-cellulose (Sigma Chemical Co., St. Louis, Mo.) equilibrated in HEPES buffer with 0.1 M KCl. The fraction containing DNA-PK activity was eluted from dsDNA-cellulose with either a step of 0.5 M KCl or a 30-ml linear gradient from 0.1 to 0.5 M KCl in HEPES buffer. The fraction containing DNA-PK activity eluted from dsDNA-cellulose at a KCl concentration of between 0.2 and 0.4 M KCl. Active fractions containing DNA-PK were pooled, aliquoted, and stored at −70° C. At this step, the fraction containing DNA-PK activity was stable for several months, and aliquots could be frozen and thawed numerous times.

Active fractions containing DNA-PK were further purified by chromatography on DEAE-Sepharose in the presence of 25 mM $MgCl_2$, on single-stranded DNA (ssDNA)-cellulose, on Mono S Fast Flow (Pharmacia-LKB Biotechnology, Piscataway, N.J.), on phosphocellulose (Sigma Chemical Co., St. Louis, Mo.), on heparin-Sepharose (Sigma Chemical Co., St. Louis, Mo.) or on ATP-agarose type 4 (Pharmacia-LKB Biotechnology, Piscataway, N.J.). The first three procedures were used to show that hsp90, SV40 TAg, and p53 were phosphorylated by the same activity. The dsDNA-cellulose eluate was adjusted to 0.1 M KCl by a brief dialysis as described above, $MgCl_2$ was added to 25 mM, and the extract was applied to a column (2.5 by 4 cm) of DEAE-Sepharose CL-6B (Sigma Chemical Co., St. Louis, Mo.) equilibrated in 0.1 M KCl-HEPES buffer containing 25 mM $MgCl_2$. Under these conditions, DNA-PK activity did not bind to the column, and the flow through containing DNA-PK was applied directly to a column (1.5 by 4 cm) of ssDNA-cellulose equilibrated in HEPES a buffer containing 0.1 M KCl. DNA-PK activity was eluted with a 16-ml linear gradient from 0.1 to 0.5 M in KCl at a flow rate of 0.5 ml/min. Active fractions containing DNA-PK were pooled, dialyzed for 1 h, and applied to a column (1 by 1 cm) of Mono S Fast Flow. This column was eluted with a 10-ml linear gradient of 0.1 to 0.3 M KCl in HEPES buffer. Active fractions containing DNA-PK were again pooled and then concentrated by using a Centricon 30 unit (Amicon Corporation, Lexington, Mass.).

DNA-PK preparations purified from human tissue culture cells through dsDNA-cellulose have a specific activity of approximately 3 to 6 U/mg of protein; approximately 6 mg of protein (Bio-Rad assay) is obtained from $10^{10}$ cells. DNA-PK purified through phosphocellulose or Mono S Fast Flow has a specific activity of up to 200 U/mg, and protein yield was about 5 $\mu$g per $10^{10}$ cells. A unit of activity is defined as 1 nmol of phosphate transferred to hsp90 per min at 30° C. under the assay conditions described in Example 4. Highly purified DNA-PK loses activity when stored on ice or frozen at −70° C.

In current procedures the gradient elution from Q-Sepharose Fast Flow described above was substituted for DEAE-Sepharose chromatography. In addition, the gradient elution from S-Sepharose Fast Flow (Pharmacia-LKB Biotechnology, Piscataway, N.J.) described above was substituted for double-stranded DNA-cellulose chromatography. The present procedure achieved a similar DNA-PK specific activity as described above but yielded more activity per cell.

Wild-type mouse p53 was purified by immunoaffinity chromatography from Sf9 insect cells infected with the recombinant virus NPVp53 (Stenger, et al. 1992, Mol. Carcinog., 5:102–106). Human hsp90 was purified, as reported by Lees-Miller, et al., J. Biol. Chem., 264:2431–2437 (1989). Alternating $(dG-dC)_n$ oligonucleotides of defined length were synthesized on a Milligen/Biosearch 8750 oligonucleotide synthesizer and purified by using an RP-1 cartridge (Glen Research, Co., Sterling, Va.); before use, the oligonucleotides were dissolved at 1 mg/ml in 10 mM Tris-HCl (pH-8)-1 mM EDTA-50 mM NaCl, heated briefly at 100° C., and allowed to cool slowly overnight (Lees-Miller, et al., 1992, Mol. Cel. Biol., 12:5041–5049).

Example 3

Preparation of Synthetic Peptides

It was previously demonstrated that two sites of the heat shock protein hsp90 and four sites of the SV40 TAg protein could be phosphorylated in vitro by DNA-PK (Lees-Miller, et al., 1989, J. Biol. Chem., 264:17275–17280, and Chen, et al., 1991, J. Virol. 10:5131–5140). Each phosphorylation site was a threonine or serine residue that was immediately followed by a glutamine residue, suggesting Ser-Glu (SQ) or Thr-Glu (TQ) was required for in vitro phosphorylation by DNA-PK. It was suggested that SQ and TQ might represent the phosphorylation site consensus sequence motif for DNA-PK. The following experimental work was undertaken to determine the accuracy of that suggestion and to determine the other structural requirements for synthetic peptides that were substrates for DNA-PK that provided high specificity and excellent kinetic properties.

Wild-type human p53 has six serines (but no threonines) that are immediately preceded or followed by glutamine: serines 6 (Gln-Ser-Asp), 15 (Leu-Ser-Gln), 37 (Pro-Ser-Gln), 99 (Pro-Ser-Gln), 166 (Gln-Ser-Gln); and 376 (Gln-Ser-Thr) (Lees-Miller, et al., 1992, Mol. Cell. Biol., 12:5041–5049). To determine whether these sites could be phosphorylated by DNA-PK, peptides were synthesized corresponding to sequences surrounding these serines, (SEQ ID NO: 4), (SEQ ID NO: 6), (SEQ ID NO: 28), (SEQ ID NO: 7), and (SEQ ID NO: 30) (see Table 1). In addition, peptides were synthesized that contained the $p34^{cdc2}$ kinase site at serine 312 (SEQ ID NO: 29) and that contained the casein kinase II site, at serine 392 (SEQ ID NO: 31). Additional synthetic peptides which were tested for use as DNA-PK-specific substrates are listed in Table 1. For most peptides that had fewer than two arginine or lysine residues, one or two lysines were added at the carboxyl terminus to facilitate peptide binding to phosphocellulose paper (Glass, et al., 1978, *Anal. Biochem.*, 87:566–575).

Protected peptide chains were assembled by the stepwise solid-phase method, using a 430A Automated Peptide Synthesizer (Applied Biosystems Inc., Foster City, Calif.). After removal of the N-tert-butoxycarbonyl (tBoc) group with trifluoroacetic acid, cleavage of the peptide from the resin and removal of side chain protecting groups were accomplished with HF in the presence of p-cresol. The crude peptide was extracted with 5% acetic acid and chromatographed on Sephadex G-25 (Sigma Chemical Co., St. Louis, Mo.). Further purification was by reverse-phase high-pressure liquid chromatography (HPLC) on a Vydac $C_4$ column (The Nest Group, Southboro, Mass.) in 0.05% trifluoroacetic acid-water-acetonitrile.

(SEQ ID NO: 12) (Table 1) and the synthetic casein kinase I substrate Asp Asp Asp Glu Glu Ser Ile Thr Arg Arg (SEQ ID NO: 35), described by Agostinis, et al., *FEBS Lett.*, 259:75–78 (1989) were obtained from (Multiple Peptide Systems, Inc, San Diego, Calif.). The S6 kinase substrate Arg Arg Leu Ser Ser Leu Arg Ala (SEQ ID NO: 36) was purchased from (Bachem California, Inc., Torrance, Calif.); the casein kinase II substrate Arg Arg Arg Glu Glu Glu Thr Glu Glu Glu (SEQ ID NO: 37) was provided by E. Krebs, University of Washington, Seattle. The purity of each peptide, as judged from its reverse-phase HPLC profile, was greater than 95%. Purified peptides were dissolved in water and stored at −20° C. Peptide concentrations were determined by quantitative amino acid analysis after hydrolysis for 24 h at 1050° C. in 6 N HCl. Each peptide was tested as a potential DNA-PK substrate.

TABLE 1

Synthetic p53 Peptide Substrates

| SEQ NO NO: | p53 residues[a] | Peptide Sequence[b] | $K_m$ ($\mu$M) | $V_{max}$ (pmol/min/$\mu$g of DNA-PK) | $PO_4$ incorp. (pmol/min/$\mu$g of DNA-PK)[c] |
|---|---|---|---|---|---|
| 1 | 1–28 | Met Glu Glu Pro Gln Ser Asp Pro Ser Val Glu Pro Pro Leu Ser Gln Glu Thr Phe Ser Asp Leu Trp Lys Leu Leu Pro Glu | ND[d] | ND | ND |
| 2 | 4–31 | Met Glu Glu Ser Gln Ser Asp Ile Ser Leu Glu Leu Pro Leu Ser Gln Glu Thr Phe Ser Gly Leu Trp Lys Leu Leu Pro Pro | ND* | ND* | ND* |
| 3 | 4–13 | Met Glu Glu Ser Gln Ser Asp Ile Ser Leu Glu Leu Pro—Tyr Lys Lys | 650 | 390 | 94 |
| 4 | 1–24 | Met Glu Glu Pro Gln Ser Asp Pro Ser Val Glu Pro Pro Leu Ser Gln Glu Thr Phe Ser Asp Leu Trp Lys—Lys | 210 | 90 | 44 |
| 5 | 1–24 | Met Glu Glu Pro Gln Ser Asp Pro Ser Val Glu Pro Pro Leu <u>Ala</u> Gln Glu Thr Phe Ser Asp Leu Trp Lys—Lys | —[f] | — | 5.3 |
| 6 | 29–44 | Asn Asn Val Leu Ser Pro Leu Pro Ser Gln Ala Met Asp Asp Leu Met—Lys Lys | 470 | 470 | 102 |
| 28 | 92–108 | Pro Leu Ser Ser Ser Val Pro Ser Gln Lys Thr Tyr Gln Gly Ser Tyr Gly Lys Lys | — | — | 3 |
| 7 | 160–175 | Met Ala Ile Tyr Lys Gln Ser Gln His Met Thr Glu Val Val Arg Arg | 740 | 200 | 44 |
| 29 | 306–327 | Ala Leu Pro Asn Asn Thr Ser Ser Ser Pro Gln Pro Lys Lys Lys Pro Leu Asp Gly Glu Tyr | — | — | 0.6 |
| 30 | 371–385 | Ser Lys Lys Gly Gln Ser Thr Ser Arg His Lys Lys Leu Met Phe | — | — | 0 |
| 31 | 380–393 | His Lys Lys Leu Met Phe Lys Thr Glu Gly Pro Asp Ser Asp | — | — | 0 |
| 8 | 11–24 | Glu Pro Pro Leu Ser Gln Glu Thr Phe Ser Asp Leu Trp Lys—Lys | 350 | 360 | 130 |
| 9 | 11–19 | Glu Pro Pro Leu Ser Gln Glu Thr Phe—Lys Lys | ND | ND | 15 |
| 10 | 11–20 | Glu Pro Pro Leu Ser Gln Glu Thr Phe Ser Asp—Lys Lys | ND | ND | 12 |
| 11 | 11–24[e] | Glu Pro Pro Leu Ser Gln Glu <u>Ala</u> Phe <u>Ala</u> Asp Leu Trp Lys—Lys | 760 | 380 | 83 |
| 12 | 11–24[e] | Glu Pro Pro Leu Ser Gln Glu <u>Ala</u> Phe <u>Ala</u> Asp Leu Leu Lys—Lys | 560 | 160 | 36 |
| 32 | 11–24[e] | Glu Pro Pro Leu Ser <u>Glu</u> Glu <u>Ala</u> Phe <u>Ala</u> Asp Leu Trp Lys—Lys | ND | ND | 0.4 |
| 33 | 11–24[e] | Glu Pro Pro Leu Ser <u>Asn</u> Glu <u>Ala</u> Phe <u>Ala</u> Asp Leu Trp Lys—Lys | ND | ND | 0.1 |
| 20 | 11–24[e] | Glu Pro Pro Leu <u>Glu</u> <u>Gln</u> Glu <u>Ala</u> Phe <u>Ala</u> Asp Leu Trp Lys—Lys | ND | ND | 0 |
| 13 | 11–24[e] | Glu Pro Pro Leu Ser Gln <u>Lys</u> <u>Ala</u> Phe <u>Ala</u> Asp Leu Trp Lys—Lys | 1,000 | 70 | 14[g] |
| 14 | 11–24[e] | Glu Pro Pro <u>Gln</u> Ser <u>Leu</u> Glu <u>Ala</u> Phe <u>Ala</u> Asp Leu Trp Lys—Lys | 420 | 310 | 99 |
| 15 | 11–24[e] | Glu Pro Pro <u>Gln</u> Ser Gln Glu <u>Ala</u> Phe <u>Ala</u> Asp Leu Trp Lys—Lys | 290 | 390 | 161 |

TABLE 1-continued

Synthetic p53 Peptide Substrates

| SEQ NO NO: | p53 residues[a] | Peptide Sequence[b] | $K_m$ ($\mu$M) | $V_{max}$ (pmol/min/$\mu$g of DNA-PK) | PO$_4$ incorp. (pmol/min/$\mu$g of DNA-PK)[c] |
|---|---|---|---|---|---|
| 16 | 11–24[e] | Glu Pro Pro Leu Thr Gln Glu <u>Ala</u> Phe Ala Asp Leu Trp Lys—Lys | 670 | 460 | 116 |
| 17 | 11–24[e] | Glu Pro Pro <u>Asp</u> Ser Gln Glu <u>Ala</u> Phe Ala Asp Leu Trp Lys—Lys | ND | ND | 48 |
| 18 | 12–24[e] | Pro <u>Glu Glu</u> Ser Gln Glu <u>Ala</u> Phe <u>Ala</u> Asp Leu Trp Lys—Lys | 270 | 410 | 180 |
| 19 | 14–24[e] | Pro <u>Glu</u> Ser Gln Glu <u>Ala</u> Phe <u>Ala</u> Asp Leu Trp Lys—Lys | 200 | 470 | 220 |
| 34 | 11–24[e] | Glu Pro Pro Leu Ser <u>Tyr</u> Glu <u>Ala</u> Phe Ala Asp Leu Leu Lys Lys | ND | ND | 2.3 |

[a]The amino acid positions corresponding to the first and last p53 residues in each peptide are given; all sequences are identical to or variants of human p53 protein except (SEQ ID NO: 2) and (SEQ ID NO: 3), which correspond to mouse p53 protein.
[b]The sequence is given in the three-letter amino acid code; serines (Ser) followed by glutamine (Gln) are shown in bold type; changes from the wild-type sequence of p53 to produce the variant peptides are underlined; lysines (Lys) added at the carboxy terminus are separated by a dash.
[c]Phosphate incorporated for each peptide at 200 $\mu$M.
[d]ND, not determined
[e]Differs from the wild-type p53 sequence and represents a variant of human p53 N terminal sequences
[f]—, an appropriate concentration range for determining the indicated value was not achieved.

Example 4

Phosphorylation Reactions

Phosphorylation reactions were performed in a 20- or 40-$\mu$l final volume as previously described by Chen, et al., *J. Virol.*, 10:5131–5140 (1991) and Lees-Miller, et al., *Mol. Cell. Biol.*, 10:6472–6481 (1990). In particular, in addition to synthetic peptide substrates or protein substrates, the assays contained 50 mM HEPES (pH 7.5), 100 mM KCl, 10 mM MgCl$_2$, 2 mM EGTA, 0.1 mM EDTA and 0.125 mM ATP containing [$^{32}$P]ATP at 0.2 mCi/ml. Sonicated calf thymus DNA was added to 10 $\mu$g/ml. Assays were started by adding 1 $\mu$l of kinase sample. Incubations were at 30° C. for 7 min.

For determinations of kinetic constants, the ATP concentration was 0.5 mM. When present, hsp90 was included at 0.5 mg/ml. Assay mixtures were preincubated at 30° C. for 2 min before addition of 0.1 to 0.5 $\mu$g (protein) of the DNA-PK preparation.

Example 5

Assay of Synthetic Peptides

The transfer of [$^{32}$P]phosphate to synthetic peptides was quantitated by the phosphocellulose paper binding method described by Casnellie, *Methods Enzymol.*, 200:115–120 (1991) and Glass, et al., *Anal. Biochem.*, 87:566–575 (1978). In particular, kinase reactions were stopped by adding an equal volume of 30% acetic acid, and portions of the acidified reaction were spotted on 2- by 2-cm squares of P-81 paper (Whatman, Inc., Clifton, N.J.). Squares were washed four times for 5 min each in 15% acetic acid. The P-81 squares were then transferred to scintillation vials containing 3.5 ml of water, and bound radioactivity was determined from the Cerenkov radiation. Enzyme activity was calculated from triplicate determinations, using the specific activity of the ATP and the protein concentration, which was determined by the Bio-Rad dye-binding assay (Bio-Rad (Bradford) Protein Assay Kit 1, Cat. No. 500-001, Bio-Rad Laboratories, Hercules, Calif.), using bovine serum albumin as the standard. Blank values, obtained without added peptide, gave less than 0.5 pmol of bound phosphate; these blanks were subtracted from assay values with peptides. Control assays indicated that at least 80% of spotted phosphopeptides bound to P-81 squares and that the fraction bound was linear over the concentration range of peptide used. The kinetic constants, $K_m$ and $V_{max}$ for each peptide sequence were calculated from plots of 1/[S] versus 1/V, the values reported are averages of at least two independent determinations. These results, including the quantitation of [$^{32}$P] phosphate transfer for synthetic peptide substrates, are shown in Table 1.

Phosphorylation of peptides that lacked positively charged residues was estimated from gel filtration profiles. Peptides were separated from [$^{32}$P]ATP by passage through a column (1.5 by 12 cm) of Bio-Gel P4 (Bio-Rad Laboratories, Hercules, Calif.) in 10% acetic acid.

Example 6

Analysis of Phosphorylation of Synthetic Peptides by DNA-PK

As shown in Table 1, only the peptides derived from human p53 sequence containing serines 6 and 15 (SEQ ID NO: 4), serine 15 (SEQ ID NO: 8), serine 37 (SEQ ID NO: 6), and serine 166 (SEQ ID NO: 7) were phosphorylated at a significant rate at the concentrations studied. The $K_m$ for (SEQ ID NO: 4), Met$^1$-Lys$^{24}$-Lys (the lysine added at the carboxyl terminus is not part of the p53 sequence), containing both serines 6 and 15 was 210 $\mu$M, and $V_{max}$ was 90 pmol/min/$\mu$g. The $K_m$ for (SEQ ID NO: 8), Glu$^{11}$-Lys$^{24}$-Lys was approximately fifty percent higher (360 $\mu$M), but its $V_{max}$ was four-fold greater (360 pmol/min/$\mu$g of DNA-PK). The $K_m$ for (SEQ ID NO: 6), Asn$^{29}$-Met$^{44}$-Lys-Lys, was twice as high, but its $V_{max}$ was five times greater. (SEQ ID NO: 7), Met$^{160}$-Arg$^{175}$, was phosphorylated at less than half of the rate of (SEQ ID NO: 6), when both were assayed at 200 $\mu$M, but it was active as a substrate for DNA-PK. At 200 $\mu$M, the rate of phosphorylation of (SEQ ID NO: 28), Pro$^{92}$-[Ser$^{99}$]-Gly$^{108}$-Lys-Lys, was less than 7% of the rate at which (SEQ ID NO: 4) was phosphorylated. Three other peptides (SEQ ID NOS: 29, 30 and 31) were also phosphorylated at a negligible rate by DNA-PK. In all cases in which phosphorylation of the peptide substrate was observed, phosphorylation was completely dependent on the presence of added dsDNA. These results clearly demonstrated that all Ser-Gln sequences are not phosphorylated by DNA-PK and that the consensus sequence motif for DNA-PK must include additional amino acid residues.

(SEQ ID NO: 7), $Met^{160}$-$Arg^{175}$, has only one serine; thus, the serine equivalent to p53 residue 166 must be phosphorylated. (SEQ ID NO: 6), $Asn^{29}Met^{44}$-Lys-Lys, has two serines, equivalent to residues 33 and 37 of human p53. To determine which of these were phosphorylated, after incubation with DNA-PK, radiochemical sequence analysis was performed by using a Beckman 890M spinning-cup sequencer (Beckman Instruments, Palo Alto, Calif.) as described by Lees-Miller, et al., *J. Biol. Chem.*, 264:17275–17280 (1989). The peptide was isolated by reverse-phase HPLC, peptidylphosphoserine was converted to S-ethylcysteine, and the position of phenylthiohydantoin (PTH)-S-ethylcysteine was determined by chemical microsequence analysis using an Automated Protein/Peptide sequencer (Applied Biosystems, Foster City, Calif.) and a 120 PTH-Amino Acid Analyzer (Applied Biosystems, Foster City, Calif.) as described by Lees-Miller, et al., *J. Biol. Chem.*, 264:17275–17280 (1989). Only the ninth residue, i.e., equivalent to serine 37, had a significant amount of PTH-S-ethylcysteine, indicating that serine 37 was phosphorylated by DNA-PK whereas the equivalent to serine 33 was not phosphorylated. This result clearly demonstrates that the phosphate-accepting serine must be immediately adjacent to a glutamine, i.e., either Ser-Gln or Gln-Ser. In addition, peptides (SEQ ID NOS: 29 and 31) which do not contain a serine immediately adjacent to a glutamine are not substrates for DNA-PK.

The amino-terminal peptide of human p53 protein, $Met^1$-$Lys^{24}$-Lys, (SEQ ID NO: 4), has four serine residues. Radiochemical sequence analysis showed that the major site of phosphorylation was serine 15. To verify this result, in peptide (SEQ ID NO: 5), $Ser^{15}$ was replaced with alanine, an unphosphorylatable amino acid. This replacement caused the peptide to become an ineffective substrate for DNA-PK. At 200 μAM, (SEQ ID NO: 5), $Met^1$-$[Ala^{15}]$-$Lys^{24}$-Lys, was phosphorylated at about 10% of the rate of the wild-type peptide sequence, confirming that serine 15 was the major site of phosphorylation of (SEQ ID NO: 4) (Table 1). This conclusion was also confirmed with (SEQ ID NO: 8), $Glu^{11}$-$[Ser^{15}]$-$Lys^{24}$-Lys (and other peptide variants of this amino terminal peptide sequence), lacking serines 6 and 9. (SEQ ID NO: 8) was phosphorylated at four times the rate of the (SEQ ID NO: 4), Met,1-$Lys^{24}$-Lys wild-type peptide, but its $K^m$ was 1.5 times higher (Table 1).

A peptide corresponding to mouse p53 residues $Met^4$-$Pro^{31}$, (SEQ ID NO: 2), was also examined (See Table 1). Serine 7 of mouse p53 is at the position equivalent to proline 4 of human p53, and the glutamine at position 8 of mouse p53 is conserved among mammals as reported by Soussi, et al., *Oncogene*, 5:945–952 (1990). After phosphorylation of (SEQ ID NO: 2) the peptide was digested with endoproteinase Glu-C, and the resulting fragments were separated by reverse-phase HPLC. Two major phosphopeptides were obtained, and sequence analyses indicated that one began at $Met^1$ and the other began at $Leu^{15}$. Each peptide was treated to convert phosphoserine to S-ethylcysteine; then they were resequenced. The results show that S-ethylcysteine was present at the positions of $Ser^7$ and $Ser^{18}$ but not at the positions of $Ser^9$ and $Ser^{12}$. Mass spectrographic analysis of the uncleaved, phosphorylated peptide showed the presence of products with masses of 3,176; 3,256; 3,336 as expected for the unphosphorylated peptide and derivatives with one and two phosphates. A synthetic peptide corresponding to mouse p53 residues $Met^4$-$Pro^{13}$ (Table 1) (SEQ ID NO: 3), and containing only $Ser^7$, was phosphorylated very well by DNA-PK. These examples show that both serine-glutamine (Ser-Gln) sites at the amino terminus of murine p53 are phosphorylated by DNA-PK. These mouse p53 sites are also phosphorylated in vivo, suggesting that they may be representative of the in vivo physiological targets for DNA-PK.

Similarly, a synthetic peptide corresponding to mouse p53 residues $Pro^{16}$-$Pro^{31}$, (SEQ ID NO: 63), Pro Leu Ser Gln Glu Thr Phe Ser Gly Leu Trp Lys Leu Leu Pro Pro-Lys Lys, is expected to be an effective substrate for DNA-PK, with $Ser^{18}$ being phosphorylated. In accord with the results with the (SEQ ID NO: 11) variant of the human p53 amino terminus (see Example 7), a variant of the murine p53 amino terminus $Pro^{16}$-$Pro^{31}$, in which $Thr^{21}$ and $Ser^{23}$ are replaced with alanine residues, (SEQ ID NO: 64), Pro Leu Ser Gln Glu Ala Phe AlaG ly Leu Trp Lys Leu Leu Pro Pro-Lys Lys is also expected to be an effective substrate for DNA-PK.

Example 7

Structural Requirements for Peptide Substrates of DNA-PK

To determine the characteristics of peptides derived from the amino-terminal region of human p53 protein that are specific DNA-PK substrates with excellent kinetic properties, several series of peptides based on the sequence surrounding serine 15 of human p53 sequence were made. Each peptide was then tested for substrate activity (Table 1).

Starting with (SEQ ID NO: 8), $Glu^{11}$-$[Ser^{15}]$-$Lys^{24}$-Lys, as a basis for comparison, individual residues were changed. First, $Thr^{18}$ and $Ser^{20}$ were changed to alanine, leaving $Ser^{15}$ as the only phosphorylation site (SEQ ID NO: 11) (Table 1). These changes produced only a twofold increase in $K_m$ and no significant change in $V_{max}$. Thus, (SEQ ID NO: 11), which has only one possible site of phosphorylation corresponding to that for DNA-PK, is as good a substrate as was (SEQ ID NO: 8) corresponding to the wild-type human p53 sequence, which has another serine and a threonine residue which may be phosphorylated by other protein kinases. Therefore, this sequence was chosen as a new base for further sequence changes. Changing $Gln^{16}$ to glutamic acid (SEQ ID NO: 32) effectively eliminated the ability of the sequence to act as a DNA-PK substrate. Changing $Gln^{16}$ to asparagine (SEQ ID NO: 33) also eliminated the ability of the sequence to act as a DNA-PK substrate. This result indicated that glutamine could not be replaced with either glutamic acid or with a different basic amino acid in DNA-PK substrates. Taken with the above, these results indicated that an adjacent glutamine was required for phosphorylation of serine 15 of human p53-derived amino-terminus peptides.

To determine whether the position of glutamine is critical for phosphorylation activity, first the positions of $Gln^{16}$ and $Glu^{17}$ were switched to form peptide (SEQ ID NO: 20). (SEQ ID NO: 20) had negligible substrate activity, indicating that the glutamine must be immediately adjacent to the phosphate-accepting amino acid. Next, the position of the glutamine was switched to the amino terminal side of the phosphate-accepting amino acid rather than the carboxyl terminal side to form peptide (SEQ ID NO: 14). (SEQ ID NO: 14), the peptide with the positions of $Gln^{16}$ and $Leu^{14}$ switched, was at least as good a substrate as the base peptide (SEQ ID NO: 11) and almost as good a substrate as (SEQ ID NO: 8). Taken with the above results, these results suggested that glutamine must be immediately adjacent to the phosphorylated residue, but it may either follow or precede that residue, i.e., the results indicate that the phosphorylation acceptor amino acid pair in a DNA-PK substrate peptide could be either serine-glutamine (Ser-Gln) or glutamine-serine (Gln-Ser). (SEQ ID NO: 16), with threonine substituted at residue 15, was a slightly better substrate than the base sequence (SEQ ID NO: 11). This result suggests that DNA-PK does not discriminate against threonine sites in these substrates and that threonine-glutamine (Thr-Gln) and glutamine-threonine (Gln-Thr) are acceptable phosphate accepting amino acids pairs in DNA-PK peptide substrates.

(SEQ ID NO: 15), with Leu$^{14}$ changed to glutamine, i.e., where the serine was surrounded by glutamines, was slightly better as a substrate. This suggests that in addition to having a phosphate accepting amino acid pair selected from the group consisting of Ser-Gln, Gln-Ser, Thr-Gln and Gln-Thr, an additional characteristic of the peptides that are effective substrates for phosphorylation of serine 15 of human p53 by DNA-PK is the presence of a glutamic acid or glutamine immediately adjacent to the amino acid pair on either the amino- or carboxyl-side. This is demonstrated by comparing the phosphorylation of peptides (SEQ ID NO: 13) and (SEQ ID NO: 11) and by comparing the phosphorylation of peptides (SEQ ID NOs: 15, 14, 11, 18 and 19). The presence of the adjacent glutamic acid or glutamine residue(s) enhanced phosphorylation of the peptides, particularly in the cases of peptides (SEQ ID NOS: 15, 18 and 19). Thus, in addition to the phosphate accepting amino acid pair, effective substrates for DNA-PK also include an enhancer amino acid, which may be either glutamine or glutamic acid, located immediately adjacent to the amino acid pair on either the amino- or the carboxyl side of the amino acid pair and forming a phosphate accepting amino acid pair-enhancer unit.

(SEQ ID NO: 13) has lysine substituted for Glu$^{17}$, but it has an intact Ser-Gln-sequence. (SEQ ID NO: 13) is a comparatively poor DNA-PK substrate. This result suggested that basic residues, other than glutamine, (see results with (SEQ ID NO: 15)) near a Ser-Gln sequence may inhibit recognition and phosphorylation by DNA-PK and further suggested that, as described above, the glutamic acid that was at this position may have enhanced recognition and phosphorylation by DNA-PK. In (SEQ ID NO: 17), the leucine (Leu$^{14}$) is replaced with aspartic acid, making this peptide a less effective substrate for DNA-PK than peptides (SEQ ID NOS: 15 AND 16). This suggested that acid residues (other than glutamic acid, see results with (SEQ ID NOS: 18 and 19)), near the Ser-Gln amino acid pair may inhibit phosphorylation by DNA-PK and further suggested that glutamic acid near the pair acts to enhance phosphorylation by DNA-PK.

Two additional series of peptides were designed and synthesized and tested to determine the requisite or desirable lengths of amino acid spacer sequences to be added on the amino and carboxyl sides of the phosphate accepting amino acid pair and its attendant glutamic acid or glutamine enhancer (the amino acid pair-enhancer unit) so as to generate a peptide substrate with excellent kinetic properties while providing a specific peptide substrate that was additionally cost effective to synthesize. The first series was designed to determine the optimum length characteristics for the spacer sequence on the amino terminal side of the amino acid pair-enhancer unit. This series is embodied in peptides (SEQ ID NOs: 4, 11, 15, 18 and 19) which have 14, 4, 3, 2 and 1 amino acids, respectively, on the amino-terminal side of the Ser-Gln-Glu, Gln-Ser-Gln or Glu-Ser-Gln phosphate accepting amino acid pair-enhancer unit. The results (Table 1) demonstrate that a shorter sequence on the amino terminal side of the phosphate accepting amino acid pair-enhancer unit enhanced phosphorylation by DNA-PK. A steady improvement in the kinetic properties of the peptide substrates was observed as the amino-terminal spacer sequence was shortened. The results suggest that while peptides with a four-amino acid spacer on the amino terminal side of the amion acid pair-enhancer unit are effective substrates for DNA-PK, a peptide with a single amino acid spacer on the amino terminal side of the phosphate accepting amino acid pair-enhancer unit is an optimal configuration for a DNA-PK substrate and also provides a peptide that is less expensive to synthesize.

The second series of peptides was designed to determine the optimum characteristics for a spacer sequence on the carboxyl terminal side of the amino acid pair-enhancer unit. This series is embodied in peptides (SEQ ID NOS: 8, 11, 10 and 9) which have 7, 7, 4 and 3 amino acids, respectively, on the carboxyl-terminal side of the Ser-Gln-Glu phosphate accepting amino acid pair-enhancer unit. The peptides (SEQ ID NOS: 9 and 10) (Table 1) were phosphorylated at approximately 10% of the rate of the control (SEQ ID NO: 8) by DNA-PK, primarily because of a large increase in K$_m$. They were also less than 20% as effective substrates as (SEQ ID NO: 11). The results suggest a minimum length for enhanced substrate activity is spacer sequence of seven amino acids on the carboxyl side of the phosphate accepting amino acid pair-enhancer unit. Although (SEQ ID NOs: 3 and 7) are sequences unrelated to serine 15 of human p53 protein, the phosphorylation results with peptides (SEQ ID NOs: 3 and 7), both of which have carboxyl spacer sequences of eight amino acids, suggest that peptides with even longer carboxyl spacer sequences are effective substrates for DNA-PK.

Thus, while the spacer at the amino side of the amino acid pair-enhancer unit may be reduced in length to provide a more effective substrate for DNA-PK and to provide a substrate that is inexpensive to synthesize, the spacer at the carboxyl side of the amino acid pair-enhancer unit cannot be reduced to a length that is substantially less than seven, and when cost of the peptide is not of significance, the carboxyl side spacer sequence could be longer than seven amino acids and the peptide would remain an effective DNA-PK substrate. For example, (SEQ ID NO: 2), which contains two serines that are phosphorylated by DNA-PK, effectively provides a peptide substrate with two separate carboxyl spacer sequences. One carboxyl spacer, for Glu$^6$-Ser$^7$-Gln$^8$, is twenty-three (23) amino acids in length and the other, for Ser$^{18}$-Gln$^{19}$-Glu$^{20}$ is eleven (11) amino acids in length.

As a control to ensure that the substrates which were ineffective DNA-PK substrates had not appeared to be so due to the presence of inhibitory substances in those preparations, all of the poorer substrate peptides, i.e., (SEQ ID NOS: 5, 28, 29, 31, 9, 10, 32, 33, 20 and 13), i.e., were added to (SEQ ID NO: 8) phosphorylation assays at concentrations of up to 250 µM with the concentration of (SEQ ID NO: 8) maintained at 100 µM. None of these peptides significantly inhibited the phosphorylation of (SEQ ID NO: 8). Therefore, these peptides were not ineffective substrates due to the presence of inhibitors of DNA-PK activity that prevented these peptides from being phosphorylated.

Example 8

A Second Determinant for DNA-PK Activation is Substrate and Kinase Binding to DNA DNA-PK is activated by relatively low concentrations of DNA, and, as was shown by using calf thymus DNA and hsp90, DNA-PK remains active at DNA concentrations well above the $K_m$ for activation (Lees-Miller, et al., 1990, *Mol. Cell. Biol.*, 10:6472–6481). This result was confirmed by using p53 synthetic peptides as DNA-PK substrates and several synthetic oligonucleotides made of alternating dA and dC. The rate of phosphorylation of a synthetic peptide (SEQ ID NO: 11) (Table 1) was constant at oligonucleotide concentrations of between 5 and >200 μg/ml for0 dG-dC oligomers of chain length 16 or above, and this rate was the same as that obtained with calf thymus DNA.

To determine whether DNA binding affected p53 phosphorylation by DNA-PK, the rate of phosphorylation of recombinant wild-type mouse p53 was measured as a function of DNA concentration. At low calf thymus DNA concentrations (0 to approximately 10 μg/ml), the initial rate of p53 phosphorylation increased sharply but then decreased as the DNA concentration was further increased. At DNA concentrations of 100 μg/ml, the rate of p53 phosphorylation fell to approximately 25% of the rate at 5 μg/ml. A similar dependence of phosphorylation rate on calf thymus DNA concentration was observed using SV40 TAg or the human Oct-1 POU domain as substrates.

In contrast to using natural DNA activators, the rate at which wild-type mouse p53 was phosphorylated when short oligonucleotides were used to activate DNA-PK was substantially lower at all oligonucleotide concentrations (0 to 100 μg/ml) assayed, and the rate remained constant at oligonucleotide concentrations above those required for maximal DNA-PK activation (about 5 μg/ml). Thus, when DNA-PK was activated by short oligonucleotides, p53 behaved as a substrate very much like hsp90, a non-DNA-binding substrate. However, when longer calf thymus DNA fragments were used to activate the kinase, the rate of p53 phosphorylation was highly dependent on the concentration of DNA at low DNA concentrations, and at high calf thymus DNA concentrations (above 100 μg/ml), it fell and approached the rate of phosphorylation obtained with short oligonucleotides. Because it is likely that at low concentrations of DNA, the DNA-binding DNA-PK protein substrates and the DNA-PK are bound to the same DNA molecule and that at high concentrations they are more likely to be bound to different DNA molecules, these results strongly suggest that the rate of substrate phosphorylation may be enhanced substantially when substrate and kinase bind to the same activator DNA fragment. Thus, DNA binding is another factor that influences substrate recognition by DNA-PK.

Example 9

Peptide Glu Pro Pro Leu Ser Gln Glu Ala Phe Ala Asp Leu Trp Lys-Lys (SEQ ID NO:11) is a Specific DNA-PK Substrate All proteins known to be phosphorylated by DNA-PK in vitro are also in vitro substrates for other protein kinases. Inspection of the phosphorylation site consensus sequence motifs for other characterized protein kinases reported by Pearson, et al. in *Methods Enzymol*, 200:62–81 (1991), suggested that none were likely to phosphorylate (SEQ ID NO: 11). This suggestion was tested directly for casein kinase I, casein kinase II, and the catalytic subunit of cyclic AMP kinase. The incorporation of phosphate into (SEQ ID NOS: 11 and 20) by these kinases was less than 5 percent of the incorporation into the standard peptides used to assay each kinase, when assayed at the same concentration (200 or 500 μM). Thus these other kinases did not phosphorylate the DNA-PK peptide substrate (SEQ ID NO: 11) or the DNA-PK negative control peptide (SEQ ID NO: 20) at significant rates compared with their usual substrates. In addition, DNA-PK also did not phosphorylate the casein kinase II substrate peptides Arg Arg Arg Glu Glu Glu Thr Glu Glu Glu (SEQ ID NO: 37) and Arg Arg Arg Asp Asp Asp Ser Asp Asp Asp Asp (SEQ ID NO: 39), the casein kinase I substrate peptide Asp Asp Asp Glu Glu Ser Ile Thr Arg Arg (SEQ ID NO: 35), or the S6 kinase substrate Arg Arg Leu Ser Ser Leu Arg Ala (SEQ ID NO: 36). Less than 0.1 pmole $PO_4$/min/μg of DNA-PK was incorporated into each peptide by DNA-PK in 10 min at 30° C. when assayed at 200 μM.

The results with (SEQ ID NO: 11) are indicative that derivatives of that sequence are also specific DNA-PK substrates. For example, in (SEQ ID NO: 12) $Trp^{23}$ of (SEQ ID NO: 11) is replaced by a Leu, which is not a phosphate-accepting amino acid in kinase reactions. Likewise, (SEQ ID NO: 14), which has the same amino acid composition as (SEQ ID NO: 11) except that $Gln^{16}$ and $Leu^{14}$ are exchanged to generate the phosphorylation site $Gln^{14}$-$Ser^{15}$-$Leu^{16}$, is expected to be a specific substrate for DNA-PK (SEQ ID NO: 15), in which $Leu^{14}$ is replaced by a Gln residue, is also expected to be a DNA-PK-specific substrate since the Gln residue cannot accept phosphate in a kinase reaction. The peptides (SEQ ID NOS: 18 and 19) are also expected to be DNA-PK specific substrates since they are formed by truncation and rearrangement of the amino acids comprising the first spacer sequence located at the amino side of the phosphate-accepting amino acid pair-enhancer unit of the substrate peptide (SEQ ID NO: 11).

Example 10

(SEQ ID NO: 11) Specifically Detects DNA-PK Activity in Crude Cell Extracts (SEQ ID NO: 11) (Ser-Gln-Glu peptide) and (SEQ ID NO: 20) (Ser-Glu-Gln peptide), as shown in Table 1, were examined to determine whether they would function as specific indicators of the presence of DNA-PK activity in crude cell extracts. To examine cells for DNA-PK content, extracts from HeLa, T98G human glioblastoma, and mouse L 929 cells were prepared by freeze-thaw lysis of cells harvested from five nearly confluent 9-cm-diameter plates as described in Example 1 and by Lees-Miller, et al. *J. Biol. Chem.*, 264:2431–2437 (1989). T98G (ATCC CRL 1690) is a human glioblastoma cell line; L-929 (ATCC CCL 1) was derived from connective tissue of the NCTC 2071 mouse. Based on earlier work with natural protein substrates, it was expected that extracts of HeLa and T98G cells would contain a significant amount of DNA-PK activity while the extracts of mouse L 929 would contain little, if any, DNA-PK activity. Lysates in low-salt buffer were centrifuged at 10,000×g, to give a supernatant fraction (designated S10) and pellets (designated P10). The pellets were washed by resuspension in a high salt buffer (0.5 M KCl, 25 mM N-2-hydroxyethylpiperazine-N'-2-ethanesulfonic acid (HEPES; pH 7.5), 10 mM $MgCl_2$, 1 mM dithiothreitol) and were sonicated. The sonicated suspension was centrifuged at 10,000×g for 10 min to give a second supernatant fraction (designated P10S), which was diluted with buffer lacking KCl to give a volume equal to that of the original supernatant (S10). Protein concentrations, determined using the Bio-Rad dye-binding assay, were as follows: HeLa S10, 3 mg/ml; HeLa P10S, 1 mg/ml; T98G S10, 3.5 mg/ml;,T98G P10S, 1 mg/ml; L-929 S10, 1 mg/ml; and L-929 P10S, 0.3 mg/ml. These extracts were assayed for the ability to phosphorylate (SEQ ID NOS: 11 and 20) with and without added calf thymus DNA. The results are shown in Table 2.

TABLE 2

Phosphorylation of synthetic peptides in crude cell extracts

|  | (SEQ ID NO: 11) Ser—Gln—Glu | | (SEQ ID NO: 20) Ser—Glu—Gln | |
|---|---|---|---|---|
| Cells and | PO$_4$ incorporated (nmol/min/ml of extract)[b] | | | |
| Fraction[a] | + DNA | − DNA | + DNA | − DNA |
| HeLa | | | | |
| S10 | 33.8 | 0.8 | 0.3 | 0.0 |
| P10S | 28.9 | 6.5 | 0.0 | 0.0 |
| T98G | | | | |
| S10 | 22.6 | 0.2 | 0.04 | 0.02 |
| P10S | 15.0 | 1.2 | 0.0 | 0.0 |
| L 929 | | | | |
| S10 | 0.0 | 0.0 | 0.0 | 0.0 |
| P10S | 0.005 | 0.0 | 0.0 | 0.0 |

[a]The soluble fraction (S10) and a salt wash (P10S) of the insoluble fraction, in equal volumes, were prepared from about 2.5 × 10$^7$ cells as described.
[b]Extracts were incubated for 10 min at 30° C. with the indicated peptide (Table 1) at 200 μM and with (+) or without (−) calf thymus DNA at 10 μg/ml. Phosphate incorporation was approximately linear for the assay period (data not shown). Background values from reactions without peptide were substracted.

As shown in Table 2, extracts of the two human cell lines phosphorylated (SEQ ID NO: 11) at rates that were 200–300 times that of the assay background. Furthermore, phosphorylation by the S10 fractions was entirely dependent on added DNA. Phosphorylation by the P10S fraction was partially dependent on added DNA. This suggests that some DNA was present in the sonicated, salt wash of the freeze-thaw 10,000 g pellet, which is expected since some DNA of the nuclei of the pellet would be extracted by sonication in high salt. In contrast, (SEQ ID NO: 20) was poorly phosphorylated, if at all, by all extracts. The level of phosphate incorporated into (SEQ ID NO: 20) was not significantly different from the amount of background radioactivity on the filter due to residual radioactivity from the ATP preparation. Table 2 also shows that DNA-dependent kinase activity was distributed about equally between the S10 and P10S fractions. Western immunoblot analysis, using an antibody against a partial DNA-PK cDNA fusion protein (anti-DNA-PK antibody), confirmed that roughly equal amounts of the 350-kDa DNA-PK peptide were present in the two fractions.

Mouse L 929 cell extracts did not appear to contain DNA-PK. (SEQ ID NO: 11) was phosphorylated at a rate that was at least 100 times lower than the rates at which it was phosphorylated by the human cell extracts. This result is consistent with the previous observation that mouse L 929 cell extracts did not phosphorylate hsp90 in a DNA-dependent manner. L 929 cell extracts also lacked a 350-kDa polypeptide that reacted with the anti-DNA-PK antibody. These results indicate that mouse L 929 cells have little DNA-PK activity compared with the cultured human cells that have been examined. Several other rodent cell lines, including SV40-transformed BALB/c mouse embryo fibroblasts and secondary rat embryo fibroblasts, also had little if any DNA-PK activity. Rodent cell extracts are well-known to have other kinases, including casein kinases I and II. Therefore, these results also demonstrate that (SEQ ID NOS: 11 and 20) are not effective substrates for the common kinases of mammalian cells. Thus, (SEQ ID NO: 11) represents a specific peptide substrate for detection and quantitation of DNA-PK activity in cell extracts and other biological samples. It is expected that the previously discussed derivatives of (SEQ ID NO: 11), (SEQ ID NOS: 12, 14, 15, 18 and 19), are also specific peptide substrates for detection and quantitation of DNA-PK activity in cell extracts and other biological samples.

Example 11

Cultured Somatic Cells from Primates have High Concentrations of DNA-PK Compared to Cultured Somatic Cells from other Eukaryotes Extracts of additional primate and rodent cells were tested for the presence of DNA-PK activity in accordance with the method of the present invention. The DNA-PK activity was determined using the methods described in Examples 1, 4 and 5 for seven human cell lines, two African green monkey kidney lines, and six rodent cell lines. These results are shown in Table 3.

Extracts were prepared essentially as described in Example 10. Cells were lysed by freezing and thawing in hypotonic buffer; soluble (S10) "cytoplasmic" and insoluble in (P10) "nuclear" fractions were made by centrifuging lysates at 10,000×g for 10 min. The insoluble fraction was extracted with buffer containing 0.5 M KCl, which releases any DNA-PK that is bound to DNA. After centrifugation of the salt-washed pellet fraction, which removed the remaining insoluble material, the salt extract (P10S) was diluted and assayed as previously described.

Protein concentrations, determined using the Bio-Rad dye binding assay, were between 0.3 and 6 mg/ml. Extracts were incubated at 30° C. for 10 min with each peptide at 0.2 mM in the absence of added DNA (−DNA) or with 10 μg/ml calf thymus DNA (+DNA). After incubation the reaction mixtures were acidified with an equal volume of 30% acetic acid and spotted on to Whatman P-81 phosphocellulose paper (Whatman, Inc., Clifton, N.J.). The filters then were washed extensively in 15% acetic acid before the adsorbed radioactivity was quantitated as described in Example 5.

The amount of phosphate incorporated was calculated from the specific activity of the ATP. The rate of phosphate incorporation into the Ser-Gln-Glu peptide (Table 1) (SEQ ID NO: 11) in the presence of calf thymus DNA was approximately linear throughout the 10 minute reaction incubation period. Parallel assays were performed without added peptide, and these background values were subtracted to produce the activities that are shown in Table 3. Background values varied but, in all cases, were less than 0.2 nmol/min/mg (a few percent of the activity present in human cells). The specific activities were calculated from the total activity in the two fractions divided by the total protein in the two fractions. The percent of total DNA-PK activity in the S10 and P10S fractions was determined with peptide (SEQ ID NO: 11) in the presence of added calf thymus DNA. Extracts without substantial DNA-PK activity were examined for their ability to inhibit purified DNA-PK. Inhibitory activity was not detected.

As shown in Table 3, the extracts of human cells lines have DNA-PK activity that is readily detectable with the Ser-Gln-Glu (SEQ ID NO: 11) peptide, and in each case phosphorylation of the Ser-Gln-Glu peptide by supernatant fractions was highly dependent on added calf thymus DNA (Table 3). DNA-dependent phosphorylation of the Ser-Gln-Glu peptide also was observed with SO extracts from CV-1 and COS-1 African green monkey cells, but little phosphorylation of the Ser-Gln-Glu peptide was observed with extracts from any of the six rodent cell lines. In addition, little, if any, phosphorylation of the Ser-Gln-Glu peptide was seen using extracts of Drosophila Kc cells or in *Spodoptera fragiperda* (fall army worn) Sf9 cells. The Ser-Gln-Glu peptide was also phosphorylated by the salt wash of the insoluble fraction (Table 3, P10S) from human and monkey cells, but substantial phosphorylation by these fractions occurred without added DNA. The apparent DNA-independent phosphorylation observed with P10S fractions probably results from the presence of endogenous chromatin-derived DNA fragments, as previously discussed in Example 10. None of the extracts phosphorylated the Ser-Glu-Gln peptide (SEQ ID NO: 20) at a significant rate, with or without added DNA.

TABLE 3

DNA-PK Activity in Extracts of Primate and Rodent Cells

| Species & Cell Line | Fraction | (SEQ ID NO: 11) Specific Activity | | | | (SEQ ID NO: 20) Specific Activity | |
|---|---|---|---|---|---|---|---|
| | | + DNA | − DNA | % of Total | Total | + DNA | − DNA |
| Human MRC 5[a] | S10 | 13.6 | 0.01 | 97.9 | | 0.30 | 0.11 |
| | P10S | 3.1 | 1.02 | 2.1 | 15.1 | 0.04 | 0.02 |
| Human HeLa-JW[b] | S10 | 11.0 | 0.26 | 72.5 | | 0.1 | 0.0 |
| | P10S | 24.9 | 5.6 | 27.5 | 14.9 | 0.1 | 0.0 |
| Human T98G[c] | S10 | 6.46 | 0.06 | 60.6 | | 0.01 | 0.01 |
| | P10S | 12.9 | 1.0 | 39.4 | 7.4 | 0.0 | 0.0 |
| Human HPB-ALL[d] | S10 | 4.5 | 0.05 | 28.5 | | 0.0 | 0.04 |
| | P10S | 22.1 | 14.7 | 71.5 | 10.4 | 0.05 | 0.04 |
| Human 293-S[e] | S10 | 3.1 | 0.3 | 34.5 | | 0.01 | 0.0 |
| | P10S | 16.3 | 0.4 | 64.5 | 6.4 | 0.04 | 0.0 |
| Human A549[f] | S10 | 7.5 | 0.1 | 28.6 | | 0.0 | 0.02 |
| | P10S | 31.1 | 0.9 | 71.4 | 16.4 | 0.01 | 0.06 |
| Human Raji[g] | S10 | 3.8 | 0.6 | 47.9 | | 0.0 | 0.08 |
| | P10S | 13.5 | 15.5 | 52.1 | 6.0 | 0.0 | 0.0 |
| Monkey CV-1[h] | S10 | 5.6 | 0.8 | 42.0 | | 0.05 | 0.0 |
| | P10S | 18.1 | 6.3 | 58.0 | 9.4 | 0.08 | 0.08 |
| Monkey COS-1[i] | S10 | 3.8 | 0.85 | 54.5 | | 0.02 | 0.0 |
| | P10S | 10.7 | 8.4 | 45.5 | 5.4 | 0.24 | 0.0 |
| Mouse L-929[j] | S10 | 0.0 | 0.0 | — | | 0.0 | 0.0 |
| | P10S | 0.02 | 0.0 | — | 0.0 | 0.0 | 0.0 |
| Mouse Balb/c MEF | S10 | 0.10 | 0.01 | — | | ND[o] | ND |
| | P10S | 0.15 | 0.09 | — | 0.1 | ND | ND |
| Mouse SV-Balb/c[k] | S10 | 0.04 | 0.01 | 42 | | 0.06 | 0.0 |
| | P10S | 0.20 | 0.15 | 58 | 0.1 | 0.04 | 0.0 |
| Rat REF[l] | S10 | 0.05 | 0.03 | 8 | | 0.0 | 0.02 |
| | P10S | 0.50 | 0.38 | 92 | 0.3 | 0.0 | 0.03 |
| Hamster V79[m] | S10 | 0.11 | 0.01 | 39 | | 0.0 | 0.0 |
| | P10S | 0.61 | 0.0 | 61 | 0.2 | 0.05 | 0.05 |
| Hamster CHO[n] | S10 | 0.06 | 0.05 | 32 | | 0.01 | 0.0 |
| | P10S | 0.05 | 0.36 | 68 | 0.2 | 0.06 | 0.0 |

[a]MRC-5 (ATCC CCL 171) cells are secondary diploid cells from normal human lung tissue (obtained from J. C. Barrett, NIEHS, Research Triangle Park, NC).
[b]HeLa-JW are a derivative of HeLa cells (ATCC CCL 2) selected for use in adenovirus plaque assays (obtained from J. Williams, Carnegie-Mellon University, Pittsburg, PA).
[c]T98G cells (ATCC CRL 1690) are derived from a human glioblastoma (obtained from E. Appella, Laboratory of Cell Biology, Building 37, NIH Bethesda, MD).
[d]HPB-ALL are a human T-cell derivative (obtained from D. Morrisson, Frederick Cancer Research Center, Frederick, MD).
[e]293-S (from ATCC CRL 1573) are suspension adapted primary human embryonic kidney cells transformed by adenovirus 5 DNA (obtained from B. Stillman, Cold Spring Harbor Laboratories, Cold Spring Harbor, NY).
[f]A549 (ATCC CCL 185) was derived from human lung carcinoma tissue (American Type Culture Collection, Rockville, MD).
[g]Raji (ATCC CCL 86) are lymphoblast-like cells derived from a Burkett lymphoma (American Type Culture Collection, Rockville, MD).
[h]CV-1 cells (ATCC CCL 70) are immortalized African Green Monkey kidney cells (American Type Culture Collection, Rockville, MD).

TABLE 3-continued

DNA-PK Activity in Extracts of Primate and Rodent Cells

| | | Specific Activity (nmol PO$_4$/min/mg protein) | | | | | |
|---|---|---|---|---|---|---|---|
| | | (SEQ ID NO: 11) Specific Activity | | | | (SEQ ID NO: 20) Specific Activity | |
| Species & Cell Line | Fraction | + DNA | − DNA | % of Total | Total | + DNA | − DNA |

$^i$COS-1 (ATCC CRL 1650) were derived from CV-1 cells by transformation with origin defective SV40 DNA (American Type Culture Collection, Rockville, MD).
$^j$L-929 (ATCC CCL 1) was derived from connective tissue of the NCTC 2071 mouse (obtained from the Tissue Culture Facility of the State University of New York at Stony Brook, Stony Brook, NY).
$^k$SV-Balb/c are early-passage SV40-transformed primary Balb/c mouse embryo cells (obtained from A. Lewis, Viral Pathogenesis Section, Building 7, NIH, Bethesda, MD).
$^l$REF were early-passage secondary rat embryo cells (obtained from P. Tegtmeyer, State University of New York at Stony Brook, Stony Brook, NY).
$^{m,n}$V79 and CHO (ATCC CCL-61) are Chinese hamster cell lines derived from lung and ovary tissue, respectively (obtained from M. Bender, Medical Department, Brookhaven National Laboratory, Upton, NY).
$^o$ND = Not determined.

Example 12

Optimal DNA-PK Assay Conditions

Experiments were performed to determine optimal DNA-PK assay conditions. It was determined that DNA-PK is active over a broad pH range and the most common buffers with the exception of phosphate buffers. A summary of assay conditions that optimize DNA-PK activity in vitro is found in Table 4 along with a summary of conditions that result in 50% inhibition of DNA-PK activity.

As shown in Table 4 the influence of ionic strength on activity is modest at concentrations below physiological concentrations. Activity decreases significantly at higher salt concentrations, presumably because the enzyme can no longer bind to DNA. Activity requires a divalent cation, magnesium being more effective than manganese. Calcium and zinc are poor substitutes for magnesium. DNA-PK activity was inhibited by phosphate, pyrophosphate, heparin, and by high concentrations of glycerol. Purified DNA-PK is active in 0.5% NP-40 or Triton-X100, but little DNA-dependent phosphorylation is observed in cell lysates prepared with these non-ionic detergents.

TABLE 4

Assay Conditions for DNA-PK

| Parameter | Normal Reaction Concentration | Effective Range |
|---|---|---|
| pH | 7.5 | 6.8–9.2 |
| Salt (mM) | 100 | 20–120 |
| MgCl$_2$ (mM) | 10.0 | ≈1–>10 |
| ds DNA (μg/ml) | 10.0 | ≈2–>1000 |
| ATP (mM) | 0.5 | 0.02–>5 |
| Specific Activity (μCi/μmol) | 300 | |
| Substrate Peptide (mM) | 200 | ≈50–≈1000 |
| Protein (mg/ml) | 0.1 | ≈0.01–≈1 |

| Inhibitor | 50% Inhibition |
|---|---|
| Salt (mM) | 180 |
| Glycerol (% v/v) | 25 |
| Phosphate (mM) | 10 |
| Pyrophosphate (mM) | 3 |
| Heparin (μg/ml) | 1 |
| Single Stranded DNA (μg/ml) | 20 |

The methods used to obtain results in the second section (Inhibitor section) of Table 4 are illustrative of methods that are applicable to identifying substances that alter the activity of DNA-PK. In each assay, the concentrations of the suspected inhibitory substances was increased and the results compared to reaction assays that did not contain the substances, particularly in the cases of Glycerol, phosphate, pyrophosphate, heparin and single stranded DNA. Comparable assays could be used to detect and assess substances that altered DNA-PK activity in a positive manner to stimulate DNA-PK activity.

Furthermore, as in Example 11, cell extracts can also be examined for the presence of substances that alter the activity of DNA-PK. For example, the Rat REF cell extracts displayed very little DNA-PK activity. If these cell extracts appeared negative for DNA-PK because of the presence of an inhibitory substance or compound, if such extracts were added to standard in vitro DNA-PK assays in a manner illustrated by the second section of Table 4, DNA-PK activity would have been reduced as the amount of extract added to the reaction was increased. As this was not found, the extracts did not contain substances that negatively affected DNA-PK activity. Conversely, cell extracts containing substances and compounds that enhance DNA-PK activity could be identified by similar procedures.

Example 13

Isolation of Phosphopeptides by Immobilized Metal Chromatography

Immobilized metal affinity chromatography provides a method for separating phosphopeptides from similar or identical non-phosphorylated peptides. Phosphate binds tightly to chelated iron at acid pH (Muszyhska, et al., 1986, *Biochemistry*, 25:6850–6853; Anderson, et al., 1986, *Anal. Biochem.*, 154:250–254). Most non-phosphorylated peptides and proteins do not bind immobilized metal ions. The ability to purify phosphopeptides is important for identifying sites in proteins that are phosphorylated. This technique could be applied to a method for detecting DNA-PK activity in the absence of a radioactive phosphate donor.

Phosphopeptides are isolated using immunodiacetic acid (chelating)-Sepharose 6B (Sigma Chemical Co., St. Louis, Mo.). This procedure is used for 1–5 mg of peptides. This size column is appropriate for ~200 nmoles of phosphoprotein. All steps are performed at room temperature unless otherwise indicated.

A 1×6 cm (5 ml capacity) column of chelating-Sepharose 6B (Pharmacia-LKB Biotechnology, Piscataway, N.J. or Sigma, St. Louis, Mo.) or an equivalent IDA-resin (Sigma Chemical Co., St. Louis, Mo.) is washed with 4 volumes (20 ml) of $H_2O$. The theoretical capacity is about 2 micromoles of phosphoprotein. The column is then washed with 4 volumes (20 ml) of 50 mM Tris-HCl, pH 7.6, 100 mM EDTA, and 500 mM NaCl, followed by a wash with 4 volumes (20 ml) of $H_2O$. The column is then saturated with iron by washing with 4 volumes 50 mM ferric chloride. After saturation the column is washed with 2 volumes 0.1 M acetic acid to remove any loosely bound iron. The peptide mixture, produced from a phosphorylation reaction as described in Example 4; is loaded onto the column in 4 ml of 0.1 M acetic acid. After loading, the column is washed with 4 volumes (20 ml) of 0.1 M acetic acid to remove any unbound peptides. The column is then washed with 4 volumes (20 ml) of 0.1 M sodium acetate, pH 5.0 (0.1 M acetic acid adjusted to pH 5.0 with sodium hydroxide). Finally, the column is washed with 4 volumes (20 ml) of 1% ammonium acetate (pH 6.3).

Phosphopeptides are eluted with 4 column volumes 1% ammonium acetate adjusted to pH 8.3. Samples are collected in 0.5–1.0 ml sample volumes and pooled according to pH (spot test on paper). Samples are concentrated by Speed-vac (Savant Instruments, Farmingdale, N.Y.). The sample may be quantitated, for example, by amino acid analysis or by UV absorption to determine how much phosphopeptide was obtained.

Example 14

Measurement of Chemical Phosphate by Malachite-Green Assay

An additional method to perform protein kinase assays without using radio-labeled phosphate donors makes use of a Malachite-Green assay for chemical phosphate. The following procedure is applicable to detection and quantitation of DNA-PK activity using natural protein substrates or using synthetic peptide substrates.

After performing phosphorylation reactions as described in the Example 4, the measurement of chemical phosphate in protein is performed using the Malachite-Green assay. The Malachite-Green assay is used exactly as described by Buss and Stull in Methods Enzymol., 99:7–14 (1983) as follows. The useful range of the assay is 0.2 to 1.5 nmoles of protein phosphate. Accurate measurements require duplicate or triplicate samples and a similar quantity for measurement of protein content. Protein concentration is best determined by duplicate amino acid analysis unless an accurate extinction coefficient is known. Common problems with this assay include: (1) high backgrounds from phosphate contaminated reagents or glassware, (2) adherence of non-covalently associated protein phosphate, (3) incomplete precipitation of protein by TCA and (4) inaccurate measurement of total protein. The precautions described by Buss and Stull are followed scrupulously, and positive and negative controls are included with each assay. The assay for samples and for the standard curve are processed in exactly the same way. A sample standard curve is shown in Table 5.

To measure DNA-PK activity using this assay it is essential to first remove the ATP and any inorganic phosphate from the sample. With protein substrates such as hsp90, this can be accomplished by TCA precipitation. Many short peptides are soluble in TCA. Thus, the peptide must first be purified from ATP and any non-peptide bound phosphate using properties of the peptides including the tag moiety. These might include gel filtration as described in Example 5, purification on and elution from phosphocellulose, or purification using a different tag moiety. The purified or partially purified phosphopeptide, free of other sources of phosphate, is redissolved in phosphate-free water or dilute acid, and then added to the assay in a manner similar to the phosphate solution that is used to create the standard curve, a sample of which is shown in Table 5.

TABLE 5

Phosphate Standard Curve

| No. | Description | $PO_4$ Std. ($\mu l$) | 1.2N HCL ($\mu l$) | pmol P | Expected A660 nm |
| --- | --- | --- | --- | --- | --- |
| 1 | (blank)* | 0 | 300 | 0 | 0.02 |
| 2 | (blank)* | 0 | 300 | 0 | 0.02 |
| 3 | 10 $\mu M$ | 5 | 295 | 50 | 0.02 |
| 4 | 10 $\mu M$ | 10 | 290 | 100 | 0.03 |
| 5 | 10 $\mu M$ | 20 | 280 | 200 | 0.04 |
| 6 | 10 $\mu M$ | 30 | 270 | 300 | 0.06 |
| 7 | 20 $\mu M$ | 20 | 280 | 400 | 0.08 |
| 8 | 20 $\mu M$ | 25 | 275 | 500 | 0.10 |
| 9 | 20 $\mu M$ | 30 | 270 | 600 | 0.12 |
| 10 | 20 $\mu M$ | 35 | 265 | 700 | 0.14 |
| 11 | 20 $\mu M$ | 40 | 260 | 800 | 0.16 |
| 12 | 20 $\mu M$ | 50 | 250 | 1000 | 0.23 |
| 13 | 20 $\mu M$ | 60 | 240 | 1200 | 0.30 |
| 14 | 20 $\mu M$ | 80 | 220 | 1600 | 0.37 |
| 15 | 20 $\mu M$ | 100 | 200 | 2000 | 0.45 |

*Two blanks are averaged and subtracted from experimental readings.
Samples and controls are assayed using new borosilicate tubes.

Controls are precipitated and washed as above (in duplicate). Negative controls may comprise non-phosphorylated proteins, e.g. BSA, and positive controls may comprise phosphorylated proteins such as ovalbumin, which contains approximately 0.6 moles of phosphate per 0.74 moles of protein.

For the assay, 100 $\mu l$ ashing reagent (10% $MgNO_3$) is added to each TCA precipitate. The samples are warmed in a heating block at 70° C. for 10 min. and the the dried yellow pellet is carefully heated over a Bunsen flame until all brown smoke is gone and a white powder remains. The tube is placed in a metal rack to cool and then 300 $\mu l$ 1.2 N HCl and 100 $\mu l$ color reagent is added, mixed, transferred to a microcuvette and the optical density at 660 nm is determined and compared to a standard curve prepared from phosphate solutions of known concentration as described above.

Example 15

Construction of DNA-PK Substrate Vectors for Expression in E. coli

Construction of DNA-PK Substrate Vector Precursor

Figure 5A:
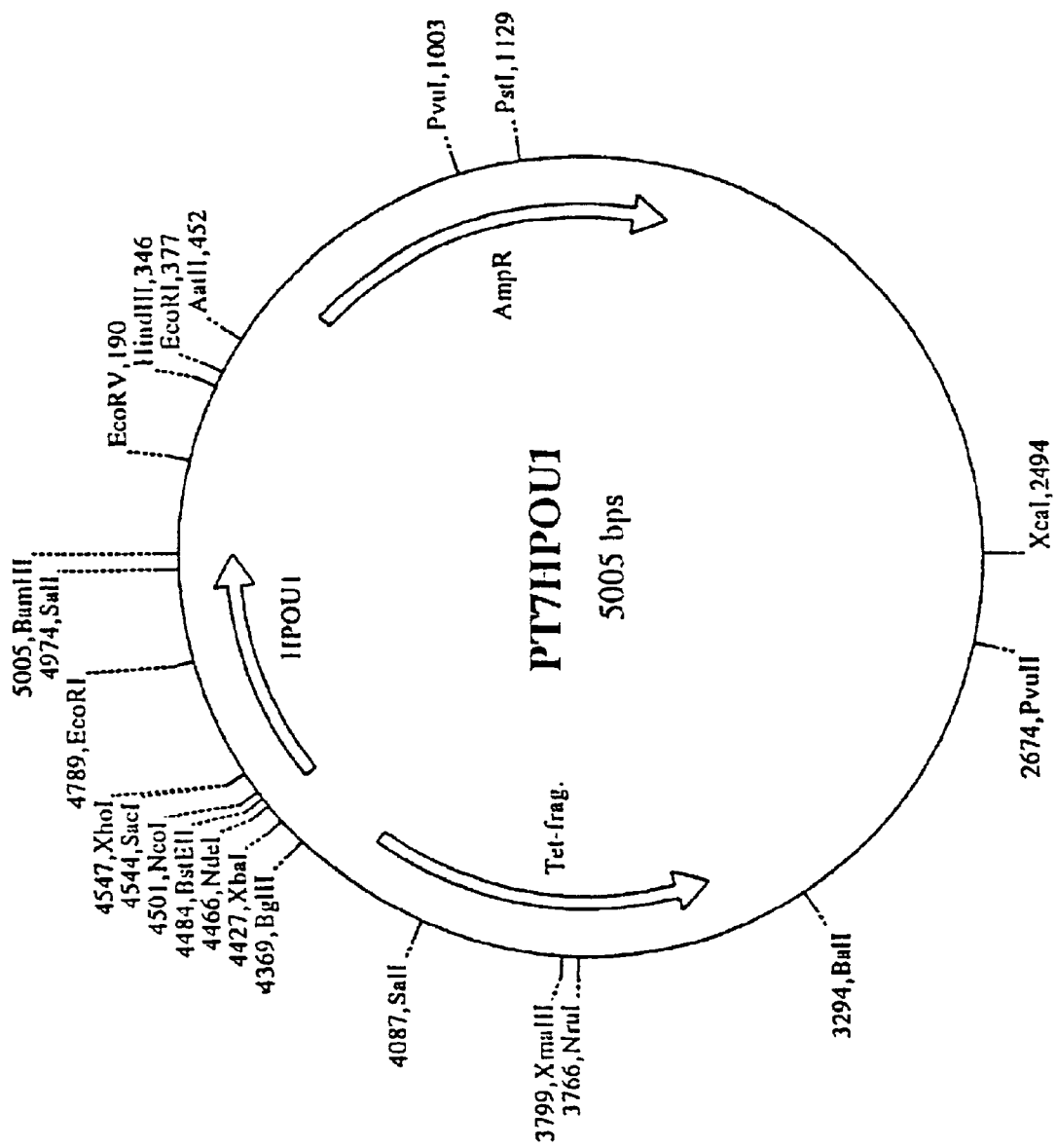
FIG. 5A is a map of plasmid pT7HPOU1.

The human Oct-1 POU domain gene was obtained in plasmid pET11cOCT1POU from R. Aurora and W. Herr (Cold Spring Harbor Laboratory) and moved into a derivative of the Novagen T7 plasmid vector pET-3, pT7HEP1DBP, as described (Anderson and Lees-Miller, 1992, Crit. Rev. in Eukaryotic Gene Expression, 2:283–314). The resulting plasmid was called pT7HPOU1 or p236. The predicted sequence is shown FIG. 5B. A map of which is shown FIG. 5A.

A plasmid with a mutation in the POU domain which prevents binding to DNA was obtained from W. Herr; this plasmid was referred to as p335. In this mutant, codon 49 of the POU domain was changed from arginine (Arg) to alanine (Ala), and the mutant POU domain was referred to as the R49A mutant. The R49A mutation also introduced a Hae III site in the gene. R49 (of the POU domain) is at amino acid position 79 of the nascent, wild-type, DNA-PK recombinant substrate shown in FIG. 8B.

A double stranded oligonucleotide segment that encodes the phosphorylation site segment Met Pro Glu Glu Ser Gln Glu Thr Phe Glu Asp Leu Trp Lys Leu Leu Pro Gly His His (SEQ ID NO:45) was prepared by annealing BNL oligonucleotides #2459 (forward) and #2458 (reverse) shown in Table 6.

The resulting PCR-generated fragment was cleaved with Xba I and BamH I and cloned into similarly cleaved p409 (pET-25b-derivative). The resulting plasmid was called p318 or p318SUB1.

Plasmid p318SUB1 has a Bsu36 I site and a Sal I site near the 3' end of the Xba I-BamH I substrate expression cassette; these sites were removed to facilitate subsequent cloning operations. The Oct-1/POU region of p318SUB1 was copied by PCR using primers #2602 and #2601, which are shown in Table 8. The nucleotide changes that removed the Bsu36 I and the Sal I sites are in the 3' antisense primer #2601.

TABLE 6

2459 Sense-strand oligonucleotide
5'-TATG<u>CCTGAGG</u>AAAGTCAGGAGACATTCGA<u>AGATCT</u>ATGGAAACTACTTCCTG-3'    (SEQ ID NO: 46)
     (CC|TGAGG) *Bsu*36 I        (A|GATCT) *Bgl* II

2458 Antisense-strand oligonucleotide
5'-GTGACCAGGAAGTAGTTTCCATAGATCTTCGAATGTGTCCTGACTTTCCTCAGGCA-3'    (SEQ ID NO: 47)

The annealed double stranded oligonucleotide had a 5' extension at the (SEQ ID NO: 46) 5' end that was compatible with an Nde I site (CA|TATG) and the (SEQ ID NO: 47) 5' end had an extension compatible with a BstE II site (G|GTNACC). A Bsu36 I site (CC|TGAGG) (at the Pro Glu codons) and a Bgl II site (A|GATCT) (at the AspLeu codons) were also present in the oligonucleotides at internal positions. The double stranded oligonucleotide (#2459:#2458) was cloned into Nde I and BstE II-cleaved p236 (pT7HPOU1) using standard techniques known in the art (Sambrook, et al., 1989, *Molecular Cloning: A Laboratory Manual*, Second Edition, Cold Spring Harbor Press, N.Y.). This intermediate construct was not given a name.

A derivative of pET-25b lacking a Bgl II site (Novagen) was constructed by cleaving pET-25b DNA with Bgl II, followed by treating the linearized plasmid with Klenow polymerase to fill in the site and with T4 Ligase to recircularize the plasmid. The resulting pET-25b derivative without a Bgl II site was called p409. A similar derivative of pET-28a DNA was subsequently prepared in an identical manner and designated p410.

Construction of Substrate Expression Cassettes

The segment encoding the Oct-1/POU sequence in the unnamed intermediate construct was copied using polymerase chain reaction (PCR). The primers were #2486 (5' sense-strand), #2485 (3' antisense strand) and the template DNA was the unnamed intermediate plasmid. The sequences of primers #2486 and 2485 are shown in Table 7.

TABLE 7

2486 5' sense primer with upstream untranslated segment and 5'Xba I
site for substrate PCR
5'-GCTCTAGAAAGTCGACTTTAAGAAGGAGATACCAAGATGCCTGAGGAAAGTCAG-3'    (SEQ ID NO: 46)

2485 3' Antisense primer with HSV epitope sequence and 3'BamH I site
for substrate PCR
5'-CGGGATCCTAATCCTCAGGGTCTTCCGGGGCGAGCTCTGGCTGTGGGTTGATTCTTTTTC-3'    (SEQ ID NO: 49)

Table 8

```
#2602 5' Sense-strand primer for substrate PCR.
5'-CATCACCATGGTATGAGCGGCGGCATGGAGGAGCCCAGTGACCTTG-3'          (SEQ ID NO: 50)
        (C|CATGG) Nco I

#2601 3' Antisense primer for substrate PCR.
5'-CGGGATCCTAATCCTCGGGGTCTTCCGGGGCGAGTTCTGGCTGTGGGTTGATTCTTTTTTC-3'  (SEQ ID NO: 51)
    BamH I ***Stop xBsu36 I        xSal I
```

The PCR-produced fragment was cleaved with Nco I (C|CATGG) and BamH I and cloned into similarly cleaved p318SUB1; the resulting plasmid is called p345 or p345SUB1. The non-expressing *E. coli* strain DH-S5α was transformed with this plasmid and designated strain CWABNL #345.

A derivative of p345SUB1 was prepared which does not bind DNA. The Oct-1/POU segment from plasmid p335, which contains the R49A mutation, was copied by PCR using primers #2601, #2602 and p335 DNA as template. The resulting fragment was cleaved with Nco I and BamH I as described above and cloned into similarly cleaved p318SUB1. This plasmid was designated p346 or p346SUB2. As with P345SUB1, P346SUB2 was also introduced to the non-expressing *E. coli* strain DH-5α.

Construction of Expression Vectors p349SUB1 and p350SUB2

Figure 8A:
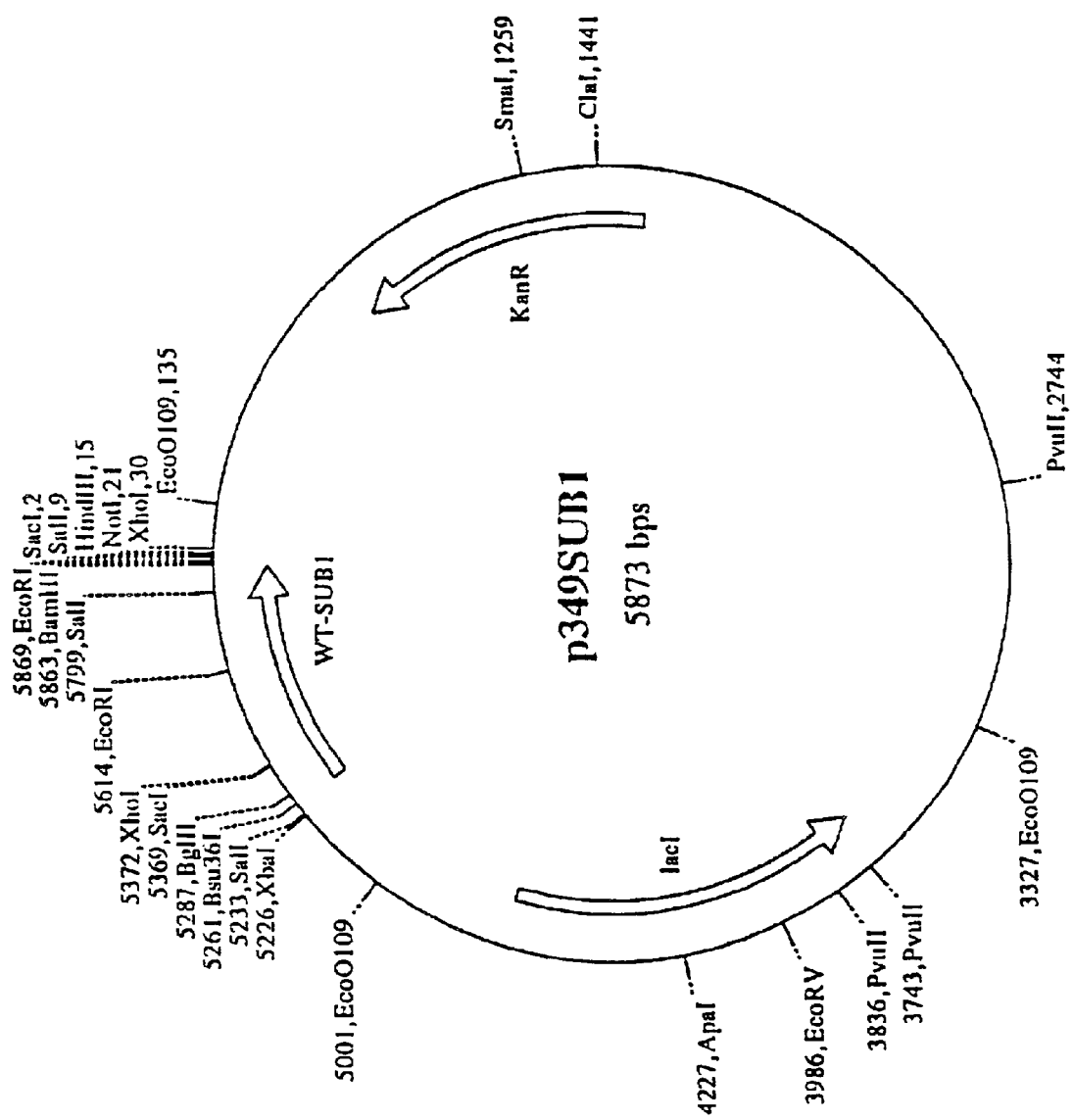
FIG. 8A is a map of plasmid p349SUB1.

The substrate expression cassettes from p345SUB1 and p346SUB2 were moved from the pET-25 background, which is selectable with the antibiotic ampicillin, to p410, a derivative of pET-28, which is selectable with 50 μg/ml of the antibiotic kanamycin. The Xba I-BamH I substrate cassettes were excised from p345 and p346 and cloned into Xba I and BamH I cleaved p410. The resulting plasmids were called p349SUB1 and p350SUB2, respectively. A map of plasmid p349SUB1 is shown in FIG. 8A. The predicted sequence for p3495SUB1 was designated Wild-Type Artificial DNA-PK substrate 1 and is shown in FIG. 8B.

Construction of Expression Vectors p355SUB3 and p357SUB5

To generate expression vector constructs that expressed negative control proteins, derivatives of p349SUB1 and p350SUB2 were prepared by replacing the serine residue codon at the phosphorylation site with the codon for the non-phosphorylated residue alanine (Ala). These recombinant negative control protein-expressing plasmids were constructed by replacing the short segment between the Bsu36 I and the Bgl II sites located in the p53 substrate phosphorylation site encoding segment of the p53 gene with a double stranded oligonucleotide prepared by annealing oligonucleotides #2738 and #2739. Oligonucleotides #2738 and #2739 are shown in Table 9. The mutation-containing fragment also has a diagnostic BstN I site (CC|WGG) which is not present in the wild-type substrate.

TABLE 9

2739 Synthetic substrate fragment to change sequence from Ser Gln Glu to Ala Gln Glu, sense strand.
Glu Glu Ala Gln Glu Thr Phe Glu (SEQ ID NO: 52)

TABLE 9-continued

5'-T GAG GAA GCC CAG GAG ACA TTC GAA-3' (SEQ ID NO: 53)
2738 Synthetic substrate fragment to change Ser Gln Glu site to Ala Gln Glu, antisense strand.
5'-GATCTTCGAATGTCTCCTGGGCTTCC-3' (SEQ ID NO: 54)

The resulting plasmids were designated p355SUB3 (wild-type Oct-1/POU domain) and p357SUB5 (R49A mutant Oct-1/POU domain), respectively.

Construction of Expression Vectors p356SUB4 and p358SUB6

In the same manner as described in the previous section, additional negative control-expressing vectors were prepared. Derivatives of p349SUB1 and p350SUB2 that had the sequence at the DNA-PK recognition site -Ser Gln Glu- changed to -Ser Glu Gln- were constructed. The Ser Glu Gln site in a peptide is not phosphorylated by DNA-PK. A replacement Bsu36 I-Bgl II fragment was prepared by annealing oligonucleotides #2740 and #2741 (Table 10). This fragment also has a diagnostic Ple I site (GAGTCNNN|).

TABLE 10

2741 Synthetic substrate fragment to change phosphorylation site sequence from the wild-type Ser Gln Glu to Ser Glu Gln, sense strand.
5'-TGAGGAGTCTGAGCAGACATTCGAA-3' (SEQ ID NO: 55)
2740 Synthetic substrate fragment to change phosphorylation site sequence from the wild-type Ser Gln Glu to Ser Glu Gln, antisense strand.
5'-GATCTTCGAATGTCTGCTCAGACTCC-3' (SEQ ID NO: 56)

The resulting plasmids were designated p356SUB4 (wild-type Oct-1/POU domain) and p358SUB6 (R49A mutant domain), respectively.

Confirmation of Recombinant Sequences

The expected nucleotide sequence for each gene encoding an artificial recombinant protein substrate and control protein was confirmed by DNA sequence analysis of the vectors and N-terminal protein sequence analyses of the expressed proteins. This was accomplished by sequencing one strand of the substrate-encoding region of each plasmid and by subjecting each of the purified proteins to automated Edman degradation using an Applied Biosystems 430A protein sequencer.

Expression of Artificial Substrate Encoding Genes

In order for expression of the encoded substrates to occur, each plasmid was transferred to the *E. coli* expression strain BL21(DE3). These transformed strains were designated:

351=p349SUB1 in BL-21(DE3): Artificial Substrate Expression Vector with Ser Gln Glu DNA-PK site and wild-type p53-Oct1/POU domain.

352=p350SUB2 in BL-21(DE3): Artificial Substrate Expression Vector with Ser Gln Glu DNA-PK site and R49A mutant p53-Oct1/POU DNA binding domain. POU domain has Hae III site that is not present in wild-type DNA.

386=p355SUB3 in BL-21(DE3): Control DNA-PK Artificial Substrate Expression Vector with Ala Gln Glu (S4A) "DNA-PK site" and wild-type DNA binding domain; p53 segment has BstN I site (CC|WGG) that is not in wild-type DNA.

387=p356SUB4 in BL-21 (DE3): Control DNA-PK Artificial Substrate Expression Vector with Ser Glu Gln "DNA-PK site" and wild-type DNA-binding domain; p53 segment has Pie I site that is not in wild-type DNA.

388=p357SUB5 in BL-21(DE3): Control DNA-PK Substrate Artificial Expression Vector with Ala Gln Glu (S4A) "DNA-PK site" and R49A mutant DNA-binding domain. Plasmid has BstN and Hae III sites that are not in wild-type plasmid.

389=p358SUB6 in BL-21(DE3): Control DNA-PK Artificial Substrate Expression Vector with Ser Glu Gln "DNA-PK site" and R49A mutant DNA-binding domain. Plasmid has Ple I and Hae III sites that are not in wild-type plasmid.

Each of the above strains produced an approximately 20 kDa polypeptide corresponding to the respective substrate following induction for expression with 1 mM IPTG (isopropyl-[β]-D-thiogalactopyranoside) using methods for cell growth and induction as described by Studier, et al. (*Met. Enz.*, 185:60–189, 1990). Each substrate was purified to >90% homogeneity from IPTG-induced *E. coli* cell lysates by Ni-affinity chromatography using a Pro-bond (Ni) resin (Invitrogen, Cat# R801-01, 3985 B Sorrento Valley Blvd, San Diego, Calif. 92121) according to the manufacturer's instructions.

Example 16

Characterization of Recombinant (artificial) Substrates Produced in *E. coli*

The recombinant protein substrates, a total of six, (at approximately 0.1 mg/ml final concentration) were separately mixed with hsp90 in a phosphorylation reaction with purified DNA-PK (0.6 pg, 0.02 units/assay) without (−) or with (+) 5 μg/ml calf thymus DNA, in the presence of $^{32}$P-ATP for 30 minutes at 30° C. as described by Lees-Miller, et al., *Mol. Cell. Biol.*, 12:5041–5049 (1992). The phosphorylation reactions were stopped with SDS sample buffer and analyzed with SDS-PAGE. The gel was fixed, stained with Coomassie brilliant blue, dried and developed by autoradiographic procedures. The results of which can be seen in FIG. 9. The upper panel of FIG. 9 shows the phosphoimage (Molecular Dynamics, 880 East Arques Ave Sonnyvale, Calif. 94086) of the gel, revealing the transfer of $^{32}$PO$_4$ to the control protein (hsp90) and to the recombinant artificial substrate protein (rSub); the two lower panels show Coomassie blue stain images of regions corresponding to hsp90 and the recombinant substrates.

Figure 9:
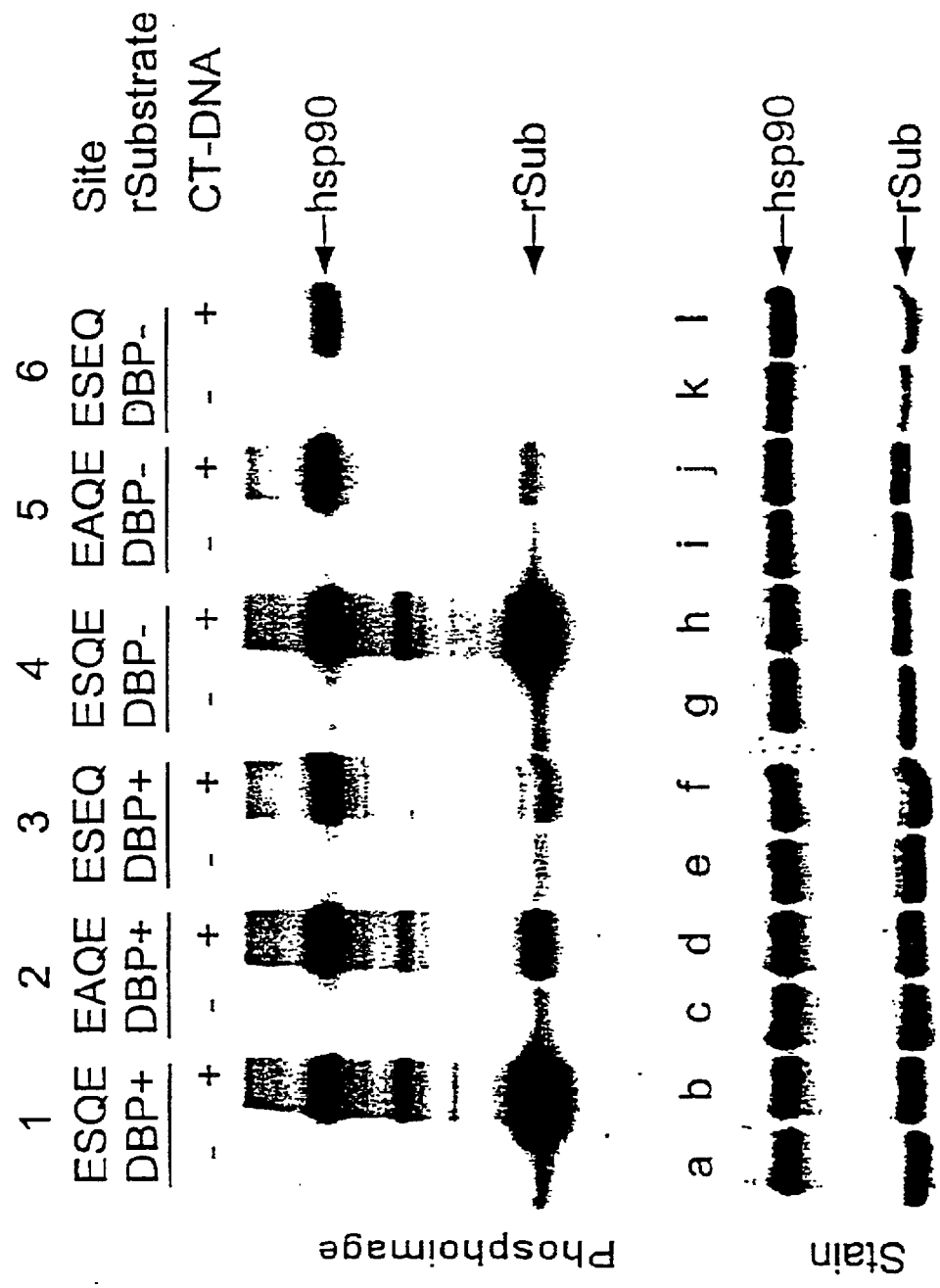
FIG. 9 depicts the phosphorylation of recombinant protein substrates by purified human DNA-PK as analyzed by SDS-PAGE. The upper portion is a phosphorimage of the gel; the lower portion is two panels showing Coomassie blue stained images of regions corresponding to hsp90 and the recombinant substrates respectively.

As would be apparent to one skilled in the art, FIG. 9 shows the recombinant substrates behaved as expected with respect to phosphorylation by purified DNA-PK. The wild-type recombinant DNA-PK substrate (1 ESQE-DBP+) was phosphorylated in a DNA-dependent manner equal to, if not better than, hsp90 (a known DNA-PK substrate). Furthermore, a 20fold increase in phosphate incorporation into both substrates was observed by the addition of double stranded DNA compared to no addition of DNA.

Substrates containing mutant DNA-PK phosphorylation sites with the serine changed to alanine, i.e., substrates 2 and 5, were phosphorylated to less than 5% of the level of the wild-type substrate. Also, substrates containing mutant DNA-PK phosphorylations sites with the glutamine-glutamic acid amino acids inverted, i.e., substrates 3 and 6, were phosphorylated to less than 5% of the level of the wild-type substrate (substrate 1). Substrate 4, which contains the mutant POU DNA-binding domain, was phosphorylated to 50% of the level of the wild-type substrate, i.e., substrate 1. A large difference in the phosphorylation of the substrates was not expected since calf thymus DNA had been used for DNA-PK activation (not the specific Oct-i binding fragment of the substrate) and the substrate concentrations were relatively high. These control results show that the wild-type recombinant substrate is phosphorylated predominantly at one site by DNA-PK and this site corresponds to the SQ (Ser Gln) site corresponding to the human p53 serine 15 site.

Isoelectrofocusing Analysis of Recombinant DNA-PK Substrates

Samples of the purified wild-type and control recombinant DNA-PK substrates, approximately 1 μg each, were analyzed on a slab isoelectric focusing gel prepared with Bio-Lyte 5/7 ampholytes (Bio-Rad) and urea as described by Copeland (1994). The gel was focused at 100 volts for approximately 30 minutes, then at 200 volts for approximately 4 hours. The scanned image of the Coomassie blue stained gel is shown in FIG. 10.

Figure 10:
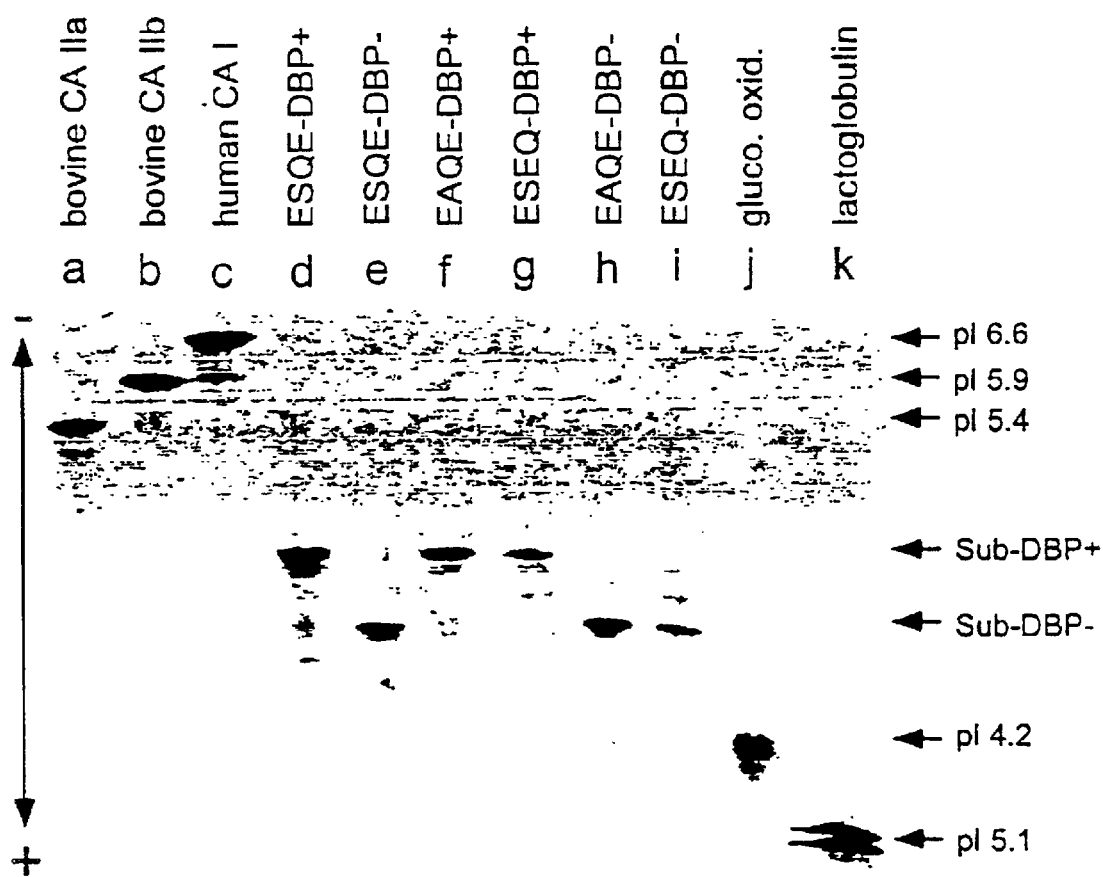
FIG. 10 depicts a Coomassie blue stained gel of the recombinant substrates of the present invention analyzed by isoelectrofocusing gel electrophoresis.

The samples and markers are shown in FIG. 10 in the following manner: a) bovine erythrocyte carbonic anhydrase II, pI 5.4 isoform, b) bovine erythrocyte carbonic anhydrase II, pI 5.9 isoform, c) human erythrocyte carbonic anhydrase I, pI 6.6 isoform; d) wild-type recombinant substrate (ESQE-DBP+) (substrate 1); e) control substrate with wild-type DNA-PK site and mutant POU DNA-binding domain (ESQE-DBP−) (substrate 4); f) control substrate with alanine substituted for serine at the DNA-PK site (EAQE-DBP+) (substrate 2); g) control substrate with the glutamine-glutamic acid pair at the DNA-PK site inverted (ESEQ-DBP+) (substrate 3); h) control substrate with alanine mutation and a mutant POU domain (EAQE-DBP−) (substrate 5); i) control substrate with QE inversion and a mutant POU domain (ESEQ-DBP−) (substrate 6); j) glucose oxidase from *A. nigers*; and k) bovine lactoglobulin. The pI values listed at the right side of FIG. 10 are for the markers as the native proteins. The markers pI values are those specified by the supplier.

As shown in FIG. 10, the recombinant protein substrates focused primarily as single electrophoretic species with pIs (isoelectric points) near 5, as expected from the sequences of the substrate. The wild-type and mutant POU domain substrates focused at distinct positions that are baseline resolved. It is believed that this difference is a consequence of a charge change resulting from the substitution of alanine for arginine in the mutant POU domain. One skilled in the art would predict a singly phosphorylated wild-type substrate would focus at a lower position than the substrates with the mutant POU domain because phosphate provides two negative charges.

A parallel experiment was also conducted (data not shown) in which the substrates were electrophoretically transferred from the isoelectric focusing gel to a PVDF membrane. The substrates were then detected with an antibody specific for the C-terminal HSV epitope. Based upon this experiment, the phosphorylated and unphosphorylated substrates could be readily distinguished.

Example 17

Figure 6:
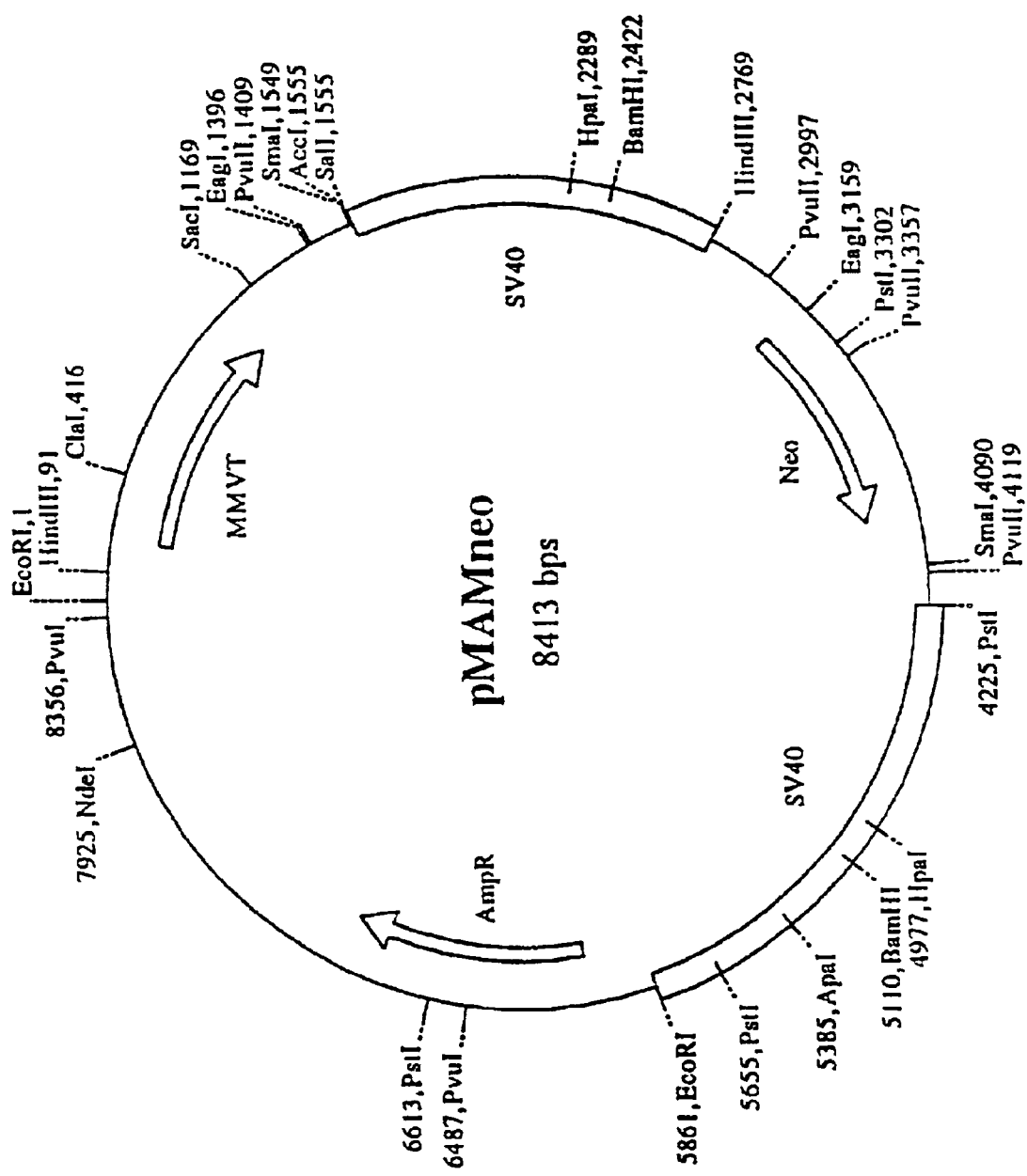
FIG. 6 is a map of plasmid pMAMneo.

Construction of Mammalian Cell Expression Vectors Containing Substrate Cassettes The substrate cassettes produced in Example 15 were also moved to a vector suitable for expression in mammalian cells. The vector pMAMneo, (Clontech Cat #6104-1, 400 Fabian Way, Palo Alto, Calif. 94303-4607), was chosen for expressing the substrate cassettes in eukaryotic cells. The vector pMAMneo is a well characterized vector for expressing genes in eukaryotic cells. The vector contains a gene for neomycin resistance. Thus, retention of plasmid sequences can be selected with the antibiotic G-418. The gene to be expressed is placed under control of the mouse mammary tumor virus promoter, which is expressed at low levels in the absence of an inducer and expressed at high levels after the addition of dexamethasone inducer. A map of pMAMneo is shown in FIG. 6.

To convert pMAMneo into a vector suitable for accepting the artificial substrate expression casette (the Xba I-Not I fragments from the plasmids of Example 15), the pMAMneo multiple cloning segment (MCS), which contains sites for Nhe I (G|CTAGC), Sma I (CCC|GGG), Sal I (G|TCGAC), and Xho I (C|TCGAG), was altered to include a Xba I site, a Not I site, and other sites which are shown in Table 11.

The pMAMneo DNA was cleaved with Nhe I and Xho I and the intervening fragment was replaced with a double stranded oligonucleotide prepared from oligonucleotides #2736 (sense-strand) and #2736 (antisense-strand), which are shown in Table 11.

TABLE 11

Figure 6A:
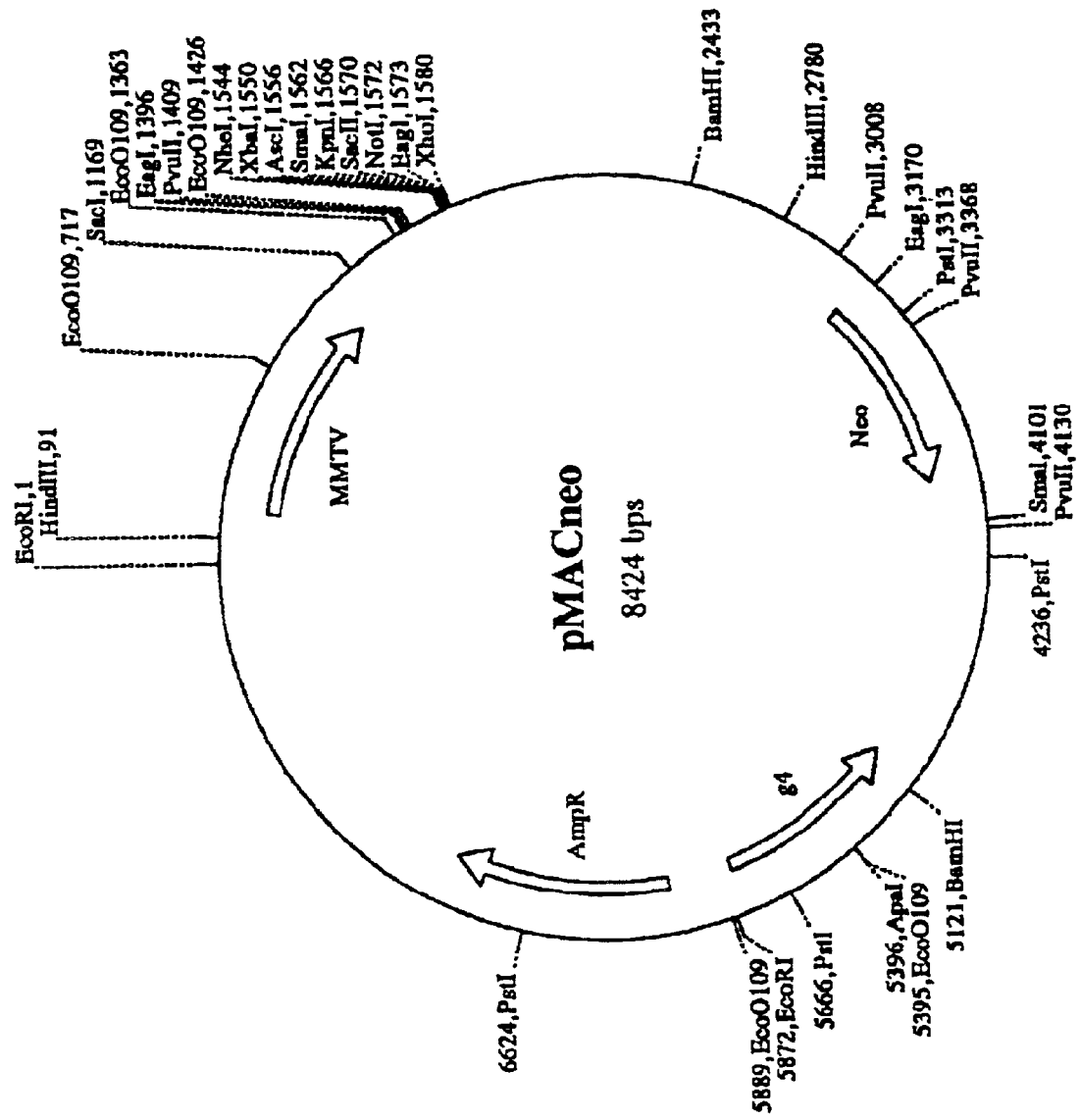
FIG. 6A is a map of plasmid pMACneo.
Figure 7:
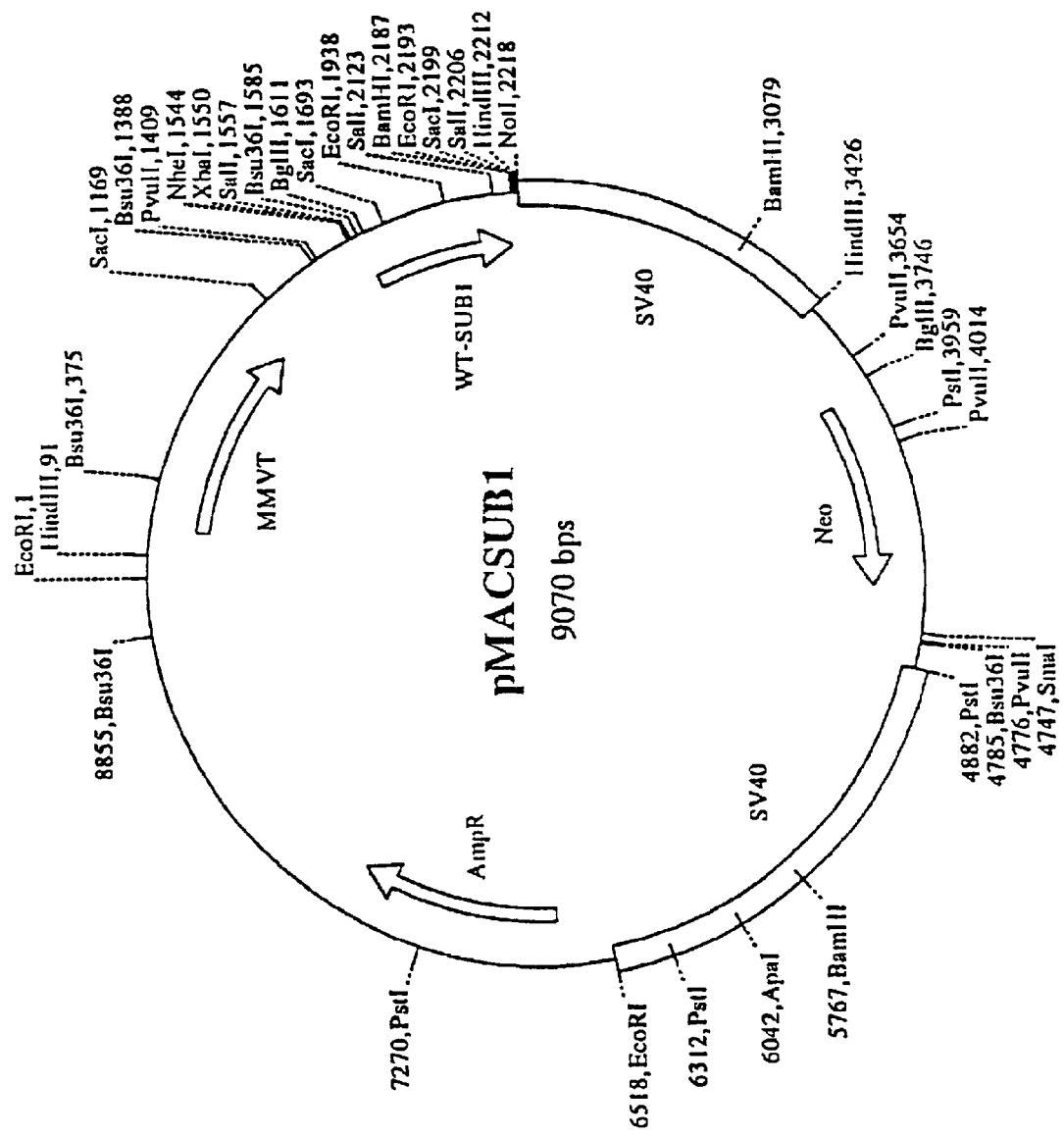
FIG. 7 is a map of plasmid pMACSUB1.
Figure 11:
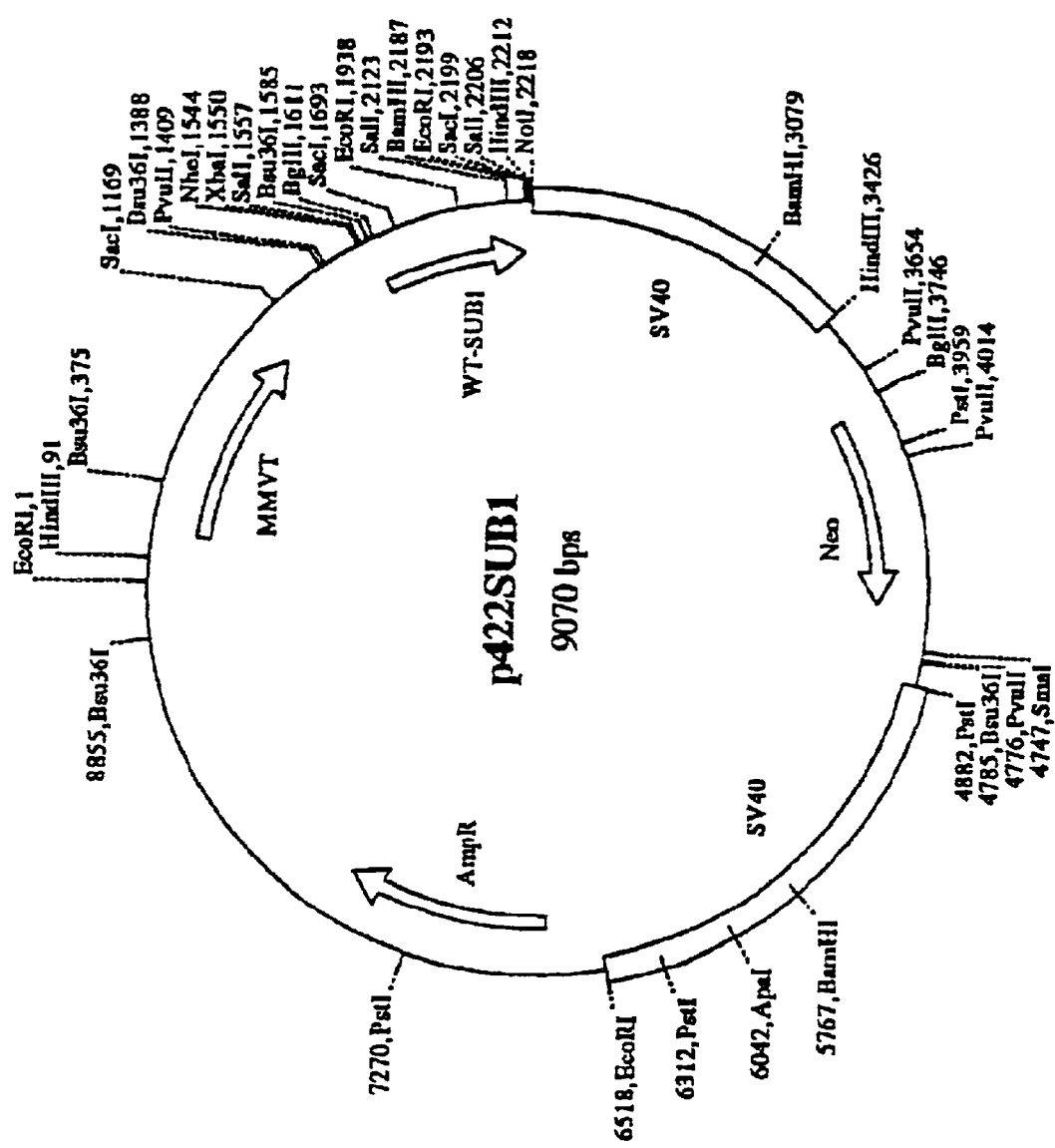
FIG. 11 is a map of plasmid p422SUB1 which encodes the DNA-PK wild-type substrate (SEQ ID NO: 61).

2736 pMAMneo MCS expansion oligonucleotide, sense-strand.
5'-CTAGCTCTAGAGGCGCGCCCGGGTACCGCGGCCGCC-3' (SEQ ID NO: 57)
2737 pMAMneo MCS expansion oligonucleotide, antisense-strand).
5'-TCGAGGCGGCCGCGGTACCCGGGCGCGCCTCTAGAG-3' (SEQ ID NO: 58)
Annealed oligonucleotide and restriction sites:
5'-CTAGCTCTAGAGGCGCGCCCGGGTACCGCGGCCGCC-3' (SEQ ID NO: 57)
    3'-GAGATCTCCGCGCGGGCCCATGGCGCCGGCGGAGCT-5' (SEQ ID NO: 58)
    NheI XbaI AscI SmaI KpnI SacII NotI XhoI The resulting vector was designated p354 (pMACneo) and the MCS region contains sites for the following restriction enzymes: Nde I (G|CTAGC), Xba I (T|CTAGA), Asc I (GG|CGCGCC), Sma I (CCC|GGG), Kpn I (CCATG|G), Sac I (CCGC|GG), Not I (GC|GGCCGC), and Xho I (C|TCGAG) (FIG. 4: pMACneo plasmid map). A map of p354 (pMACneo) is shown in FIG. 6A.

pMACneo DNA was cleaved with Xba I and Not I. The resulting vector fragment was ligated with the xba I-Not I fragments from each of the substrate vectors. The resulting mammalian substrate expression vectors were designated: p422SUB1 (derivative of p349SUB1), p423SUB2 (derivative of p350SUB2), p424SUB3 (derivative of p355SUB3), p425SUB4 (derivative of p356SUB4), p426SUB5 (derivative of p357SUB5), p427SUB6 (derivative of p358SUB6). A plasmid map of p422SUB1, expressing the wild-type substrate, is shown in FIG. 11.

Introduction of the expression vectors into eukaryotic cells, followed by induction of expression of the protein substrates and negative control proteins facilitates the study of PNA-PK activity in the living cells.

While described here are what presently is believed to be the preferred embodiments of the invention, those skilled in the art will realize that changes and modifications may be made to the present invention without departing from the spirit of the invention, and it is intended to claim all such changes and modifications.

What is claimed is:

1. A composition useful for detecting and quantitating DNA-activated protein kinase (DNA-PK) activity in a biological sample comprising a synthetic peptide substrate selected from the group consisting of Glu Pro Pro Leu Ser Gln Glu Ala Phe Ala Asp Leu Trp Lys Lys (SEQ ID NO: 11), Glu Pro Pro Gln Ser Gln Glu Ala Phe Ala Asp Leu Trp Lys Lys (SEQ ID NO: 15), Glu Pro Pro Leu Thr Gln Glu Ala Phe Ala Asp Leu Trp Lys Lys (SEQ ID NO: 16), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19).

2. A kit for detecting and quantitating DNA-activated protein kinase (DNA-PK) activity, comprising:

(a) a phosphate donor;

(b) a composition useful for detecting and quantitating DNA-activated protein kinase (DNA-PK) activity in a biological sample comprising a synthetic peptide substrate selected from the group consisting of Glu Pro Pro Leu Ser Gln Glu Ala Phe Ala Asp Leu Trp Lys Lys (SEQ ID NO: 11), Glu Pro Pro Gln Ser Gln Glu Ala Phe Ala Asp Leu Trp Lys Lys (SEQ ID NO: 15), Glu Pro Pro Leu Thr Gln Glu Ala Phe Ala Asp Leu Trp Lys Lys (SEQ ID NO: 16), Pro Glu Glu Ser Gln Glu Ala Phe Ala Asp Leu Trp Lys Lys (SEQ ID NO: 18) and Pro Glu Ser Gln Glu Ala Phe Ala Asp Leu Trp Lys Lys (SEQ ID NO: 19); and (c) a means for detecting a phosphorylated synthetic peptide substrate, whereby detection of said phosphorylated synthetic peptide substrate is utilized to determine an amount of DNA-PK activity in said biological sample.

3. The kit of claim 2, wherein said phosphate donor is ATP.

4. The kit of claim 2, further including a negative control peptide selected from the group consisting of Glu Pro Pro Leu Ser Glu Gln Ala Phe Ala Asp Leu Trp Lys Lys (SEQ ID NO: 20), Pro Glu Ser Glu Gln Ala Phe Ala Asp Leu Trp Lys Lys (SEQ ID NO: 23), Glu Pro Pro Leu Ala Gln Glu Ala Phe Ala Asp Leu Trp Lys Lys (SEQ ID NO: 21), Pro Glu Glu Ala Gln Glu Ala Phe Ala Asp Leu Trp Lys Lys (SEQ ID NO: 24) and Pro Glu Glu Ser Glu Gln Ala Phe Ala Asp Leu Trp Lys Lys (SEQ ID NO: 25).

5. The kit of claim 2, further including buffers.

6. The kit of claim 2, further including a preparation of DNA-PK.

7. The kit of claim 2, further including a reagent to detect a phosphorylated peptide substrate.

* * * * *

UNITED STATES PATENT AND TRADEMARK OFFICE
CERTIFICATE OF CORRECTION

PATENT NO. : 6,803,203 B1
DATED : October 12, 2004
INVENTOR(S) : Carl W. Anderson It is certified that error appears in the above-identified patent and that said Letters Patent is hereby corrected as shown below:

<u>Title page,</u>
Item [75], Inventors, delete named inventor "Marjery A. Connelly".

Signed and Sealed this

Eighth Day of February, 2005

JON W. DUDAS
*Director of the United States Patent and Trademark Office*

SEQUENCE LISTING

<160> NUMBER OF SEQ ID NOS: 64

<210> SEQ ID NO 1
<211> LENGTH: 28
<212> TYPE: PRT
<213> ORGANISM: Homo sapiens
<220> FEATURE:
<221> NAME/KEY: MISC_FEATURE
<223> OTHER INFORMATION: Human p53 residues 1-28

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu
            20                  25

<210> SEQ ID NO 2
<211> LENGTH: 28
<212> TYPE: PRT
<213> ORGANISM: Musca domestica
<220> FEATURE:
<221> NAME/KEY: MISC_FEATURE
<223> OTHER INFORMATION: Mourse p53 residues 4-31

<400> SEQUENCE: 2

Met Glu Glu Ser Gln Ser Asp Ile Ser Leu Glu Leu Pro Leu Ser Gln
1               5                   10                  15

Glu Thr Phe Ser Gly Leu Trp Lys Leu Leu Pro Pro
            20                  25

<210> SEQ ID NO 3
<211> LENGTH: 16
<212> TYPE: PRT
<213> ORGANISM: Musca domestica
<220> FEATURE:
<221> NAME/KEY: MISC_FEATURE
<223> OTHER INFORMATION: Mouse p53 residues 4-13

<400> SEQUENCE: 3

Met Glu Glu Ser Gln Ser Asp Ile Ser Leu Glu Leu Pro Tyr Lys Lys
1               5                   10                  15

<210> SEQ ID NO 4
<211> LENGTH: 25
<212> TYPE: PRT
<213> ORGANISM: Homo sapiens
<220> FEATURE:
<221> NAME/KEY: MISC_FEATURE
<223> OTHER INFORMATION: Human p53 residues 1-24

<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Lys
            20                  25

<210> SEQ ID NO 5
<211> LENGTH: 25
<212> TYPE: PRT
<213> ORGANISM: Homo sapiens
<220> FEATURE:
<221> NAME/KEY: MISC_FEATURE
<223> OTHER INFORMATION: Human p53 residues 1-24; S15A substitution

<400> SEQUENCE: 5

-continued

Met Glu Glu Pro Gln Ser Asp Pro Ser Val Glu Pro Pro Leu Ala Gln
1               5                   10                  15

Glu Thr Phe Ser Asp Leu Trp Lys Lys
            20                  25

<210> SEQ ID NO 6
<211> LENGTH: 18
<212> TYPE: PRT
<213> ORGANISM: Homo sapiens
<220> FEATURE:
<221> NAME/KEY: MISC_FEATURE
<223> OTHER INFORMATION: Human p53 residues 29-44

<400> SEQUENCE: 6

Asn Asn Val Leu Ser Pro Leu Pro Ser Gln Ala Met Asp Asp Leu Met
1               5                   10                  15

Lys Lys

<210> SEQ ID NO 7
<211> LENGTH: 16
<212> TYPE: PRT
<213> ORGANISM: Homo sapiens
<220> FEATURE:
<221> NAME/KEY: MISC_FEATURE
<223> OTHER INFORMATION: Human p53 residues 160-175

<400> SEQUENCE: 7

Met Ala Ile Tyr Lys Gln Ser Gln His Met Thr Glu Val Val Arg Arg
1               5                   10                  15

<210> SEQ ID NO 8
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24

<400> SEQUENCE: 8

Glu Pro Pro Leu Ser Gln Glu Thr Phe Ser Asp Leu Trp Lys Lys
1               5                   10                  15

<210> SEQ ID NO 9
<211> LENGTH: 11
<212> TYPE: PRT
<213> ORGANISM: Homo sapiens
<220> FEATURE:
<221> NAME/KEY: MISC_FEATURE
<223> OTHER INFORMATION: Human p53 residues 11-19

<400> SEQUENCE: 9

Glu Pro Pro Leu Ser Gln Glu Thr Phe Lys Lys
1               5                   10

<210> SEQ ID NO 10
<211> LENGTH: 13
<212> TYPE: PRT
<213> ORGANISM: Homo sapiens
<220> FEATURE:
<221> NAME/KEY: MISC_FEATURE
<223> OTHER INFORMATION: Human p53 residues 11-21

<400> SEQUENCE: 10

Glu Pro Pro Leu Ser Gln Glu Thr Phe Ser Asp Lys Lys
1               5                   10

```
<210> SEQ ID NO 11
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:T18A and S20A
      substitutions

<400> SEQUENCE: 11

Glu Pro Pro Leu Ser Gln Glu Ala Phe Ala Asp Leu Trp Lys Lys
1               5                   10                  15

<210> SEQ ID NO 12
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:T18A and S20A and W23L
      substitutions

<400> SEQUENCE: 12

Glu Pro Pro Leu Ser Gln Glu Ala Phe Ala Asp Leu Leu Lys Lys
1               5                   10                  15

<210> SEQ ID NO 13
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:E17K, T18A and S20A
      substitutions

<400> SEQUENCE: 13

Glu Pro Pro Leu Ser Gln Lys Ala Phe Ala Asp Leu Trp Lys Lys
1               5                   10                  15

<210> SEQ ID NO 14
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:L14Q, Q16L, T18A and
      S20A substitutions

<400> SEQUENCE: 14

Glu Pro Pro Gln Ser Leu Glu Ala Phe Ala Asp Leu Trp Lys Lys
1               5                   10                  15

<210> SEQ ID NO 15
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:L14Q, T18A and S20A
      substitutions

<400> SEQUENCE: 15

Glu Pro Pro Gln Ser Gln Glu Ala Phe Ala Asp Leu Trp Lys Lys
1               5                   10                  15

<210> SEQ ID NO 16
<211> LENGTH: 15
<212> TYPE: PRT
```

-continued

```
<213> ORGANISM: Homo sapiens
<220> FEATURE:
<221> NAME/KEY: MISC_FEATURE
<223> OTHER INFORMATION: Human p53 residues 11-24:S15T, T18A and S20A
      substitutions

<400> SEQUENCE: 16

Glu Pro Pro Leu Thr Gln Glu Ala Phe Ala Asp Leu Trp Lys Lys
1               5                   10                  15

<210> SEQ ID NO 17
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:L14D, T18A and S20A
      substitutions

<400> SEQUENCE: 17

Glu Pro Pro Asp Ser Gln Glu Ala Phe Ala Asp Leu Trp Lys Lys
1               5                   10                  15

<210> SEQ ID NO 18
<211> LENGTH: 14
<212> TYPE: PRT
<213> ORGANISM: Homo sapiens
<220> FEATURE:
<221> NAME/KEY: MISC_FEATURE
<223> OTHER INFORMATION: Human p53 residues 12-24:P13E, L14E, T18A and
      S20A substitutions

<400> SEQUENCE: 18

Pro Glu Glu Ser Gln Glu Ala Phe Ala Asp Leu Trp Lys Lys
1               5                   10

<210> SEQ ID NO 19
<211> LENGTH: 13
<212> TYPE: PRT
<213> ORGANISM: Homo sapiens
<220> FEATURE:
<221> NAME/KEY: MISC_FEATURE
<223> OTHER INFORMATION: Human p53 residues 13-24:L13P, S14E, T18A and
      S20A substitutions

<400> SEQUENCE: 19

Pro Glu Ser Gln Glu Ala Phe Ala Asp Leu Trp Lys Lys
1               5                   10

<210> SEQ ID NO 20
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24 with Q16E, E17Q, T18A
      and S20A substitutions

<400> SEQUENCE: 20

Glu Pro Pro Leu Ser Glu Gln Ala Phe Ala Asp Leu Trp Lys Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: DNA-PK assay negative control peptide
```

```
<400> SEQUENCE: 21

Glu Pro Pro Leu Ala Gln Glu Ala Phe Ala Asp Leu Trp Lys Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: DNA-PK assay negative control peptide

<400> SEQUENCE: 22

Glu Pro Pro Leu Ala Gln Glu Thr Phe Ser Asp Leu Trp Lys Lys
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: DNA-PK assay negative control peptide

<400> SEQUENCE: 23

Pro Glu Ser Glu Gln Ala Phe Ala Asp Leu Trp Lys Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: DNA-PK assay negative control peptide

<400> SEQUENCE: 24

Pro Glu Glu Ala Gln Glu Ala Phe Ala Asp Leu Trp Lys Lys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: DNA-PK assay negative control peptide

<400> SEQUENCE: 25

Pro Glu Glu Ser Glu Gln Ala Phe Ala Asp Leu Trp Lys Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Example of inappropriate DNA-PK negative
      control peptide

<400> SEQUENCE: 26

Pro Glu Glu Ala Gln Glu Thr Phe Ser Asp Leu Trp Lys Lys
1               5                   10

<210> SEQ ID NO 27
<211> LENGTH: 24
<212> TYPE: DNA
<213> ORGANISM: Artificial Sequence
<220> FEATURE:
<223> OTHER INFORMATION: DNA effector for in vitro DNA-PK assays
```

-continued

```
<400> SEQUENCE: 27
gcgcgcgcgc gcgcgcgcgc gcgc                                           24

<210> SEQ ID NO 28
<211> LENGTH: 19
<212> TYPE: PRT
<213> ORGANISM: Homo sapiens
<220> FEATURE:
<221> NAME/KEY: MISC_FEATURE
<223> OTHER INFORMATION: Human p53 residues 92-108

<400> SEQUENCE: 28

Pro Leu Ser Ser Ser Val Pro Ser Gln Lys Thr Tyr Gln Gly Ser Tyr
1               5                   10                  15

Gly Lys Lys

<210> SEQ ID NO 29
<211> LENGTH: 21
<212> TYPE: PRT
<213> ORGANISM: Homo sapiens
<220> FEATURE:
<221> NAME/KEY: MISC_FEATURE
<223> OTHER INFORMATION: Human p53 residues 306-327

<400> SEQUENCE: 29

Ala Leu Pro Asn Asn Thr Ser Ser Ser Pro Gln Pro Lys Lys Lys Pro
1               5                   10                  15

Leu Asp Gly Glu Tyr
            20

<210> SEQ ID NO 30
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 371-385

<400> SEQUENCE: 30

Ser Lys Lys Gly Gln Ser Thr Ser Arg His Lys Lys Leu Met Phe
1               5                   10                  15

<210> SEQ ID NO 31
<211> LENGTH: 14
<212> TYPE: PRT
<213> ORGANISM: Homo sapiens
<220> FEATURE:
<221> NAME/KEY: MISC_FEATURE
<223> OTHER INFORMATION: Human p53 residues 380-393

<400> SEQUENCE: 31

His Lys Lys Leu Met Phe Lys Thr Glu Gly Pro Asp Ser Asp
1               5                   10

<210> SEQ ID NO 32
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:Q16E, T18A and S20A
      substitutions

<400> SEQUENCE: 32

Glu Pro Pro Leu Ser Glu Glu Ala Phe Ala Asp Leu Trp Lys Lys
1               5                   10                  15
```

```
<210> SEQ ID NO 33
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24:Q16N, T18A and S20A
      substitutions

<400> SEQUENCE: 33

Glu Pro Pro Leu Ser Asn Glu Ala Phe Ala Asp Leu Trp Lys Lys
1               5                   10                  15

<210> SEQ ID NO 34
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human p53 residues 11-24 with Q16Y, T18A, S20A
      and W23L substitutions

<400> SEQUENCE: 34

Glu Pro Pro Leu Ser Tyr Glu Ala Phe Ala Asp Leu Leu Lys Lys
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Synthetic Casein kinase I substrate

<400> SEQUENCE: 35

Asp Asp Asp Glu Glu Ser Ile Thr Arg Arg
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic S6 kinase substrate

<400> SEQUENCE: 36

Arg Arg Leu Ser Ser Leu Arg Ala
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic casein kinase II substrate

<400> SEQUENCE: 37

Arg Arg Arg Glu Glu Glu Thr Glu Glu Glu
1               5                   10

<210> SEQ ID NO 38
<211> LENGTH: 4
<212> TYPE: PRT
<213> ORGANISM: Artificial Sequence
<220> FEATURE:
<221> NAME/KEY: MISC_FEATURE
<223> OTHER INFORMATION: peptide fragement
```

```
<400> SEQUENCE: 38

Ser Asp Leu Trp
1

<210> SEQ ID NO 39
<211> LENGTH: 10
<212> TYPE: PRT
<213> ORGANISM: Artificial Sequence
<220> FEATURE:
<223> OTHER INFORMATION: Synthetic casein kinase II substrate

<400> SEQUENCE: 39

Arg Arg Arg Asp Asp Asp Ser Asp Asp Asp
1               5                   10

<210> SEQ ID NO 40
<211> LENGTH: 17
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: human hsp90 residues 1-4
<221> NAME/KEY: MISC_FEATURE
<222> LOCATION: (5)..(17)
<223> OTHER INFORMATION: human p53 residues 15-27 with S20E
      substitution

<400> SEQUENCE: 40

Met Pro Glu Glu Ser Gln Glu Thr Phe Glu Asp Leu Trp Lys Leu Leu
1               5                   10                  15

Pro

<210> SEQ ID NO 41
<211> LENGTH: 4
<212> TYPE: PRT
<213> ORGANISM: Homo sapiens
<220> FEATURE:
<221> NAME/KEY: MISC_FEATURE
<223> OTHER INFORMATION: human hsp90 residues 1-4

<400> SEQUENCE: 41

Met Pro Glu Glu
1

<210> SEQ ID NO 42
<211> LENGTH: 13
<212> TYPE: PRT
<213> ORGANISM: Homo sapiens
<220> FEATURE:
<221> NAME/KEY: MISC_FEATURE
<223> OTHER INFORMATION: human p53 residues 15 to 27 with S20E
      substitution

<400> SEQUENCE: 42

Ser Gln Glu Thr Phe Ser Asp Leu Trp Lys Leu Leu Pro
1               5                   10

<210> SEQ ID NO 43
<211> LENGTH: 11
<212> TYPE: PRT
<213> ORGANISM: herpes simplex virus 1
<220> FEATURE:
<221> NAME/KEY: MISC_FEATURE
<223> OTHER INFORMATION: HSV 1 glycoprotein D precursor residues 289-299

<400> SEQUENCE: 43
```

```
Glu Pro Glu Leu Ala Pro Glu Asp Pro Glu Asp
1               5                  10
```

```
<210> SEQ ID NO 44
<211> LENGTH: 4
<212> TYPE: PRT
<213> ORGANISM: Artificial Sequence
<220> FEATURE:
<223> OTHER INFORMATION: Consensus cleavage site of human adenovirus
      endoproteinase

<400> SEQUENCE: 44
```

```
Met Ser Gly Gly
1
```

```
<210> SEQ ID NO 45
<211> LENGTH: 20
<212> TYPE: PRT
<213> ORGANISM: Artificial Sequence
<220> FEATURE:
<223> OTHER INFORMATION: Synthetic phosphorylation site segment

<400> SEQUENCE: 45
```

```
Met Pro Glu Glu Ser Gln Glu Thr Phe Glu Asp Leu Trp Lys Leu Leu
1               5                   10                  15
Pro Gly His His
            20
```

```
<210> SEQ ID NO 46
<211> LENGTH: 53
<212> TYPE: DNA
<213> ORGANISM: Artificial Sequence
<220> FEATURE:
<223> OTHER INFORMATION: Sense strand oligonucleotide encoding DNA-
      PKphosphorylation segment SEQ ID NO: 45

<400> SEQUENCE: 46
tatgcctgag gaaagtcagg agacattcga agatctatgg aaactacttc ctg          53
```

```
<210> SEQ ID NO 47
<211> LENGTH: 56
<212> TYPE: DNA
<213> ORGANISM: Artificial Sequence
<220> FEATURE:
<223> OTHER INFORMATION: Antisense oligonucleotide for phosphorylation
      site segment

<400> SEQUENCE: 47
gtgaccagga agtagtttcc atagatcttc gaatgtgtcc tgactttcct caggca       56
```

```
<210> SEQ ID NO 48
<211> LENGTH: 53
<212> TYPE: DNA
<213> ORGANISM: Artificial Sequence
<220> FEATURE:
<223> OTHER INFORMATION: Sense primer sequence

<400> SEQUENCE: 48
gctctagaag tcgactttaa gaaggagata ccaagatgcc tgaggaaagt cag          53
```

```
<210> SEQ ID NO 49
<211> LENGTH: 61
<212> TYPE: DNA
<213> ORGANISM: Artificial Sequence
<220> FEATURE:
<223> OTHER INFORMATION: Antisense primer with HSV epitope sequence
```

-continued

```
<400> SEQUENCE: 49
cgggatccta atcctcaggg tcttccgggg cgagctctgg ctgtgggttg attctttttt    60
c                                                                   61

<210> SEQ ID NO 50
<211> LENGTH: 46
<212> TYPE: DNA
<213> ORGANISM: Artificial Sequence
<220> FEATURE:
<223> OTHER INFORMATION: sense primer for substrate PCR

<400> SEQUENCE: 50
catcaccatg gtatgagcgg cggcatggag gagcccagtg accttg                  46

<210> SEQ ID NO 51
<211> LENGTH: 61
<212> TYPE: DNA
<213> ORGANISM: Artificial Sequence
<220> FEATURE:
<223> OTHER INFORMATION: antisense primer for substrate PCR

<400> SEQUENCE: 51
cgggatccta atcctcgggg tcttccgggg cgagttctgg ctgtgggttg attctttttt    60
c                                                                   61

<210> SEQ ID NO 52
<211> LENGTH: 8
<212> TYPE: PRT
<213> ORGANISM: Artificial Sequence
<220> FEATURE:
<223> OTHER INFORMATION: Synthetic substrate fragment

<400> SEQUENCE: 52

Glu Glu Ala Gln Glu Thr Phe Glu
1               5

<210> SEQ ID NO 53
<211> LENGTH: 25
<212> TYPE: DNA
<213> ORGANISM: Artificial Sequence
<220> FEATURE:
<223> OTHER INFORMATION: Sense strand for SEQ ID NO: 52

<400> SEQUENCE: 53
tgaggaagcc caggagacat tcgaa                                         25

<210> SEQ ID NO 54
<211> LENGTH: 26
<212> TYPE: DNA
<213> ORGANISM: Artificial Sequence
<220> FEATURE:
<223> OTHER INFORMATION: Antisense strand for SEQ ID NO: 52

<400> SEQUENCE: 54
gatcttcgaa tgtctcctgg gcttcc                                        26

<210> SEQ ID NO 55
<211> LENGTH: 25
<212> TYPE: DNA
<213> ORGANISM: Artificial Sequence
<220> FEATURE:
<223> OTHER INFORMATION: Sense strand for negative control vector

<400> SEQUENCE: 55
```

```
tgaggagtct gagcagacat tcgaa                                          25

<210> SEQ ID NO 56
<211> LENGTH: 26
<212> TYPE: DNA
<213> ORGANISM: Artificial Sequence
<220> FEATURE:
<223> OTHER INFORMATION: complement of SEQ ID NO: 55

<400> SEQUENCE: 56
gatcttcgaa tgtctgctca gactcc                                         26

<210> SEQ ID NO 57
<211> LENGTH: 36
<212> TYPE: DNA
<213> ORGANISM: Artificial Sequence
<220> FEATURE:
<223> OTHER INFORMATION: sense strand for multiple cloning site

<400> SEQUENCE: 57
ctagctctag aggcgcgccc gggtaccgcg gccgcc                              36

<210> SEQ ID NO 58
<211> LENGTH: 36
<212> TYPE: DNA
<213> ORGANISM: Artificial Sequence
<220> FEATURE:
<223> OTHER INFORMATION: complement of SEQ ID NO: 57 multiple cloning
      site

<400> SEQUENCE: 58
tcgaggcggc cgcggtaccc gggcgcgcct ctagag                              36

<210> SEQ ID NO 59
<211> LENGTH: 177
<212> TYPE: PRT
<213> ORGANISM: Artificial Sequence
<220> FEATURE:
<223> OTHER INFORMATION: sequence of Human Oct-1 POU domain with His6
      tag, expressed from plasmid pT7HPOU1

<400> SEQUENCE: 59

Met Ala Ser Met Thr Gly His His His His His His Gly Met Ser Gly
1               5                   10                  15

Gly Met Glu Glu Pro Ser Asp Leu Glu Glu Leu Glu Gln Phe Ala Lys
            20                  25                  30

Thr Phe Lys Gln Arg Arg Ile Lys Leu Gly Phe Thr Gln Gly Asp Val
        35                  40                  45

Gly Leu Ala Met Gly Lys Leu Tyr Gly Asn Asp Phe Ser Gln Thr Thr
    50                  55                  60

Ile Ser Arg Phe Glu Ala Leu Asn Leu Ser Phe Lys Asn Met Cys Lys
65                  70                  75                  80

Leu Lys Phe Leu Leu Glu Lys Trp Leu Asn Asp Ala Glu Asn Leu Ser
                85                  90                  95

Ser Asp Ser Ser Leu Ser Ser Pro Ser Ala Leu Asn Ser Pro Gly Ile
            100                 105                 110

Glu Gly Leu Ser Arg Arg Arg Lys Lys Arg Thr Ser Ile Glu Thr Asn
        115                 120                 125

Ile Arg Val Leu Glu Lys Ser Phe Leu Glu Asn Gln Lys Pro Thr Ser
    130                 135                 140

Glu Glu Ile Thr Met Ile Ala Asp Gln Leu Asn Met Glu Lys Glu Val
145                 150                 155                 160
```

-continued

```
Ile Arg Val Trp Phe Cys Asn Arg Arg Gln Lys Glu Lys Arg Ile Asn
            165                 170                 175
Pro

<210> SEQ ID NO 60
<211> LENGTH: 5005
<212> TYPE: DNA
<213> ORGANISM: Artificial Sequence
<220> FEATURE:
<223> OTHER INFORMATION: nucleotide sequence of pT7HPOU1

<400> SEQUENCE: 60
gatccacagg acgggtgtgg tcgccatgat cgcgtagtcg atagtggctc caagtagcga      60
agcgagcagg actgggcggc ggccaaagcg gtcggacagt gctccgagaa cgggtgcgca     120
tagaaattgc atcaacgcat atagcgctag cagcacgcca tagtgactgg cgatgctgtc     180
ggaatggacg atatcccgca agaggcccgg cagtaccggc ataaccaagc ctatgcctac     240
agcatccagg gtgacggtgc cgaggatgac gatgagcgca ttgttagatt tcatacacgg     300
tgcctgactg cgttagcaat ttaactgtga taaactaccg cattaaagct tatcgatgat     360
aagctgtcaa acatgagaat tcttgaagac gaaagggcct cgtgatacgc ctatttttat     420
aggttaatgt catgataata atggtttctt agacgtcagg tggcactttt cggggaaatg     480
tgcgcggaac ccctatttgt ttatttttct aaatacattc aaatatgtat ccgctcatga     540
gacaataacc ctgataaatg cttcaataat attgaaaaag gaagagtatg agtattcaac     600
atttccgtgt cgcccttatt ccctttttg cggcattttg ccttcctgtt tttgctcacc     660
cagaaacgct ggtgaaagta aaagatgctg aagatcagtt gggtgcacga gtgggttaca     720
tcgaactgga tctcaacagc ggtaagatcc ttgagagttt cgccccgaa gaacgttttc      780 caatgatgag cactttaaa gttctgctat gtggcgcggt attatcccgt gttgacgccg       840
ggcaagagca actcggtcgc cgcatacact attctcagaa tgacttggtt gagtactcac     900
cagtcacaga aaagcatctt acggatggca tgacagtaag agaattatgc agtgctgcca     960
taaccatgag tgataacact gcggccaact tacttctgac aacgatcgga ggaccgaagg    1020
agctaaccgc ttttttgcac aacatggggg atcatgtaac tcgccttgat cgttgggaac    1080
cggagctgaa tgaagccata ccaaacgacg agcgtgacac cacgatgcct gcagcaatgg    1140
caacaacgtt gcgcaaacta ttaactggcg aactacttac tctagcttcc cggcaacaat    1200
taatagactg gatggaggcg gataaagttg caggaccact tctgcgctcg gcccttccgg    1260
ctggctggtt tattgctgat aaatctggag ccggtgagcg tgggtctcgc ggtatcattg    1320
cagcactggg gccagatggt aagccctccc gtatcgtagt tatctacacg acggggagtc    1380
aggcaactat ggatgaacga atagacaga tcgctgagat aggtgcctca ctgattaagc     1440
attggtaact gtcagaccaa gtttactcat atatacttta gattgattta aaacttcatt    1500
tttaatttaa aaggatctag gtgaagatcc ttttgataa tctcatgacc aaaatccctt     1560
aacgtgagtt ttcgttccac tgagcgtcag accccgtaga aaagatcaaa ggatcttctt    1620
gagatccttt ttttctgcgc gtaatctgct gcttgcaaac aaaaaaacca ccgctaccag    1680
cggtggtttg tttgccggat caagagctac caactctttt tccgaaggta actggcttca    1740
gcagagcgca gataccaaat actgtccttc tagtgtagcc gtagttaggc caccacttca    1800
agaactctgt agcaccgcct acatacctcg ctctgctaat cctgttacca gtggctgctg    1860
ccagtggcga taagtcgtgt cttaccgggt tggactcaag acgatagtta ccggataagg    1920
```

```
cgcagcggtc gggctgaacg gggggttcgt gcacacagcc cagcttggag cgaacgacct    1980
acaccgaact gagataccta cagcgtgagc attgagaaag cgccacgctt cccgaaggga    2040
gaaaggcgga caggtatccg gtaagcggca gggtcggaac aggagagcgc acgagggagc    2100
ttccagggg aaacgcctgg tatctttata gtcctgtcgg gtttcgccac ctctgacttg    2160
agcgtcgatt tttgtgatgc tcgtcagggg gcggagcct atggaaaaac gccagcaacg    2220
cggccttttt acggttcctg gccttttgct ggccttttgc tcacatgttc tttcctgcgt    2280
tatcccctga ttctgtggat aaccgtatta ccgcctttga gtgagctgat accgctcgcc    2340
gcagccgaac gaccgagcgc agcgagtcag tgagcgagga gcggaagag cgcctgatgc    2400
ggtattttct ccttacgcat ctgtgcggta tttcacaccg catatatggt gcactctcag    2460
tacaatctgc tctgatgccg catagttaag ccagtataca ctccgctatc gctacgtgac    2520
tgggtcatgg ctgcgccccg acacccgcca cacccgctg acgcgcctg acgggcttgt    2580
ctgctcccgg catccgctta cagacaagct gtgaccgtct ccgggagctg catgtgtcag    2640
aggttttcac cgtcatcacc gaaacgcgcg aggcagctgc ggtaaagctc atcagcgtgg    2700
tcgtgaagcg attcacagat gtctgcctgt tcatccgcgt ccagctcgtt gagtttctcc    2760
agaagcgtta atgtctggct tctgataaag cgggccatgt taaggggcggt ttttcctgt    2820
ttggtcactg atgcctccgt gtaagggga tttctgttca tgggggtaat gataccgatg    2880
aaacgagaga ggatgctcac gatacggggt actgatgatg aacatgcccg gttactggaa    2940
cgttgtgagg gtaaacaact ggcggtatgg atgcggcggg accagagaaa aatcactcag    3000
ggtcaatgcc agcgcttcgt taatacagat gtaggtgttc cacagggtag ccagcagcat    3060
cctgcgatgc agatccggaa cataatggtg cagggcgctg acttccgcgt ttccagactt    3120
tacgaaacac ggaaaccgaa gaccattcat gttgttgctc aggtcgcaga cgttttgcag    3180
cagcagtcgc ttcacgttcg ctcgcgtatc ggtgattcat tctgctaacc agtaaggcaa    3240
ccccgccagc ctagccgggt cctcaacgac aggagcacga tcatgcgcac ccgtggccag    3300
gacccaacgc tgcccgagat gcgccgcgtg cggctgctgg agatggcgga cgcgatggat    3360
atgttctgcc aagggttggt ttgcgcattc acagttctcc gcaagaattg attggctcca    3420
attcttggag tggtgaatcc gttagcgagg tgccgccggc ttccattcag gtcgaggtgg    3480
cccggctcca tgcaccgcga cgcaacgcgg ggaggcagac aaggtatagg gcggcgccta    3540
caatccatgc caacccgttc catgtgctcg ccgaggcgga taaatcgcc gtgacgatca    3600
gcggtccagt gatcgaagtt aggctggtaa gagccgcgag cgatccttga agctgtccct    3660
gatggtcgtc atctacctgc ctggacagca tggcctgcaa cgcgggcatc ccgatgccgc    3720
cggaagcgag aagaatcata atggggaagg ccatccagcc tcgcgtcgcg aacgccagca    3780
agacgtagcc cagcgcgtcg gccgccatgc cggcgataat ggcctgcttc tcgccgaaac    3840
gtttggtggc gggaccagtg acgaaggctt gagcgagggc gtgcaagatt ccgaataccg    3900
caagcgacag gccgatcatc gtcgcgctcc agcgaaagcg gtcctcgccg aaaatgaccc    3960
agagcgctgc cggcacctgt cctacgagtt gcatgataaa gaagacagtc ataagtgcgg    4020
cgacgatagt catgccccgc gcccaccgga aggagctgac tgggttgaag ctctcaagg    4080
gcatcggtcg acgctctccc ttatgcgact cctgcattag gaagcagccc agtagtaggt    4140
tgaggccgtt gagcaccgcc gccgcaagga atggtgcatg caaggagatg cgcccaaca    4200
gtcccccggc cacgggcct gccaccatac ccacgccgaa acaagcgctc atgagcccga    4260
```

```
agtggcgagc ccgatcttcc ccatcggtga tgtcggcgat ataggcgcca gcaaccgcac    4320
ctgtggcgcc ggtgatgccg gccacgatgc gtccggcgta gaggatcgag atctcgatcc    4380
cgcgaaatta atacgactca ctatagggag accacaacgg tttcccctcta gaaataattt    4440 tgtttaactt taagaaggag atatacatat ggcttctatg actggtcacc accaccatca    4500
ccatggtatg agcggcggca tgaggagcc cagtgacctt gaggagctcg agcagtttgc    4560
caagaccttc aaacaaagac gaatcaaact tggattcact caggtgatg ttgggctcgc    4620 tatggggaaa ctatatggaa atgacttcag ccaaactacc atctctcgat ttgaagcctt    4680
gaacctcagc tttaagaaca tgtgcaagtt gaagccactt ttagagaagt ggctaaatga    4740
tgcagagaac ctctcatctg attcgtccct ctccagccca agtgccctga attctccagg    4800
aattgagggc ttgagcaggc gcaggaagaa acgcaccagc atagagacca acatccgtgt    4860
ggccttagag aagagtttct tggagaatca aaagcctacc tcggaagaga tcactatgat    4920
tgctgatcag ctcaatatgg aaaaagaggt gattcgtgtt tggttctgta accgtcgaca    4980
gaaagaaaaa agaatcaacc catag                                          5005
```

<210> SEQ ID NO 61
<211> LENGTH: 201
<212> TYPE: PRT
<213> ORGANISM: Artificial Sequence
<220> FEATURE:
<223> OTHER INFORMATION: POUSUB1 artificial DNA-PK substrate

<400> SEQUENCE: 61

```
Met Pro Glu Glu Ser Gln Glu Thr Phe Glu Asp Leu Trp Lys Leu Leu
1               5                  10                  15

Pro Gly His His His His His His Gly Met Ser Gly Gly Met Glu Glu
            20                  25                  30

Pro Ser Asp Leu Glu Glu Leu Glu Gln Phe Ala Lys Thr Phe Lys Gln
        35                  40                  45

Arg Arg Ile Lys Leu Gly Phe Thr Gln Gly Asp Val Gly Leu Ala Met
    50                  55                  60

Gly Lys Leu Tyr Gly Asn Asp Phe Ser Gln Thr Thr Ile Ser Arg Phe
65                  70                  75                  80

Glu Ala Leu Asn Leu Ser Phe Lys Asn Met Cys Lys Leu Lys Pro Leu
                85                  90                  95

Leu Glu Lys Trp Leu Asn Asp Ala Glu Asn Leu Ser Ser Asp Ser Ser
            100                 105                 110

Leu Ser Ser Pro Ser Ala Leu Asn Ser Pro Gly Ile Glu Gly Leu Ser
        115                 120                 125

Arg Arg Arg Lys Lys Arg Thr Ser Ile Glu Thr Asn Ile Arg Val Ala
    130                 135                 140

Leu Glu Lys Ser Phe Leu Glu Asn Gln Lys Pro Thr Ser Glu Glu Ile
145                 150                 155                 160

Thr Met Ile Ala Asp Gln Leu Asn Met Glu Lys Glu Val Ile Arg Val
                165                 170                 175

Trp Phe Cys Asn Arg Arg Gln Lys Glu Lys Arg Ile Asn Pro Gln Pro
            180                 185                 190

Glu Leu Ala Pro Glu Asp Pro Glu Asp
        195                 200
```

<210> SEQ ID NO 62
<211> LENGTH: 5873
<212> TYPE: DNA

<213> ORGANISM: Artificial Sequence
<220> FEATURE:
<223> OTHER INFORMATION: Plasmid P349SUB1 sequence

<400> SEQUENCE: 62

```
cgagctccgt cgacaagctt gcggccgcac tcgagcacca ccaccaccac cactgagatc      60
cggctgctaa caaagcccga aaggaagctg agttggctgc tgccaccgct gagcaataac     120
tagcataacc ccttggggcc tctaaacggg tcttgagggg ttttttgctg aaaggaggaa     180
ctatatccgg attggcgaat gggacgcgcc ctgtagcggc gcattaagcg cggcgggtgt     240
ggtggttacg cgcagcgtga ccgctacact tgccagcgcc ctagcgcccg ctcctttcgc     300
tttcttccct cctttctcg ccacgttcgc cggctttccc cgtcaagctc taaatcgggg     360
gctcccttta gggttccgat ttagtgcttt acggcacctc gaccccaaaa aacttgatta     420
gggtgatggt tcacgtagtg ggccatcgcc ctgatagacg gttttcgcc ctttgacgtt     480
ggagtccacg ttctttaata gtggactctt gttccaaact ggaacaacac tcaaccctat     540
ctcggtctat tcttttgatt tataagggat tttgccgatt tcggcctatt ggttaaaaaa     600
tgagctgatt taacaaaaat ttaacgcgaa ttttaacaaa atattaacgt ttacaatttc     660
aggtggcact tttcggggaa atgtgcgcgg aacccctatt tgtttatttt tctaaataca     720
ttcaaatatg tatccgctca tgaattaatt cttagaaaaa ctcatcgagc atcaaatgaa     780
actgcaattt attcatatca ggattatcaa taccatattt ttgaaaaagc cgtttctgta     840
atgaaggaga aaactcaccg aggcagttcc ataggatggc aagatcctgg tatcggtctg     900
cgattccgac tcgtccaaca tcaatacaac ctattaattt cccctcgtca aaataaggt     960
tatcaagtga gaaatcacca tgagtgacga ctgaatccgg tgagaatggc aaaagtttat    1020
gcatttcttt ccagacttgt tcaacaggcc agccattacg ctcgtcatca aaatcactcg    1080
catcaaccaa accgttattc attcgtgatt gcgcctgagc gagacgaaat acgcgatcgc    1140
tgttaaaagg acaattacaa acaggaatcg aatgcaaccg gcgcaggaac actgccagcg    1200
catcaacaat attttcacct gaatcaggat attcttctaa tacctggaat gctgttttcc    1260
cggggatcgc agtggtgagt aaccatgcat catcaggagt acggataaaa tgcttgatgg    1320
tcggaagagg cataaattcc gtcagccagt ttagtctgac catctcatct gtaacatcat    1380
tggcaacgct acctttgcca tgtttcagaa acaactctgg cgcatcgggc ttcccataca    1440
atcgatagat tgtcgcacct gattgcccga cattatcgcg agcccattta cccatata     1500
aatcagcatc catgttggaa tttaatcgcg gcctagagca agacgtttcc cgttgaatat    1560
ggctcataac accccttgta ttactgttta tgtaagcaga cagttttatt gttcatgacc    1620
aaaatccctt aacgtgagtt ttcgttccac tgagcgtcag accccgtaga aaagatcaaa    1680
ggatcttctt gagatccttt ttttctgcgc gtaatctgct gcttgcaaac aaaaaaacca    1740
ccgctaccag cggtggtttg tttgccggat caagagctac caactctttt tccgaaggta    1800
actggcttca gcagagcgca gataccaaat actgtccttc tagtgtagcc gtagttaggc    1860
caccacttca gaactctgt agcaccgcct acatacctcg ctctgctaat cctgttacca    1920
gtggctgctg ccagtggcga taagtcgtgt cttaccgggt tggactcaag acgatagtta    1980
ccggataagg cgcagcggtc gggctgaacg gggggttcgt gcacacagcc cagcttggag    2040
cgaacgacct acaccgaact gagataccta cagcgtgagc tatgagaaag cgccacgctt    2100
cccgaaggga gaaaggcgga caggtatccg gtaagcggca gggtcggaac aggagagcgc    2160
acgagggagc ttccaggggg aaacgcctgg tatctttata gtcctgtcgg gtttcgccac    2220
```

```
ctctgacttg agcgtcgatt tttgtgatgc tcgtcagggg ggcggagcct atggaaaaac   2280
gccagcaacg cggcctttt acggttcctg ccttttgct ggccttttgc tcacatgttc    2340
tttcctgcgt tatcccctga ttctgtggat aaccgtatta ccgcctttga gtgagctgat   2400
accgctcgcc gcagccgaac gaccgagcgc agcgagtcag tgagcgagga agcggaagag   2460
cgcctgatgc ggtattttct ccttacgcat ctgtgcggta tttcacaccg catatatggt   2520
gcactctcag tacaatctgc tctgatgccg catagttaag ccagtataca ctccgctatc   2580
gctacgtgac tgggtcatgg ctgcgccccg acacccgcca acacccgctg acgcgccctg   2640
acgggcttgt ctgctcccgg catccgctta cagacaagct gtgaccgtct ccgggagctg   2700
catgtgtcag aggttttcac cgtcatcacc gaaacgcgcg aggcagctgc ggtaaagctc   2760
atcagcgtgg tcgtgaagcg attcacagat gtctgcctgt tcatccgcgt ccagctcgtt   2820
gagtttctcc agaagcgtta atgtctggct tctgataaag cgggccatgt taagggcggt   2880 ttttcctgt ttggtcactg atgcctccgt gtaaggggga tttctgttca tgggggtaat    2940
gataccgatg aaacgagaga ggatgctcac gatacgggtt actgatgatg aacatgcccg   3000
gttactggaa cgttgtgagg gtaaacaact ggcggtatgg atgcggcggg accagagaaa   3060
aatcactcag ggtcaatgcc agcgcttcgt taatacagat gtaggtgttc cacagggtag   3120
ccagcagcat cctgcgatgc agatccggaa cataatggtg cagggcgctg acttccgcgt   3180
ttccagactt tacgaaacac ggaaaccgaa gaccattcat gttgttgctc aggtcgcaga   3240
cgttttgcag cagcagtcgc ttcacgttcg ctcgcgtatc ggtgattcat tctgctaacc   3300
agtaaggcaa ccccgccagc ctagccgggt cctcaacgac aggagcacga tcatgcgcac   3360
ccgtggggcc gccatgccgg cgataatggc ctgcttctcg ccgaaacgtt tggtggcggg   3420
accagtgacg aaggcttgag cgagggcgtg caagattccg aataccgcaa gcgacaggcc   3480
gatcatcgtc gcgctccagc gaaagcggtc ctcgccgaaa atgacccaga cgctgccgg    3540 cacctgtcct acgagttgca tgataaagaa gacagtcata agtgcggcga cgatagtcat   3600
gccccgcgcc caccggaagg agctgactgg gttgaaggct ctcaagggca tcggtcgaga   3660
tcccggtgcc taatgagtga gctaacttac attaattgcg ttgcgctcac tgcccgcttt   3720
ccagtcggga aacctgtcgt gccagctgca ttaatgaatc ggccaacgcg cgggagagg    3780 cggtttgcgt attgggcgcc agggtggttt ttcttttcac cagtgagacg ggcaacagct   3840
gattgccctt caccgcctgg ccctgagaga gttgcagcaa gcggtccacg ctggtttgcc   3900
ccagcaggcg aaaatcctgt ttgatggtgg ttaacggcgg gatataacat gagctgtctt   3960
cggtatcgtc gtatcccact accgagatat ccgcaccaac gcgcagcccg gactcggtaa   4020
tggcgcgcat tgcgcccagc gccatctgat cgttggcaac cagcatcgca gtgggaacga   4080
tgccctcatt cagcatttgc atggtttgtt gaaaaccgga catggcactc cagtcgcctt   4140
cccgttccgc tatcggctga atttgattgc gagtgagata tttatgccag ccagccagac   4200
gcagacgcgc cgagacagaa cttaatgggc ccgctaacag cgcgatttgc tggtgaccca   4260
atgcgaccag atgctccacg cccagtcgcg taccgtcttc atgggagaaa ataatactgt   4320
tgatgggtgt ctggtcagag acatcaagaa ataacgccgg aacattagtg caggcagctt   4380
ccacagcaat ggcatcctgg tcatccagcg gatagttaat gatcagccca ctgacgcgtt   4440
gcgcgagaag attgtgcacc gccgctttac aggcttcgac gccgcttcgt tctaccatcg   4500
acaccaccac gctggcaccc agttgatcgg cgcgagattt aatcgccgcg acaatttgcg   4560
```

```
acggcgcgtg cagggccaga ctggaggtgg caacgccaat cagcaacgac tgtttgcccg    4620
ccagttgttg tgccacgcgg ttgggaatgt aattcagctc cgccatcgcc gcttccactt    4680
tttcccgcgt tttcgcagaa acgtggctgg cctggttcac cacgcgggaa acggtctgat    4740
aagagacacc ggcatactct gcgacatcgt ataacgttac tggtttcaca ttcaccaccc    4800
tgaattgact ctcttccggg cgctatcatg ccataccgcg aaaggttttg cgccattcga    4860
tggtgtccgg gatctcgacg ctctccctta tgcgactcct gcattaggaa gcagcccagt    4920
agtaggttga ggccgttgag caccgccgcc gcaaggaatg gtgcatgcaa ggagatggcg    4980
cccaacagtc ccccggccac ggggcctgcc accatacccca gccgaaaca gcgctcatg    5040 agcccgaagt ggcgagcccg atcttcccca tcggtgatgt cggcgatata ggcgccagca    5100
accgcacctg tggcgccggt gatgccggcc acgatgcgtc cggcgtagag gatcgagatc    5160
gatctcgatc ccgcgaaatt aatacgactc actatagggg aattgtgagc ggataacaat    5220 tccctctag aagtcgactt taagaaggag taccaagatg cctgaggaaa gtcaggagac    5280
attcgaagat ctatggaaac tacttcctgg tcaccaccac catcaccatg gtatgagcgg    5340
cggcatggag gagcccagtg accttgagga gctcgacag tttgccaaga ccttcaaaca    5400
aagacgaatc aaacttggat tcactcaggg tgatgttggg ctcgctatgg ggaaactata    5460
tggaaatgac ttcagccaaa ctaccatctc tcgatttgaa gccttgaacc tcagctttaa    5520
gaacatgtgc aagttgaagc cacttttaga gaagtggcta aatgatgcag agaacctctc    5580
atctgattcg tccctctcca gcccaagtgc cctgaattct ccaggaattg agggcttgag    5640
caggcgccgt aagaaacgca ccagcataga gaccaacatc cgtgtggcct tagagaagag    5700
tttcttggag aatcaaaagc ctacctcgga agagatcact atgattgctg atcagctcaa    5760
tatggaaaaa gaggtgattc gtgtttggtt ctgtaaccgt cgacagaaag aaaaaagaat    5820
caacccacag ccagaactcg ccccggaaga ccccgaggat taggatccga att            5873
```

<210> SEQ ID NO 63
<211> LENGTH: 18
<212> TYPE: PRT
<213> ORGANISM: Artificial Sequence
<220> FEATURE:
<223> OTHER INFORMATION: DNA-PK synthetic substrate based on human p53
      residues 14-28

<400> SEQUENCE: 63

Pro Leu Ser Gln Glu Thr Phe Ser Gly Leu Trp Lys Leu Leu Pro Pro
1               5                   10                  15

Lys Lys

<210> SEQ ID NO 64
<211> LENGTH: 18
<212> TYPE: PRT
<213> ORGANISM: Artificial Sequence
<220> FEATURE:
<223> OTHER INFORMATION: DNA-PK synthetic substrate based on human p53
      residues 14-28

<400> SEQUENCE: 64

Pro Leu Ser Gln Glu Ala Phe Ala Gly Leu Trp Lys Leu Leu Pro Pro
1               5                   10                  15

Lys Lys